United States Patent
Kosuda et al.

(10) Patent No.: US 8,303,512 B2
(45) Date of Patent: Nov. 6, 2012

(54) PULSE METER, METHOD FOR CONTROLLING PULSE METER, WRISTWATCH-TYPE INFORMATION DEVICE, CONTROL PROGRAM, STORAGE MEDIUM, BLOOD VESSEL SIMULATION SENSOR, AND LIVING ORGANISM INFORMATION MEASUREMENT DEVICE

(75) Inventors: Tsukasa Kosuda, Nagano (JP); Makoto Zakoji, Nagano (JP); Ichiro Aoshima, Hotaka-machi (JP); Yutaka Kawafune, Nagano (JP); Norimitsu Baba, Nagano (JP)

(73) Assignee: Seiko Epson Corporation, Tokyo (JP)

( * ) Notice: Subject to any disclaimer, the term of this patent is extended or adjusted under 35 U.S.C. 154(b) by 1099 days.

(21) Appl. No.: 12/203,599

(22) Filed: Sep. 3, 2008

(65) Prior Publication Data
US 2009/0005695 A1    Jan. 1, 2009

Related U.S. Application Data

(62) Division of application No. 10/793,419, filed on Mar. 5, 2004, now abandoned.

(30) Foreign Application Priority Data

Mar. 19, 2003 (JP) .................. 2003-075839
Mar. 19, 2003 (JP) .................. 2003-075840
Sep. 2, 2003 (JP) .................. 2003-310624

(51) Int. Cl.
*A61B 5/02* (2006.01)
*A61B 5/103* (2006.01)

(52) U.S. Cl. ......... 600/500; 600/501; 600/502; 600/595

(58) Field of Classification Search .......... 600/500–504, 600/481, 483
See application file for complete search history.

(56) References Cited

U.S. PATENT DOCUMENTS
4,832,484 A    5/1989 Aoyagi et al.
(Continued)

FOREIGN PATENT DOCUMENTS
CN    1206337 A    1/1999
(Continued)

OTHER PUBLICATIONS

SW-1 3D acceleration sensor, Journal of XI' an Physical Education Institute vol. 12, Tsinghua Tongfang Optical Disc Co., Ltd. Sep. 1995.

*Primary Examiner* — Navin Natnithithadha
(74) *Attorney, Agent, or Firm* — Global IP Counselors, LLP

(57) ABSTRACT

The present invention realizes calculating a pulse rate accurately, even when a body movement component has no periodical characteristics, by surely removing the body movement component generated in a living organism from a pulse wave component. A pulse wave detecting section includes a pulse wave sensor and outputs a pulse wave detection signal to an MPU functioning as a body motion component removing section. A body motion sensor outputs a body motion detection signal corresponding to a body motion that affects the behavior of venous blood to the MPU. As a result, to the MPU removes the body motion component from the pulse wave detection signal based on the body motion detection signal. A pulse rate calculating section calculates the pulse rate based on the pulse wave detection signal from which the body motion component has been removed. The pulse rate is displayed on a liquid crystal display device.

19 Claims, 117 Drawing Sheets

U.S. PATENT DOCUMENTS

| | | | | |
|---|---|---|---|---|
| 5,542,421 A * | 8/1996 | Erdman | | 600/477 |
| 6,081,742 A | 6/2000 | Amano et al. | | |
| 6,537,225 B1 * | 3/2003 | Mills | | 600/481 |
| 6,712,769 B2 * | 3/2004 | Freund et al. | | 600/503 |
| 6,719,705 B2 * | 4/2004 | Mills | | 600/526 |
| 6,893,402 B2 * | 5/2005 | Freund et al. | | 600/485 |
| 6,921,367 B2 * | 7/2005 | Mills | | 600/481 |
| 7,018,338 B2 | 3/2006 | Vetter et al. | | |
| 7,214,193 B2 * | 5/2007 | Freund et al. | | 600/490 |
| 7,674,231 B2 * | 3/2010 | McCombie et al. | | 600/485 |
| 7,963,921 B1 * | 6/2011 | Freund et al. | | 600/485 |
| 2003/0013976 A1 * | 1/2003 | Freund et al. | | 600/503 |
| 2004/0162493 A1 * | 8/2004 | Mills | | 600/481 |
| 2005/0131306 A9 * | 6/2005 | Mills | | 600/481 |
| 2010/0191080 A1 * | 7/2010 | Mills | | 600/323 |

FOREIGN PATENT DOCUMENTS

| | | |
|---|---|---|
| JP | H02-44534 B2 | 10/1990 |
| JP | H07-116137 A | 5/1995 |
| JP | 3036954 U | 2/1997 |
| JP | 2816944 B2 | 8/1998 |
| JP | H11-276448 A | 10/1999 |
| JP | 2000-051164 A | 2/2000 |
| JP | 2000-308639 A | 11/2000 |
| JP | 2001-275998 A | 10/2001 |
| JP | 3301294 B2 | 4/2002 |
| JP | 2002-224061 A | 8/2002 |
| JP | 2003-250771 A | 9/2003 |
| WO | WO-01/24845 A2 | 4/2001 |

* cited by examiner

PULSE METER, METHOD FOR CONTROLLING PULSE METER, WRISTWATCH-TYPE INFORMATION DEVICE, CONTROL PROGRAM, STORAGE MEDIUM, BLOOD VESSEL SIMULATION SENSOR, AND LIVING ORGANISM INFORMATION MEASUREMENT DEVICE

CROSS-REFERENCE TO THE RELATED APPLICATIONS

This specification claims priority to U.S. patent application Ser. No. 10/793,419, Japanese Patent Application Nos. 2003-75839, 2003-75840, and 2003-310624. All of the disclosures in U.S. patent application Ser. No. 10/793,419, Japanese Patent Application Nos. 2003-75839, 2003-75840, and 2003-310624 are incorporated herein by reference.

BACKGROUND OF THE INVENTION

1. Field of the Invention

The present invention relates to a pulse meter, a method for controlling a pulse meter, a wristwatch-type information device, a control program, a storage medium, a blood vessel simulation sensor, and a living organism information measurement device. The present invention particularly relates to a pulse meter, a method for controlling a pulse meter, a wristwatch-type information device, a control program, a storage medium, a blood vessel simulation sensor, and a living organism information measurement device that are suitable for being mounted on a person's arm and measuring pulse during walking or running.

2. Background Information

Pulse meters mounted on part of the body and designed for measuring pulse during walking or running are conventionally known.

For example, a wristwatch-type pulse meter is disclosed in Japanese Patent No. 2816944. The pulse meter disclosed in this literature employs a configuration wherein the frequency components corresponding to all the harmonic components of a body motion signal detected by an acceleration sensor are removed from the frequency analysis results of a pulse wave signal based on the frequency analysis results of the body motion signal, the frequency components having the maximum power are extracted from among the frequency analysis results of the pulse wave signal from which the harmonic components of the body motion signal have been removed, and the pulse rate is calculated based on the extracted frequency components.

In the above-mentioned conventional pulse meter, not all the body motion components generated in the body and included in the pulse sensor signal are necessarily registered because the body motion components are detected by the acceleration sensor, and it has been possible that the removal of the body motion components may not be complete.

In conventional practice, the body motion components cannot be registered completely, so the body motion signal is identified using the characteristics of the harmonic components from the frequency analysis results in order to remove the body motion components contained in the pulse sensor signal, and because the identified body motion signal is removed and the pulse wave signal extracted, there have been problems in that the body motion components cannot be removed and, consequently, the pulse cannot be correctly determined when the body motion does not have cyclic characteristics.

In view of the above, it will be apparent to those skilled in the art from this disclosure that there exists a need for an improved pulse meter, method for controlling a pulse meter, wristwatch-type information device, control program, storage medium, blood vessel simulation sensor, and living organism information measurement device. This invention addresses this need in the art as well as other needs, which will become apparent to those skilled in the art from this disclosure.

SUMMARY OF THE INVENTION

An object of the present invention is to provide a pulse meter, a method for controlling a pulse meter, a wristwatch-type information device, a control program, a storage medium, a blood vessel simulation sensor, and a living organism information measurement device that can accurately remove the body motion components generated in the body from the pulse components and calculate the pulse rate even when the body motion components do not have cyclic characteristics by more accurately registering the body motion components contained in the pulse sensor signal.

In order to achieve the above-mentioned and other objectives, a living organism information measurement device adapted to be attached to a human body to measure living organism information is provided that comprises a pulse wave detecting section, a body motion component removing section and a living organism information measuring section. The pulse wave detecting section is configured and arranged to output a pulse wave detection signal by using a pulse wave sensor. The body motion component removing section is configured and arranged to detect a body motion component resulting from vein movements of the human body that is contained in the pulse wave detection signal and remove said body motion component contained in the pulse wave detection signal. The living organism information measuring section is configured and arranged to measure living organism information based on the pulse wave detection signal from which the body motion component has been removed.

According to another aspect of the present invention, a pulse meter adapted to be attached to a human body to measure a pulse of the human body is provided that comprises a pulse wave detecting section, a body motion detecting section, a body motion component removing section, and a pulse rate calculating section. The pulse wave detecting section is configured and arranged to detect a pulse wave based on a signal from a pulse wave sensor and output a pulse wave detection signal. The body motion detecting section is configured and arranged to detect accelerations corresponding to body motions that affect a vein behavior based on a signal from an acceleration sensor and output a body motion detection signal. The body motion component removing section is configured and arranged to remove a body motion component contained in the pulse wave detection signal based on the body motion detection signal. The pulse rate calculating section is configured and arranged to calculate a pulse rate based on the pulse wave detection signal from which the body motion component has been removed.

According to another aspect of the present invention, a pulse meter adapted to be attached to a human body to measure a pulse is provided that comprises a pulse wave detecting section, a body motion component removing section and a pulse rate calculating section. The pulse wave detecting section is configured and arranged to detect a pulse wave based on a signal from a pulse wave sensor and output a pulse wave detection signal. The body motion component removing section is configured and arranged to remove a body motion component contained in the pulse wave detection signal based on a relative positional difference in a vertical direction between a position of a heart of the human body and a position where the pulse meter is attached. The pulse rate calculating section is configured and arranged to calculate a pulse rate based on the pulse wave detection signal from which the body motion component has been removed.

According to another aspect of the present invention, a blood vessel simulation sensor adapted to be attached to a human body to simulate a behavior of blood in vein of the human body is provided that comprises a casing, a simulation blood and a behavior detection sensor. The simulation blood is disposed inside the casing and has a viscosity substantially equal to a viscosity of the blood in vein. The behavior detection sensor is configured and arranged to detect a behavior of the simulation blood.

These and other objects, features and advantages of the present invention will become apparent to those skilled in the art from the following detailed description, which, taken in conjunction with the annexed drawings, discloses preferred embodiments of the present invention.

BRIEF DESCRIPTION OF THE DRAWINGS

Referring now to the attached drawings which form a part of this original disclosure:

FIG. 5 shows the frequency analysis results obtained by subjecting the simulated low-frequency signal in FIG. 14 to FFT;

DETAILED DESCRIPTION OF THE PREFERRED EMBODIMENTS

Selected embodiments of the present invention will now be explained with reference to the drawings. It will be apparent to those skilled in the art from this disclosure that the following descriptions of the embodiments of the present invention are provided for illustration only and not for the purpose of limiting the invention as defined by the appended claims and their equivalents.

(1) First Embodiment

Referring to FIGS. 1 through 41, a pulse measurement device 10 will be described herein according to a first embodiment of the present invention. First, the operational basis for the first embodiment will be described prior to a detailed description of the first embodiment.

The output from a pulse wave sensor for detecting pulse waves includes various body motion components in addition to pulse wave components. It is known that these body motion components are generated by the changes in the body, particularly by the behavior of venous blood, originating in the movement of the user (walking/running, arm movement, and the like) whose pulse is to be measured.

However, when a triaxial acceleration sensor is used for detecting the body motion components, it is known that particularly the body motion components in the peripheral direction, or, specifically, in the direction of the X-axis, have a marked effect, but the body motion components in the directions of the other two axes (Y-axis and Z-axis) cannot be ignored. In view of this, vectors are used in the present invention to represent the accelerations along two axial directions when the same body motion components are generated. Moreover, the relationship between the amount of change in a combined vector of the two axial acceleration vectors, and the amount of body motion components (amount of stroke components) included in the output from the pulse wave sensor is determined in the present invention.

Figure 1:
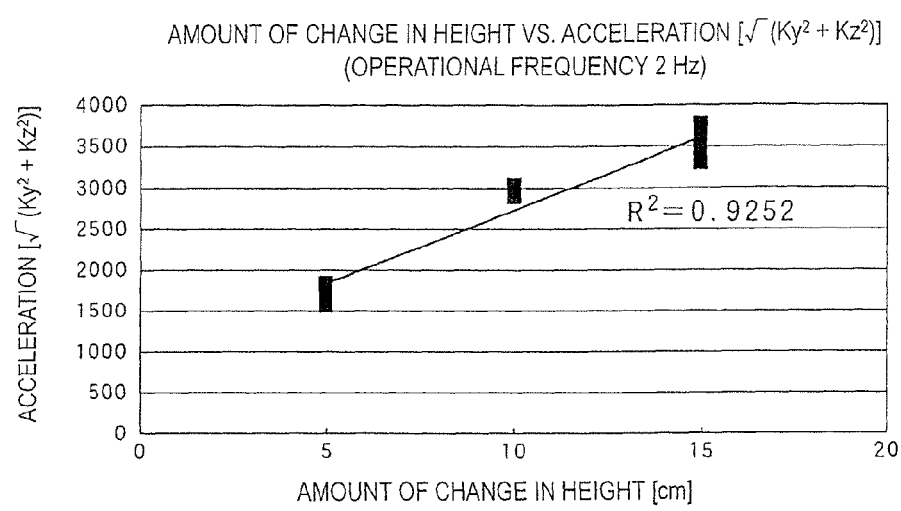
FIG. 1 is an explanatory diagram of the relationship between the amount of change in a combined vector of acceleration vectors along two axes and the amount of body motion components (amount of stroke components) included in the output of a pulse sensor.

FIG. 1 is an explanatory diagram of the relationship between the amount of change in a combined vector of acceleration vectors along two axes and the amount of body motion components (amount of stroke components) included in the output of a pulse sensor. As shown in FIG. 1, it is clear that the amount of change in the combined vector of the two axial acceleration vectors and the amount of body motion components (amount of stroke components) included in the output of the pulse sensor have a substantially proportional relationship. In other words, it is possible to surmise the effect of the venous blood included in the output of the pulse wave sensor if the amount of change in the combined vector of the two axial vectors can be detected.

In view of this, in the first embodiment, the body motion components originating in the veins are detected by a triaxial acceleration sensor, and the pulse rate is accurately detected based on a signal that is free of the effect of venous blood by subtracting the detected output from the output of the pulse wave sensor in a specific proportion.

Figure 2:
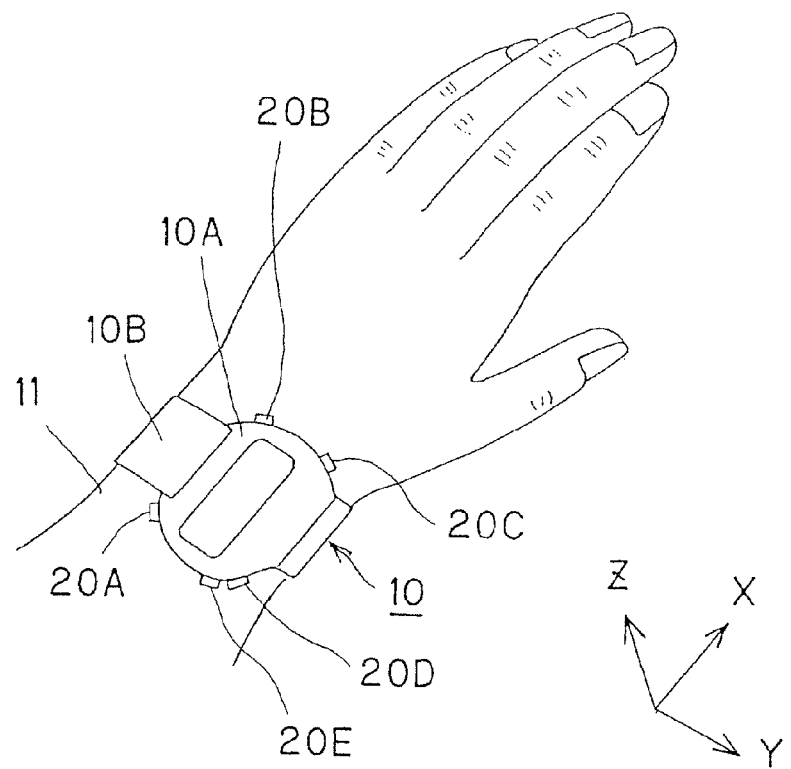
FIG. 2 is an explanatory diagram of the manner in which the pulse measurement device of a first embodiment is mounted.

FIG. 2 is an explanatory diagram of the manner in which the pulse meter or pulse measurement device 10 of the first embodiment is mounted. The pulse measurement device 10 is used while mounted on the user's arm 11, and has a device main body (watchcase) 10A and a wristband 10B for mounting the device main body 10A on the arm. The pulse measurement device 10 according to the present embodiment functions as a living organism information measurement device mounted on the body and designed for measuring living organism information, or as a wristwatch-type information device mounted on the arm.

Figure 3:
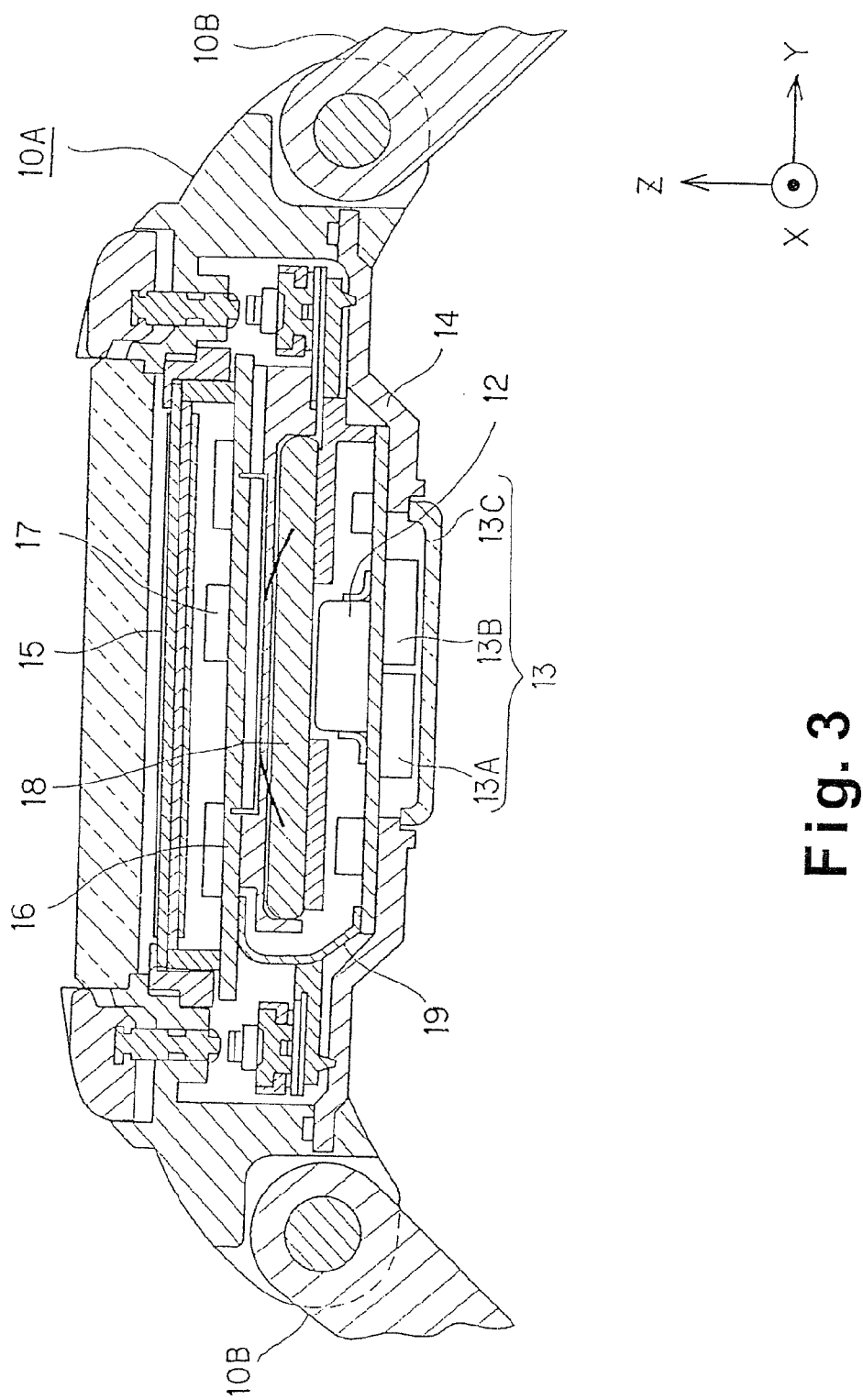
FIG. 3 is a cross-sectional view of the pulse measurement device of the first embodiment.

FIG. 3 is a cross-sectional view of the pulse measurement device of the first embodiment. The back surface of the device main body 10A is pressed against the back of the wrist when the pulse measurement device 10 is mounted with the wristband 10B wound around the wrist. The reverse side of the device main body 10A is provided with a triaxial (X-axis, Y-axis, Z-axis) acceleration sensor 12 and a pulse wave sensor 13. In this case, the triaxial acceleration sensor 12 functions as a body motion sensor.

As shown in FIG. 3, the pulse wave sensor 13 has a light emitting diode (LED) 13A for emitting light to detect pulse waves, a PD (Photo Detector) 13B for receiving the detection light reflected by the body, and transparent glass 13C for protecting the LED 13A and the PD 13B, transmitting the light incident on the LED 13A and reflected light obtained via the body, and directing the light onto the PD 13B. The transparent glass 13C is fixed by means of a back lid 14 as a component of the device main body 10A. The configuration of this pulse wave sensor 13 is designed such that light from the LED 13A is reflected from the back of the wrist through the transparent glass 13C, and the reflected light is received by the photo detector 13B.

The front side of the device main body 10A is provided with a liquid crystal display device 15 for displaying the pulse rate HR and other such living organism information based on the detection results from the pulse wave sensor 13 in addition to the current time and date. Also, the interior of the device main body 10A has a CPU and other such IC circuits on a main board 16, whereby a data processing circuit 17 is configured.

Also, the reverse side of the main board 16 is provided with a battery 18, which supplies power to the triaxial acceleration sensor, the pulse wave sensor 13, the liquid crystal display device 15, and the main board 16.

The triaxial acceleration sensor 12 and the pulse wave sensor 13 are connected with the main board 16 by a heat seal 19. Power is supplied from the main board 16 to the triaxial acceleration sensor 12 and the pulse wave sensor 13 through a wiring formed by the heat seal 19. As a result, an acceleration detection signal is fed from the triaxial acceleration sensor 12 to the main board 16. Also, a pulse wave detection signal is fed from the pulse wave sensor 13 to the main board 16.

The data processing circuit 17 subjects the acceleration detection signal and the pulse wave detection signal to FFT processing, and the pulse rate HR is calculated by analyzing the processing results. The external surface of the device main body 10A is provided with a plurality of button switches 20A, 20B, 20C, 20D, and 20E for time setting, display mode switching, and the like, as shown in FIG. 1.

Figure 4:
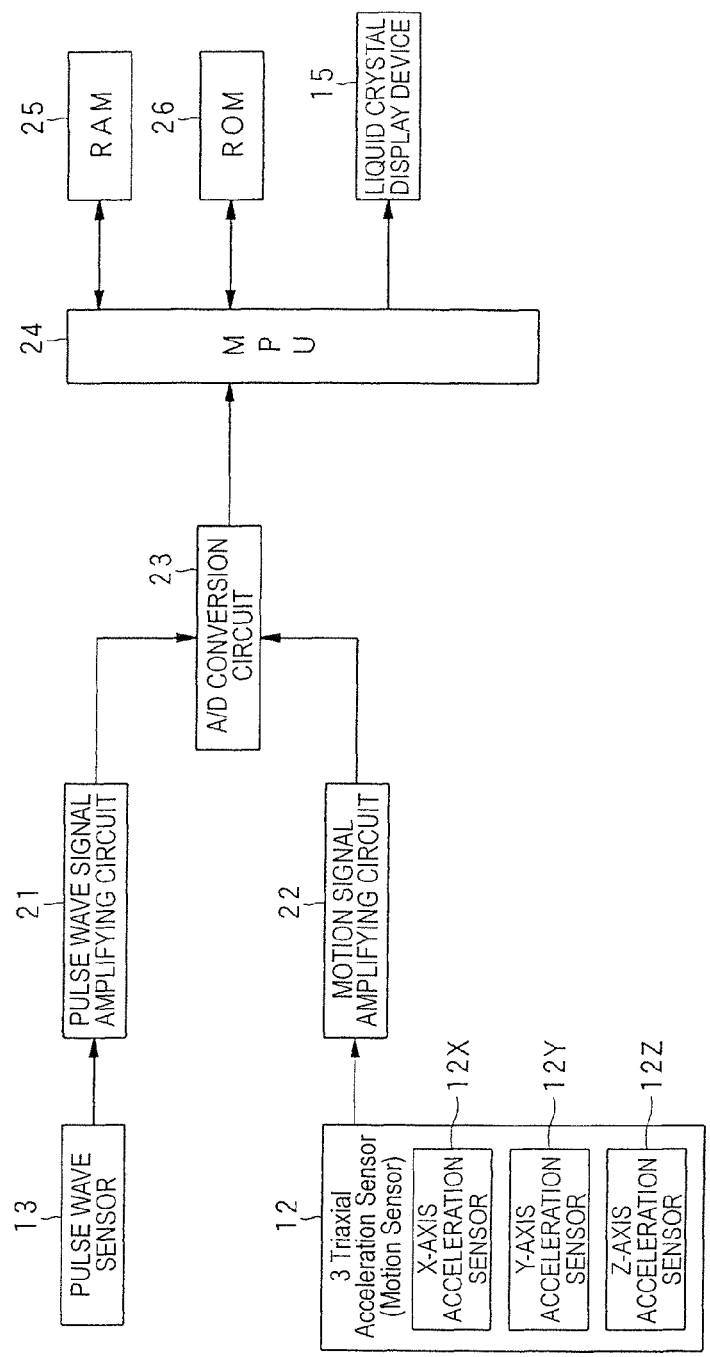
FIG. 4 is a schematic structural block diagram of the pulse measurement device of the first embodiment.

FIG. 4 is a schematic structural block diagram of the pulse measurement device 10 of the first embodiment. In general terms, the pulse measurement device 10 has a pulse wave signal amplifying circuit 21, an acceleration signal amplifying circuit 22, an A/D conversion circuit 23, and a microprocessing unit (MPU) 24, a random access memory (RAM) 25, and a read only memory (ROM) 26 in addition to the triaxial acceleration sensor 12, the pulse wave sensor 13, and the liquid crystal display device 15 described above. Essentially, the pulse wave sensor 13, the pulse wave signal amplifying circuit 21, and the A/D conversion circuit 23 together constitute a pulse wave detecting section. The triaxial acceleration sensor 12, the acceleration signal amplifying circuit 22, and the A/D conversion circuit 23 together constitute a body motion detecting section.

The triaxial acceleration sensor 12 has an X-axis acceleration sensor 12X for detecting acceleration in the direction of the X-axis, a Y-axis acceleration sensor 12Y for detecting acceleration in the direction of the Y-axis, and a Z-axis acceleration sensor 12Z for detecting acceleration in the direction of the Z-axis shown in FIG. 1 or 2.

The pulse wave signal amplifying circuit 21 amplifies the pulse wave detection signal outputted from the pulse wave sensor 13 at a prescribed rate of amplification, and outputs the result to the A/D conversion circuit 23 as an amplified pulse wave detection signal.

The acceleration signal amplifying circuit 22 amplifies the X-axis acceleration detection signal, the Y-axis acceleration detection signal, and the Z-axis acceleration detection signal outputted from the triaxial acceleration sensor 12 at a prescribed rate of amplification, and outputs the result to the A/D conversion circuit 23 as an amplified X-axis acceleration detection signal, an amplified Y-axis acceleration detection signal, and an amplified Z-axis acceleration detection signal.

The A/D conversion circuit 23 performs analog/digital conversion separately on the inputted amplified pulse wave detection signal, the amplified X-axis acceleration detection signal, the amplified Y-axis acceleration detection signal, the amplified Z-axis acceleration detection signal, and the amplified pressure detection signal, and outputs the result to the MPU 24 as detected pulse wave data or pulse wave detection data, detected X-axis acceleration data Kx, Y-axis acceleration data Ky, and Z-axis acceleration data Kz.

The MPU 24 stores the detected X-axis acceleration data Kx, the detected Y-axis acceleration data Ky, and the detected Z-axis acceleration data Kz in the RAM 25, calculates the pulse rate based on a control program stored in the ROM 26, and displays the result on the display device 15.

More specifically, the MPU 24 chronologically arranges the detected pulse wave data stored in the RAM 25 as well as detected body motion data or body motion detection data obtained based on the detected X-axis acceleration data Kx, the detected Y-axis acceleration data Ky, and the detected Z-axis acceleration data Kz, and determines residual data, which is the difference between the detected pulse wave data and the detected body motion data for each sampling time. Frequency analysis (FFT: Fast Fourier Transformation) is then performed on the residual data, the harmonic components of the pulse wave are extracted, and the pulse rate is calculated from the frequency. Therefore, the MPU 24 also essentially functions as a body motion component generating section.

A more specific pulse rate calculation process will now be described.

Figure 5:
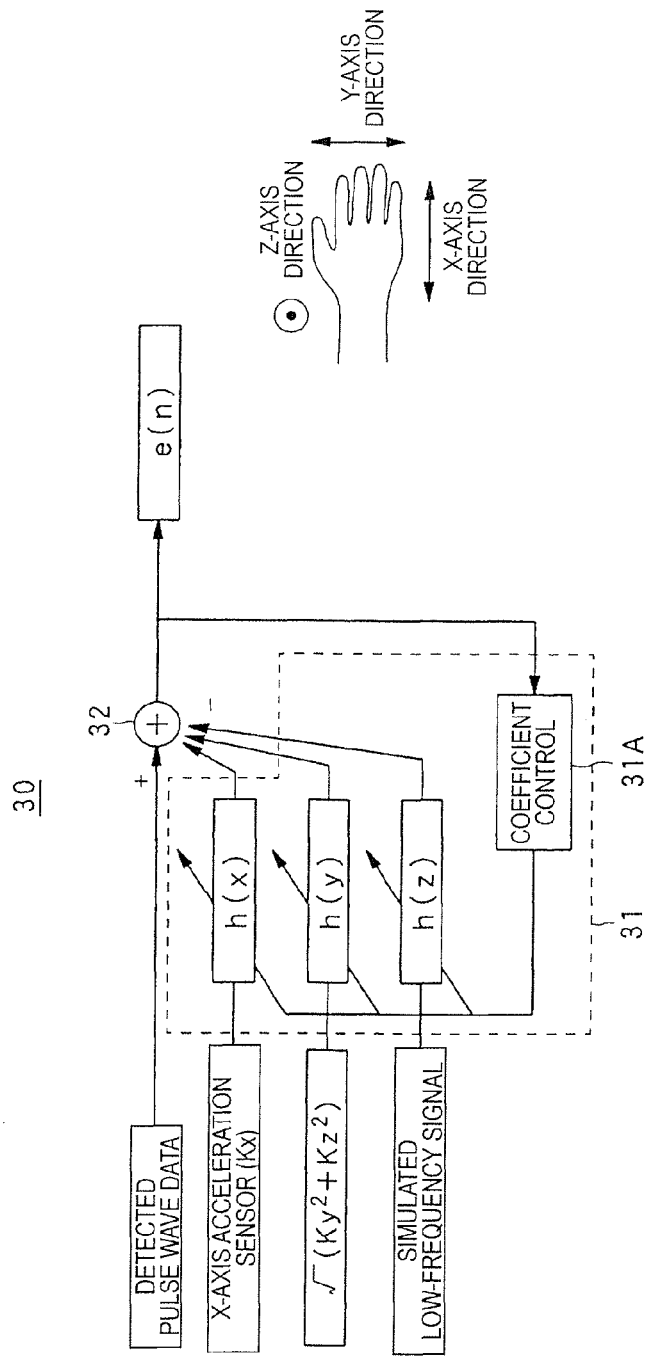
FIG. 5 is a schematic structural block diagram of an example of an adaptive filter of the first embodiment.

FIG. 5 is a schematic structural block diagram of one example of an adaptive filter 30 of the first embodiment. In general terms, the adaptive filter 30 has a filter coefficient generating section 31 and a synthesizer 32.

A coefficient controller 31A of the filter coefficient generating section 31 functions as a body motion component removing section and generates an adaptive filter coefficient h based on previously outputted data by the synthesizer 32 to which the filter has been applied. The filter coefficient generating section 31 then applies the adaptive filter coefficient h generated by the coefficient controller 31A to a simulated low-frequency signal (=z) and to combined acceleration vector data (=y), which is the combined data of the X-axis acceleration data Kx, the Y-axis acceleration data Ky, and the Z-axis acceleration data Kz as inputted body motion component detection signals; then generates body motion removal data h(x), h(y), and h(z); and outputs the result to the synthesizer 32.

The synthesizer 32 functions as a removal processing section; combines the extracted detected pulse wave data (=pulse wave components+body motion components) and the body motion removal data h(x), h(y), and h(z); substantially removes (subtracts) the body motion components contained in the current detected pulse wave data; and extracts pulse wave components e(n).

The reasons for using a simulated low-frequency signal will now be described. According to the experiments in developing the present invention, sometimes low-frequency fluctuating components remained in the resulting pulse wave components, and the pulse rate could not be accurately determined even when the body motion removal data h(x) and h(y) was removed from the detected pulse wave data. This is thought to be the effect of breathing and nerve activity, but to detect these signals and remove their effect would require a large and bulky system and would make it impossible to achieve a portable pulse measurement device.

In the present invention, these effects were removed by applying an adaptive filter upon multiplying the output signal from the triaxial acceleration sensor 12, which is the body motion detection sensor, by a simulated low-frequency signal whose frequency corresponds to a low-frequency variation component. In this case, the simulated low-frequency signal must have a specific frequency distribution during frequency analysis and remove low-frequency variation components, and should be a triangular or rectangular wave of 0.5 Hz or less in view of the fact that the frequency band thereof is 0.5 Hz or less. The frequency band and the waveform can be appropriately varied in accordance with the actually contained low-frequency variation components.

The specific pulse rate detection process of the first embodiment will now be described with reference to FIGS. 6 through 19.

Figure 6:
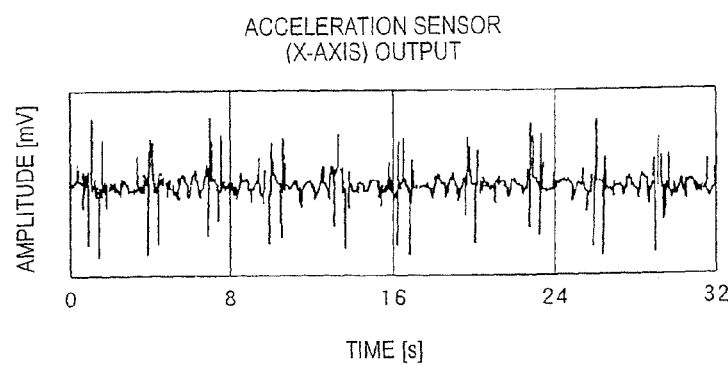
FIG. 6 is a graph showing a chronological arrangement of X-axis acceleration data Kx corresponding to an X-axis acceleration detection signal outputted from an X-axis acceleration sensor 12X.
Figure 7:
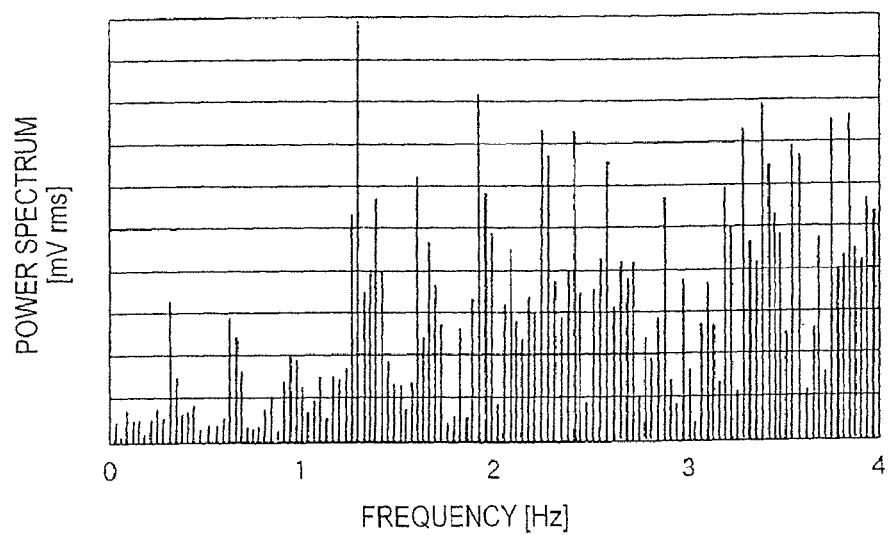
FIG. 7 shows the frequency analysis results obtained by subjecting the detected X-axis acceleration data Kx in FIG. 6 to FFT.

FIG. 6 is a graph showing a chronological arrangement of X-axis acceleration data Kx for the X-axis acceleration detection signal outputted from the X-axis acceleration sensor 12X. FIG. 7 shows the frequency analysis results obtained by subjecting the detected X-axis acceleration data Kx in FIG. 6 to FFT.

Figure 8:
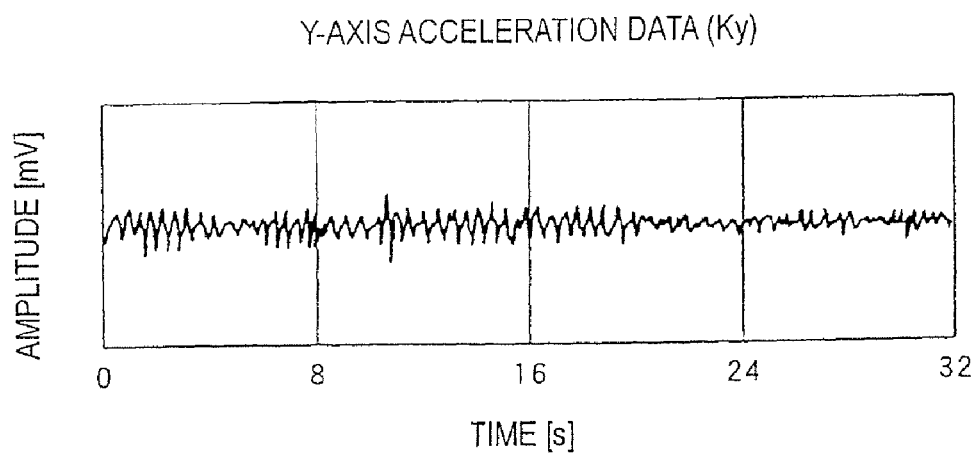
FIG. 8 is a graph showing a chronological arrangement of Y-axis acceleration data Ky corresponding to a Y-axis acceleration detection signal outputted from a Y-axis acceleration sensor 12Y.
Figure 9:
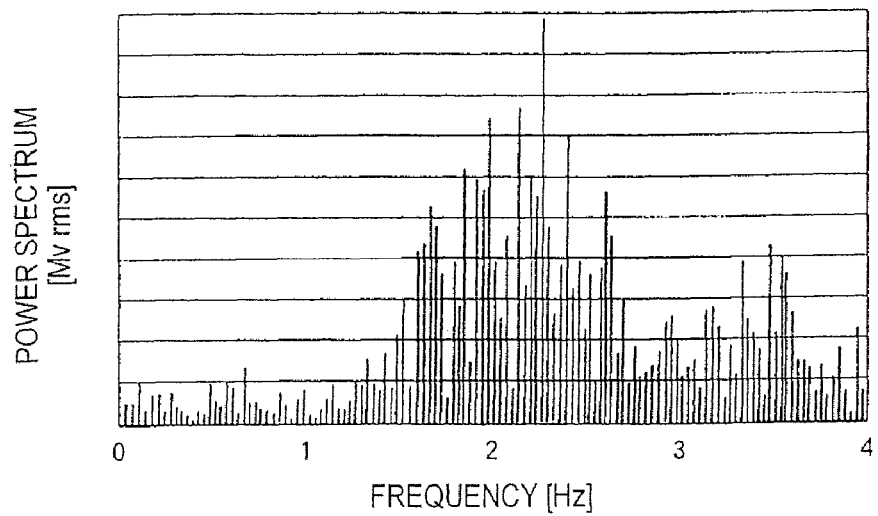
FIG. 9 shows the frequency analysis results obtained by subjecting the detected Y-axis acceleration data Ky in FIG. 8 to FFT.

FIG. 8 is a graph showing a chronological arrangement of Y-axis acceleration data Ky for the Y-axis acceleration detection signal outputted from the Y-axis acceleration sensor 12Y. FIG. 9 shows the frequency analysis results obtained by subjecting the detected Y-axis acceleration data Ky in FIG. 8 to FFT.

Figure 10:
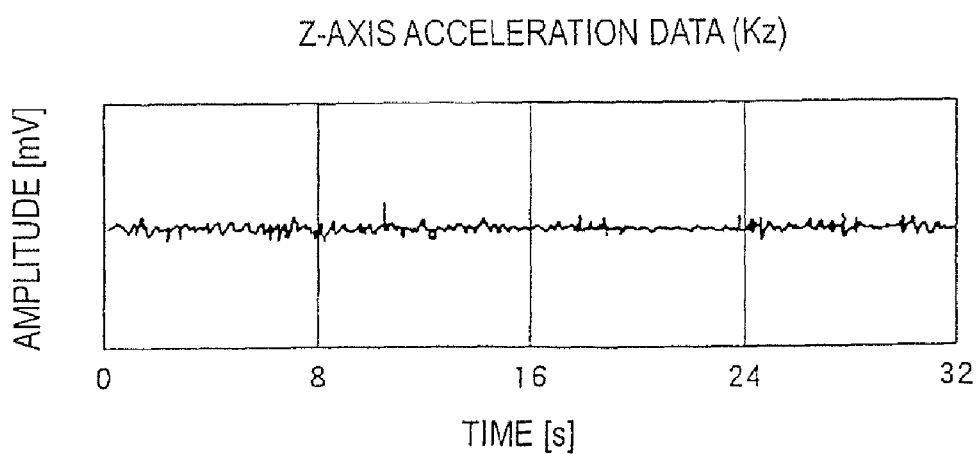
FIG. 10 is a graph showing a chronological arrangement of Z-axis acceleration data Kz corresponding to a Z-axis acceleration detection signal outputted from a Z-axis acceleration sensor 12Z.
Figure 11:
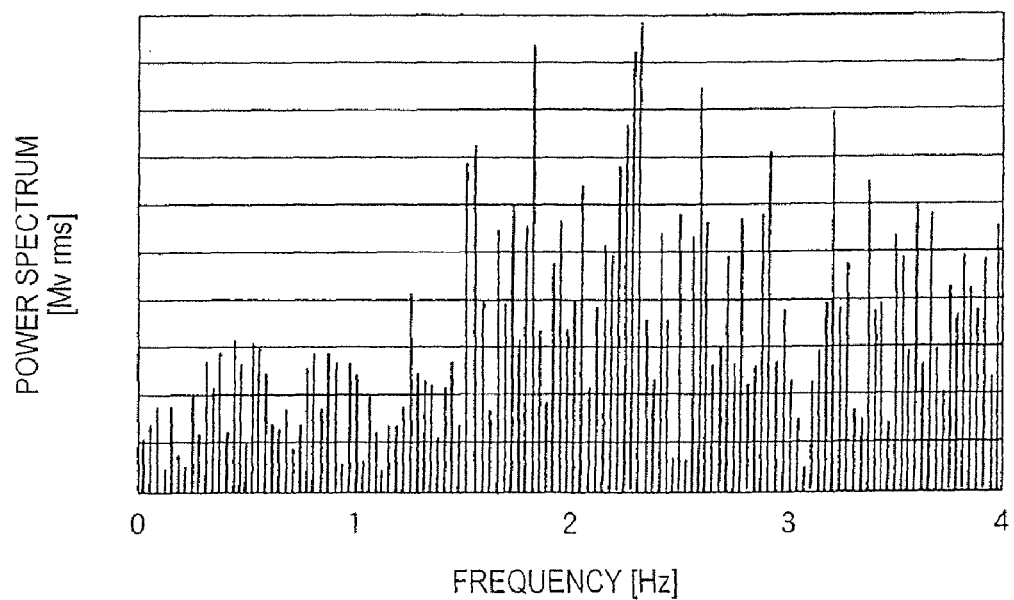
FIG. 11 shows the frequency analysis results obtained by subjecting the detected Z-axis acceleration data Kz in FIG. 10 to FFT.

FIG. 10 is a graph showing a chronological arrangement of Z-axis acceleration data Kz for the Z-axis acceleration detection signal outputted from the Z-axis acceleration sensor 12Z. FIG. 11 shows the frequency analysis results obtained by subjecting the detected Z-axis acceleration data Kz in FIG. 10 to FFT.

It is clear from comparing FIGS. 6, 8, and 10 that the effect of the X-axis acceleration components is greater than the effect of the Y-axis acceleration components or the Z-axis acceleration components. Therefore, the inventors decided to treat the Y-axis acceleration components and the Z-axis acceleration components in an integral manner, as described above, and to detect the amount of change in the combined vector of the acceleration vectors along two axes with the intention of simplifying the process while maintaining measuring precision.

Figure 12:
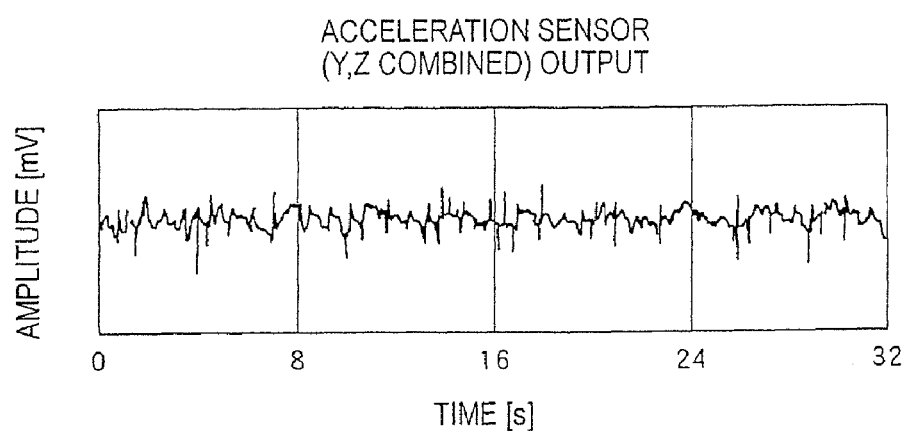
FIG. 12 is a graph obtained by treating the Y-axis acceleration data Ky corresponding to the Y-axis acceleration detection signal outputted from the Y-axis acceleration sensor 12Y, and the Z-axis acceleration data Kz corresponding to the Z-axis acceleration detection signal outputted from the Z-axis acceleration sensor 12Z as vectors, and chronologically arranging combined acceleration vector data obtained as a combined vector thereof.
Figure 13:
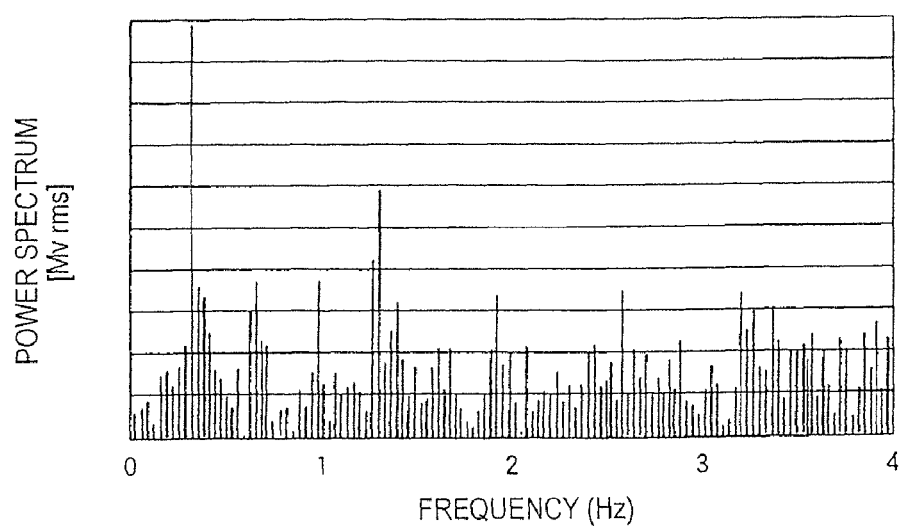
FIG. 13 shows the frequency analysis results obtained by subjecting the combined acceleration vector data ($=\sqrt{(Ky^2+Kz^2)}$) in FIG. 12 to FFT.

FIG. 12 is a graph obtained by treating the Y-axis acceleration data Ky corresponding to the Y-axis acceleration detection signal outputted from the Y-axis acceleration sensor 12Y, and the Z-axis acceleration data Kz corresponding to the Z-axis acceleration detection signal outputted from the Z-axis acceleration sensor 12Z as vectors, and chronologically arranging combined acceleration vector data obtained as a combined vector thereof. FIG. 13 shows the frequency analysis results obtained by subjecting the combined acceleration vector data (=$\sqrt{(Ky^2+Kz^2)}$), or, specifically, the biaxial acceleration combined components in FIG. 12 to FFT.

Figure 14:
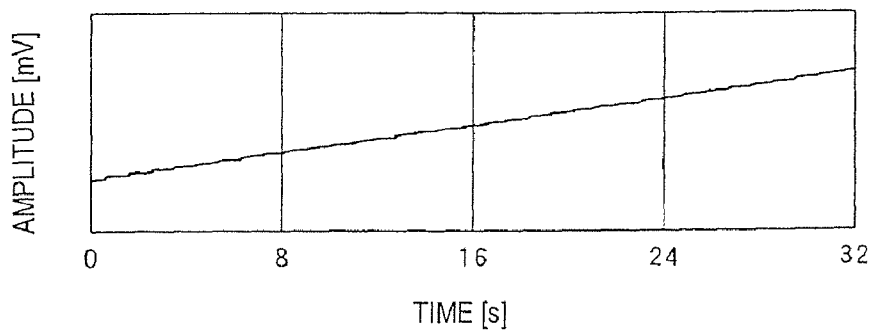
FIG. 14 is a graph showing a chronological arrangement of a preset simulated low-frequency signal (using a triangular wave)
Figure 15:
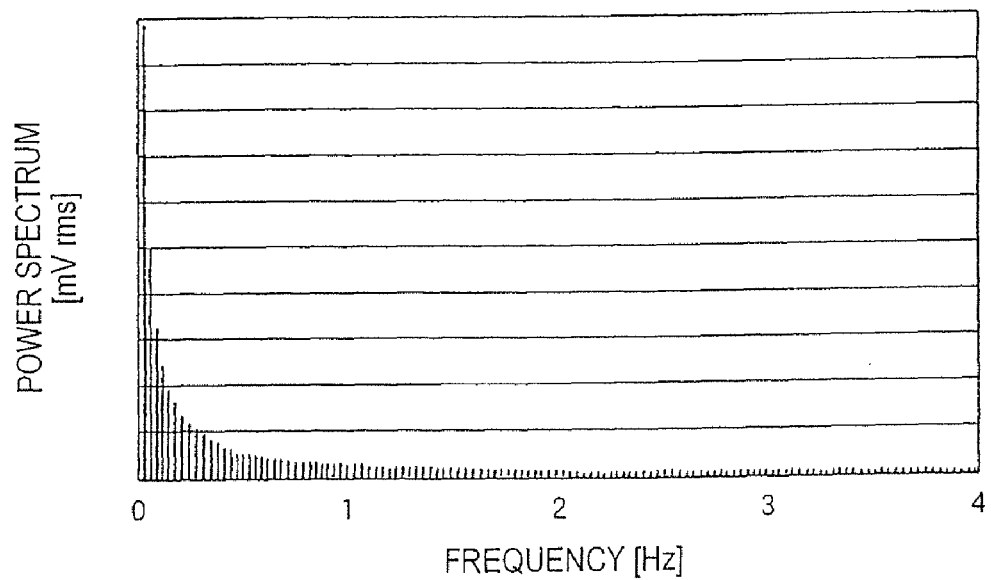

FIG. 14 is a graph showing a chronological arrangement of a preset simulated low-frequency signal (using a triangular wave). FIG. 15 shows the frequency analysis results obtained by subjecting the simulated low-frequency signal in FIG. 14 to FFT. As can be seen from FIG. 15, the frequency is approximately 0.5 Hz or less, with a specific frequency distribution.

Figure 16:
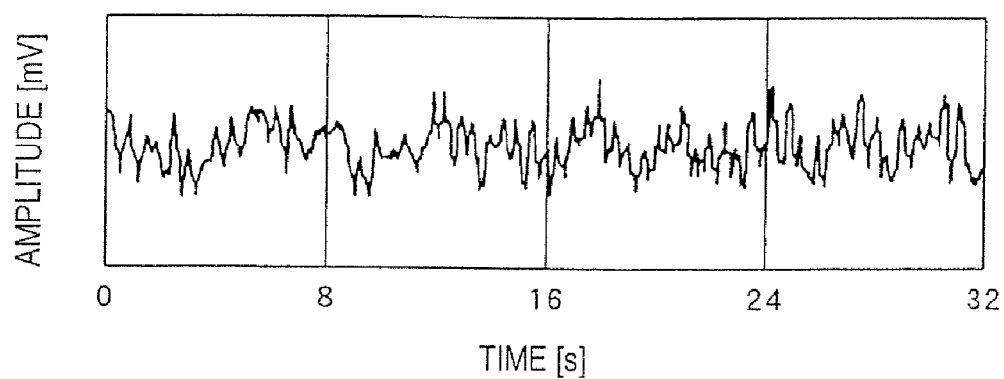
FIG. 16 is a graph of a chronological arrangement of one example of the detected pulse data.
Figure 17:
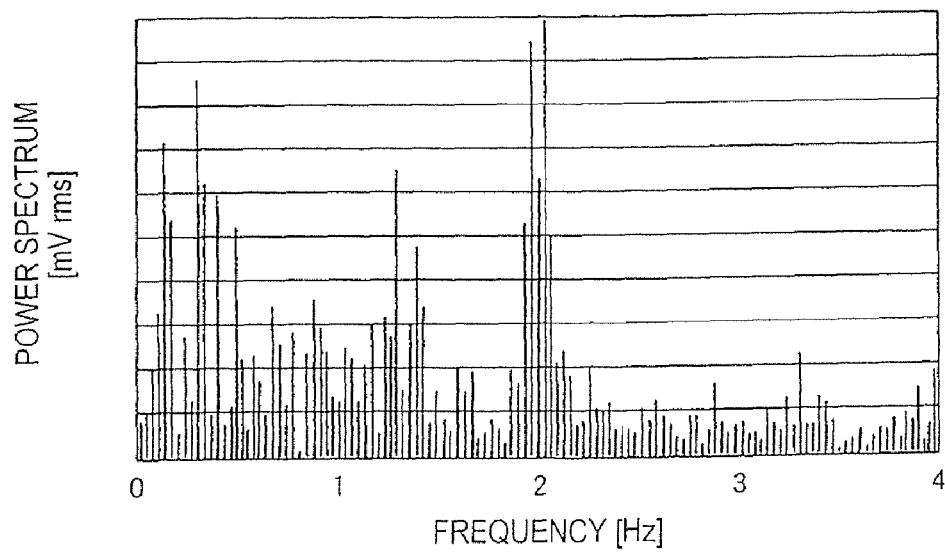
FIG. 17 shows the frequency analysis results obtained by subjecting the detected pulse data in FIG. 16 to FFT.

FIG. 16 is a graph of a chronological arrangement of one example of the detected pulse data. FIG. 17 shows the frequency analysis results obtained by subjecting the detected pulse data in FIG. 16 to FFT.

First, the MPU 24 sequentially reads the detected pulse wave data, the detected X-axis acceleration data, the detected Y-axis acceleration data, and the detected Z-axis acceleration data stored in the RAM 25, and outputs the detected pulse wave data in a single sampling period to the synthesizer 32. In parallel with this, the MPU 24 outputs the detected X-axis acceleration data Kx, the detected Y-axis acceleration data Ky, and the detected Z-axis acceleration data Kz corresponding to the detected pulse wave data outputted to the synthesizer 32 to the filter coefficient generating section 31.

Thus, the coefficient controller 31A of the filter coefficient generating section 31 generates the adaptive filter coefficient h based on previously outputted data by the synthesizer 32 to which the filter has been applied. Under control from the coefficient controller 31A, the filter coefficient generating section 31 then applies the adaptive filter coefficient h to the simulated low-frequency signal (=z), to the detected X-axis acceleration data Kx (=x), and to combined acceleration vector data (=y), which is the combined data of the Y-axis acceleration data Ky and the Z-axis acceleration data Kz, inputted as body motion component detection signals; generates body motion removal data h(x), h(y), and h(z); and outputs the result to the synthesizer 32.

Thus, the synthesizer 32 combines the current pulse wave data and the body motion removal data h(x), h(y), and h(z); substantially removes (subtracts) the body motion components contained in the current detected pulse wave data; extracts the pulse wave components; and outputs the residual data e(n), which is the data to which the adaptive filter has been applied.

Figure 18:
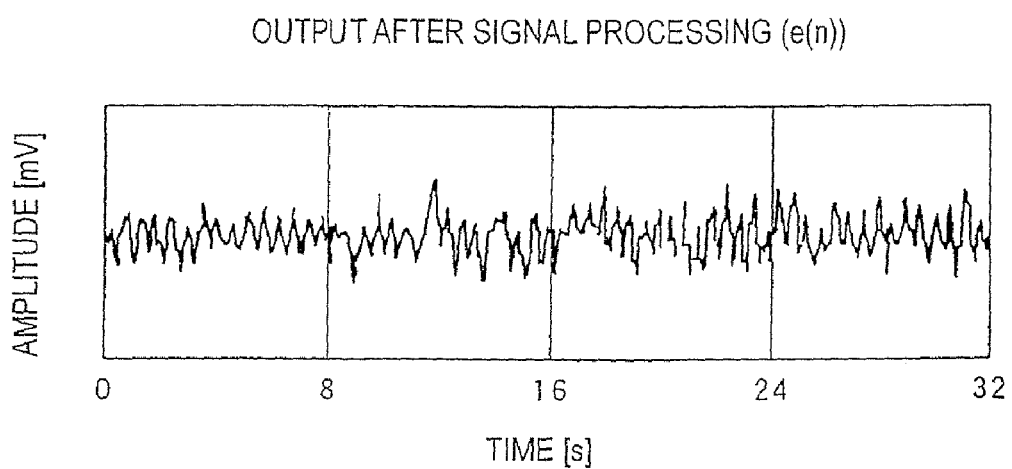
FIG. 18 is a graph plotted as a result of a chronological arrangement of residual data obtained by combining the signals obtained by applying an adaptive filter to the amplified X-axis acceleration detection signal in FIG. 6, the combined acceleration vector signal in FIG. 12, and the simulated low-frequency signal in FIG. 14 for the pulse wave detection signal in FIG. 16.

FIG. 18 is a graph plotted as a result of a chronological arrangement of the residual data obtained by combining the signals obtained by applying an adaptive filter to the amplified X-axis acceleration detection signal in FIG. 6, the combined acceleration vector signal in FIG. 12, and the simulated low-frequency signal in FIG. 14 for the pulse wave detection signal in FIG. 16.

Figure 19:
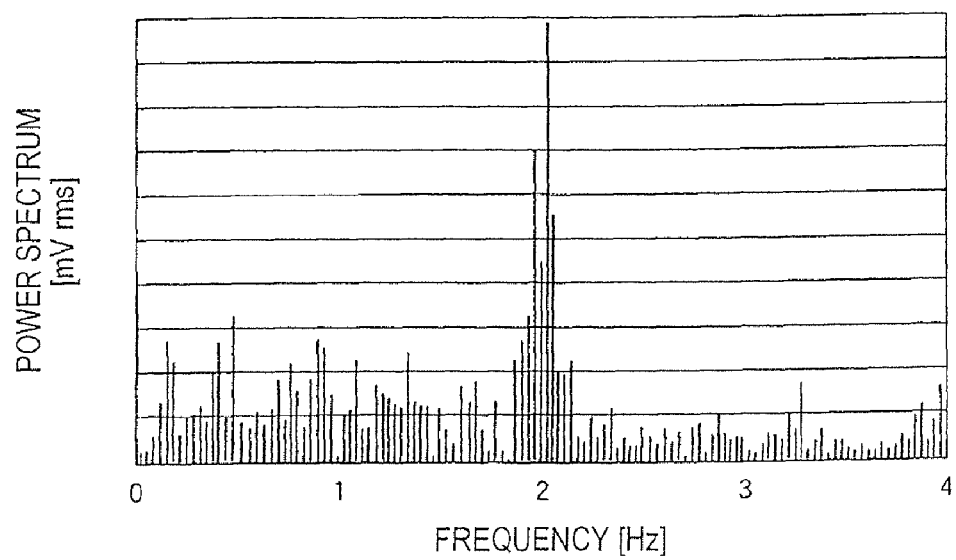
FIG. 19 shows the frequency analysis results obtained by subjecting the residual data in FIG. 18 to FFT.

Next, the MPU 24 subjects the residual data to FFT. FIG. 19 shows the frequency analysis results obtained by subjecting the residual data in FIG. 18 to FFT. Thus, the frequency analysis results thus obtained have the body motion components originating in the veins substantially removed from the output signal (pulse wave components+body motion components) of the pulse wave sensor, and are, specifically, pulse wave data that primarily corresponds to the pulse wave components.

For the sake of comparison, pulse wave data obtained when a simulated low-frequency signal has not been used will now be described.

Figure 20:
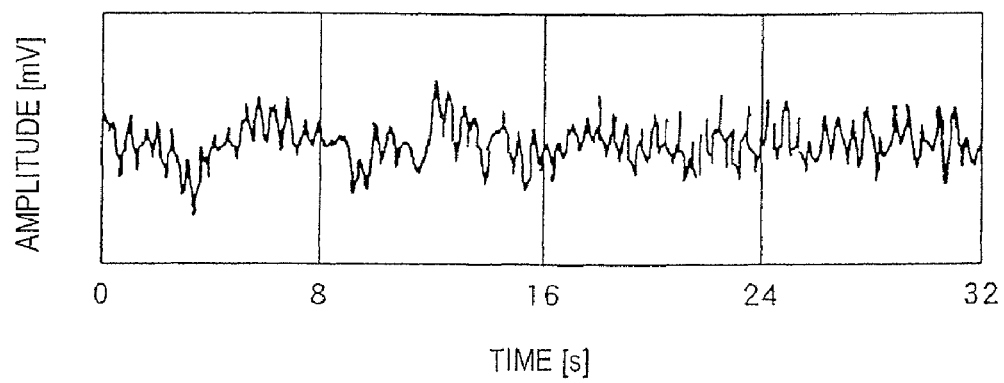
FIG. 20 is a graph plotted as a result of a chronological arrangement of residual data obtained by combining the signals obtained by applying an adaptive filter to the amplified X-axis acceleration detection signal in FIG. 6 and the combined acceleration vector signal in FIG. 12 for the pulse wave detection signal in FIG. 16.
Figure 21:
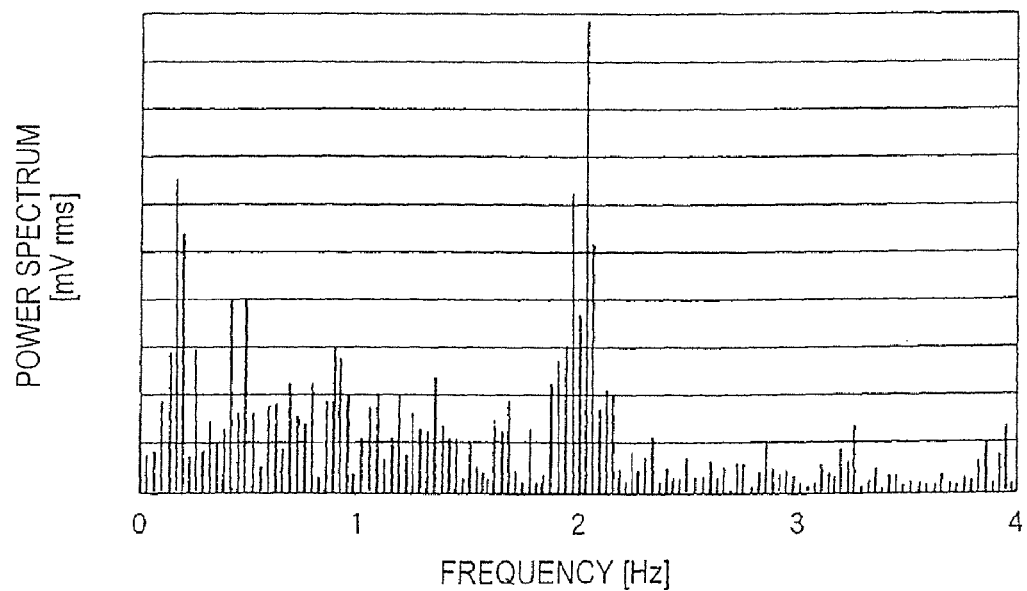
FIG. 21 shows the frequency analysis results obtained by subjecting the residual data in FIG. 20 to FFT.

FIG. 20 is a graph of a chronological arrangement of residual data obtained by combining the signals obtained by applying an adaptive filter to the amplified X-axis acceleration detection signal in FIG. 6 and the combined acceleration vector signal in FIG. 12 for the pulse wave detection signal in FIG. 16. FIG. 21 shows the frequency analysis results obtained by subjecting the residual data in FIG. 20 to FFT.

It can readily be seen by comparing FIGS. 19 and 21 that low-frequency variation components can be reduced in accordance with the configuration of the first embodiment, and that the effect of low-frequency variation components in pulse rate detection can therefore be removed with ease.

Furthermore, the MPU 24 calculates the pulse rate from the frequency on the assumption that the maximum frequency components of the resulting pulse wave data primarily containing pulse wave components constitute the pulse spectrum. Therefore, the MPU 24 functions as a pulse rate calculating section. The MPU 24 then displays the pulse rate on the liquid crystal display device 15.

Furthermore, the MPU 24 can also be configured so as to calculate the pitch or the number of steps of the user from the detected body motion components. In this case, the MPU 24 functions as a body motion information detecting section for detecting the pitch or the number of steps.

As described above, according to the first embodiment, variation in the veins, which is the main factor in the body motion components generated in the body, can be surely detected and registered by using the pulse wave sensor 13 and the triaxial acceleration sensor 12 functioning as a body motion sensor, and also by using a simulated low-frequency signal. Therefore, the body motion components can be surely removed, making it possible to accurately detect pulse wave components, and hence to accurately measure the pulse rate.

(1.1) First Alternative of the First Embodiment

A pulse measurement device according to the first alternative of the first embodiment is similar to the first embodiment, except that the first embodiment uses combined acceleration vector data ($=\sqrt{(Ky^2+Kz^2)}$), which is the combined data of the Y-axis acceleration data Ky and the Z-axis acceleration data Kz, while the first alternative uses combined acceleration vector data ($=\sqrt{(Kx^2+Ky^2+Kz^2)}$), which is a combination of the following three types of acceleration data: the X-axis acceleration data, the Y-axis acceleration data, and the Z-axis acceleration data, specifically, the combined components of triaxial acceleration. Therefore, the configuration of the first alternative of the first embodiment is essentially the same as the configuration of the pulse measurement device 10 shown in FIGS. 2 through 4, except that the MPU 24 is configured with an adaptive filter 40 of the first alternative instead of being configured with the adaptive filter 30 of the first embodiment.

Figure 22:
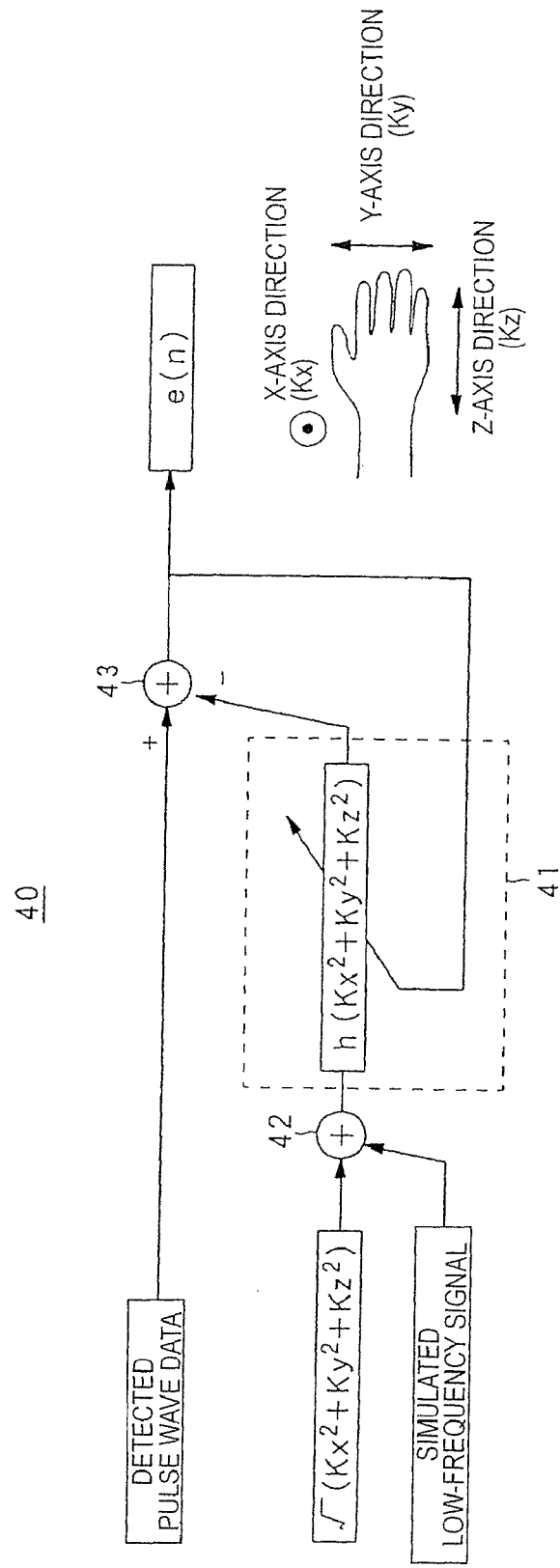
FIG. 22 is a schematic structural block diagram of one example of an adaptive filter according to a first alternative of the first embodiment.

FIG. 22 is a schematic structural block diagram of one example of the adaptive filter 40 of the first alternative of the first embodiment. In general terms, the adaptive filter 40 has a filter coefficient generating section 41, an integrator 42, and a synthesizer 43.

The filter coefficient generating section 41 functions as a body motion component removing section, and generates an adaptive filter coefficient h based on data previously outputted by the synthesizer 43 after the filter has been applied.

In parallel with this, the integrator 42 multiplies the combined acceleration vector data ($=\sqrt{(Kx^2+Ky^2+Kz^2)}$), which is a combination of the following three types of acceleration data: X-axis acceleration data, Y-axis acceleration data, and Z-axis acceleration data, by a preset simulated low-frequency signal, and outputs the result to the filter coefficient generating section 41.

As a result, the filter coefficient generating section 41 applies the generated adaptive filter coefficient h to the output from the integrator 42, generates body motion removal data $h(Kx^2+Ky^2+Kz^2)$, and outputs the result to the synthesizer 43.

The synthesizer 43 functions as a removal processing section; combines the extracted detected pulse wave data (=pulse wave components+body motion components) with the body motion removal data $h(Kx^2+Ky^2+Kz^2)$, substantially removes (subtracts) the body motion components contained in the current detected pulse wave data, and extracts the residual data e(n).

The specific pulse rate calculating process of the first alternative will now be described.

Figure 23:
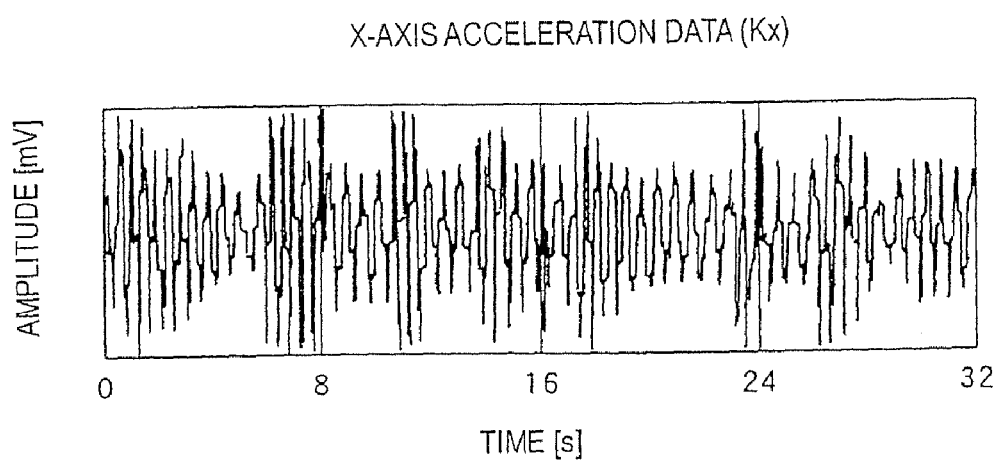
FIG. 23 is a graph of a chronological arrangement of detected X-axis acceleration data Kx.
Figure 24:
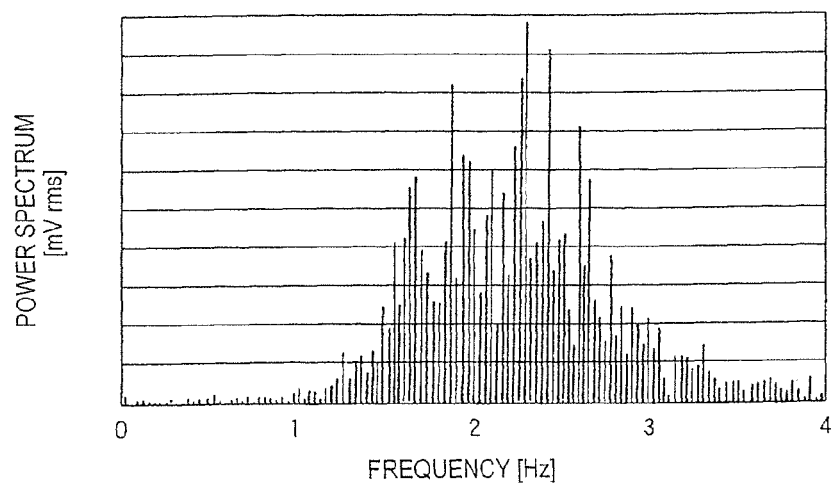
FIG. 24 shows the frequency analysis results obtained by subjecting the detected X-axis acceleration data Kx in FIG. 23 to FFT.

FIG. 23 is a graph of a chronological arrangement of detected X-axis acceleration data Kx for the X-axis acceleration detection signal outputted from the X-axis acceleration sensor 12X. FIG. 24 shows the frequency analysis results obtained by subjecting the detected X-axis acceleration data Kx in FIG. 23 to FFT.

Figure 25:
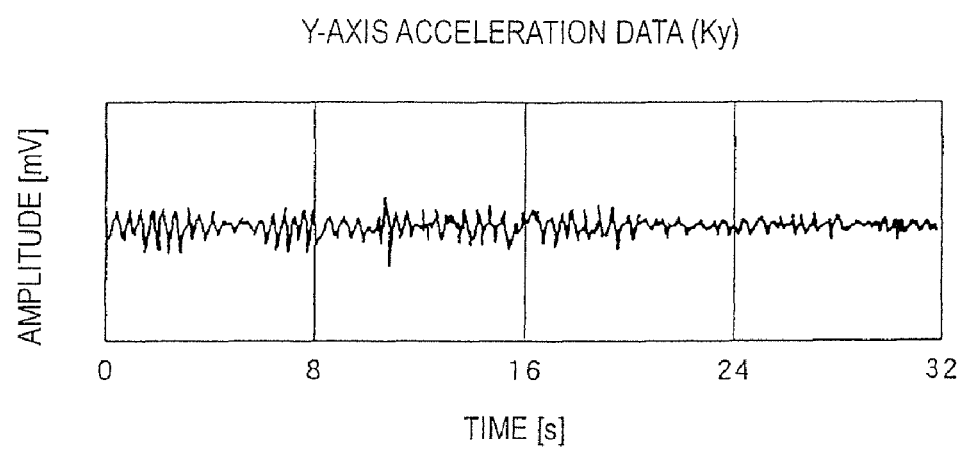
FIG. 25 is a graph of a chronological arrangement of Y-axis acceleration data Ky.
Figure 26:
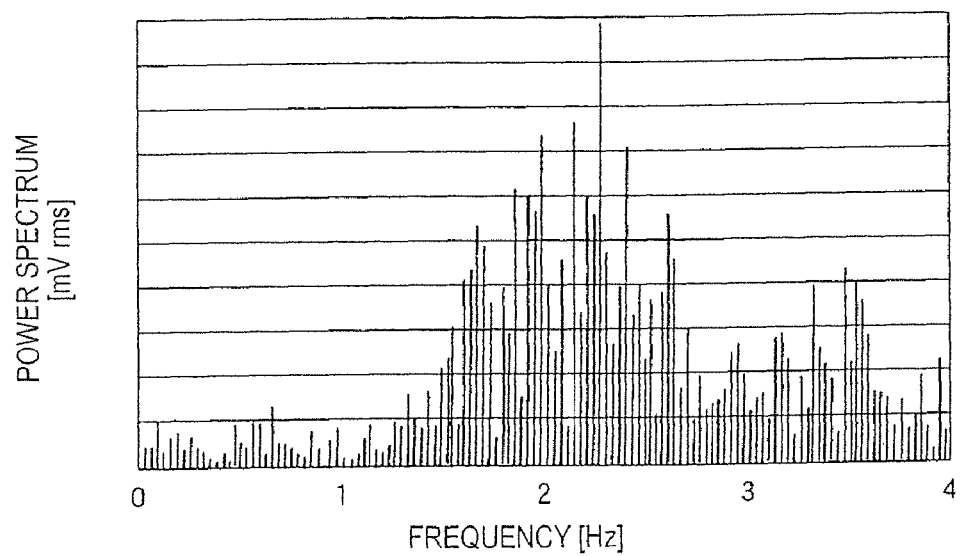
FIG. 26 shows the frequency analysis results obtained by subjecting the Y-axis acceleration data Ky in FIG. 25 to FFT.

FIG. 25 is a graph of a chronological arrangement of Y-axis acceleration data Ky for the Y-axis acceleration detection signal outputted from the Y-axis acceleration sensor 12Y. FIG. 26 shows the frequency analysis results obtained by subjecting the detected Y-axis acceleration data Ky in FIG. 25 to FFT.

Figure 27:
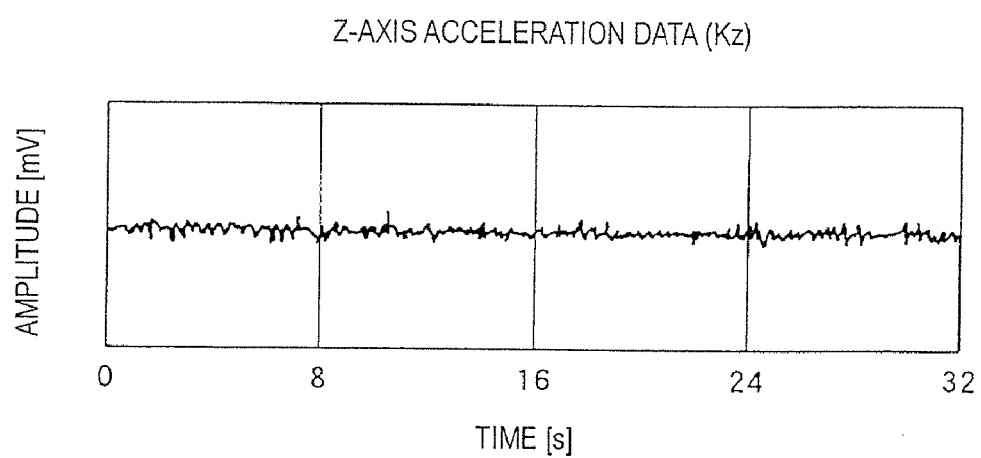
FIG. 27 is a graph of a chronological arrangement of Z-axis acceleration data Kz.
Figure 28:
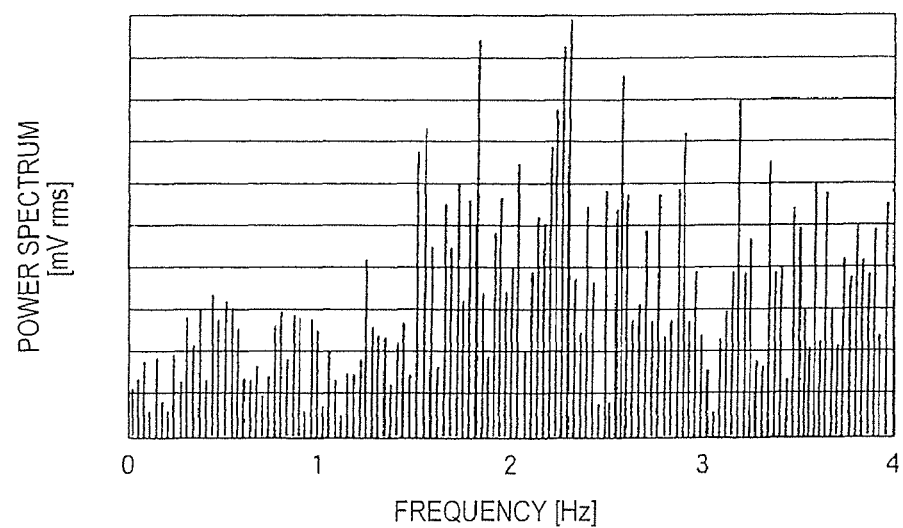
FIG. 28 shows the frequency analysis results obtained by subjecting the Z-axis acceleration data Kz in FIG. 27 to FFT.

FIG. 27 is a graph of a chronological arrangement of Z-axis acceleration data Kz for the Z-axis acceleration detection signal outputted from the Z-axis acceleration sensor 12Z. FIG. 28 shows the frequency analysis results obtained by subjecting the detected Z-axis acceleration data Kz in FIG. 27 to FFT.

Figure 29:
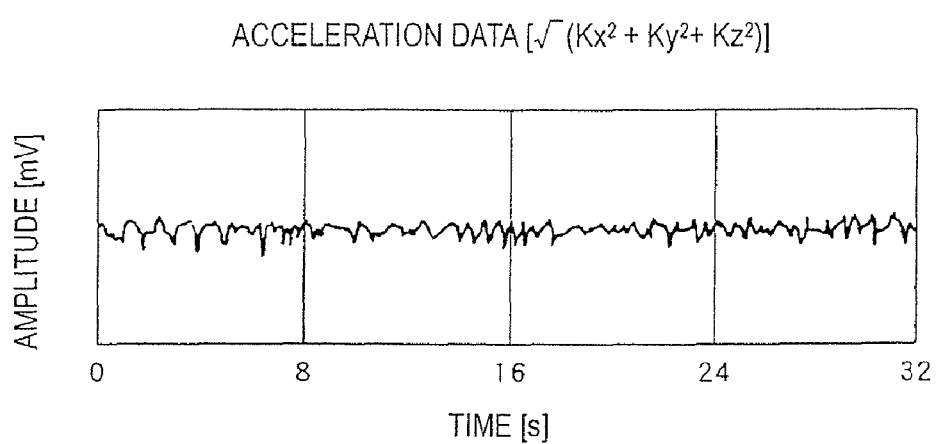
FIG. 29 is a graph of a chronological arrangement of combined acceleration vector data ($=\sqrt{(Kx^2+Ky^2+Kz^2)}$)
Figure 30:
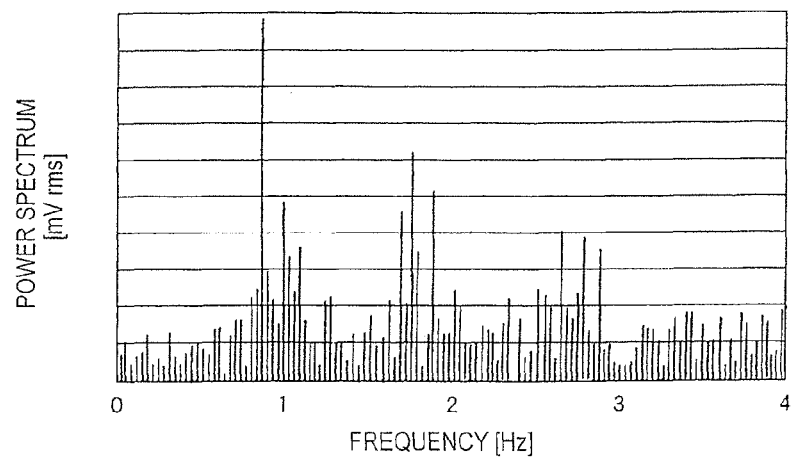
FIG. 30 shows the frequency analysis results obtained by subjecting the combined acceleration vector data ($=\sqrt{(Kx^2+Ky^2+Kz^2)}$) to FFT.

FIG. 29 is a graph of a chronological arrangement of combined acceleration vector data ($=\sqrt{(Kx^2+Ky^2+Kz^2)}$) obtained as a combined acceleration vector by treating the X-axis acceleration data Kx outputted from the X-axis acceleration sensor 12X, the Y-axis acceleration data Ky corresponding to the Y-axis acceleration detection signal outputted from the Y-axis acceleration sensor 12Y, and the Z-axis acceleration data Kz for the Z-axis acceleration detection signal outputted from the Z-axis acceleration sensor 12Z as vectors. FIG. 30 shows the frequency analysis results obtained by subjecting the combined acceleration vector data ($=\sqrt{(Kx^2+Ky^2+Kz^2)}$) in FIG. 29 to FFT.

Figure 31:
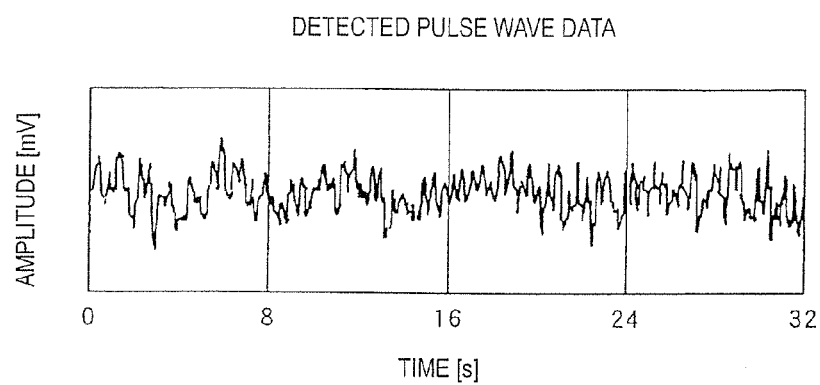
FIG. 31 is a graph of a chronological arrangement of one example of detected pulse wave data.
Figure 32:
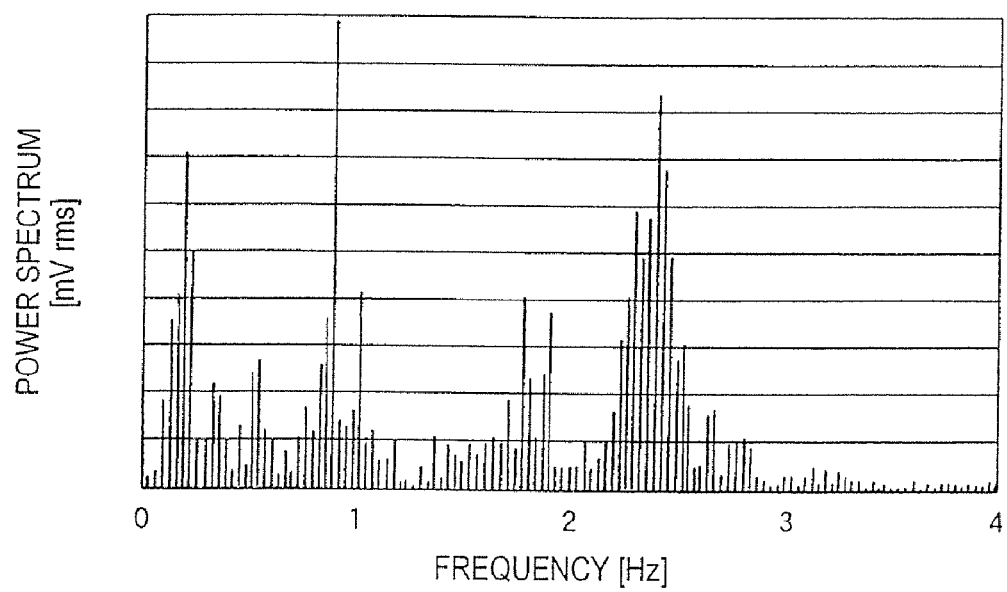
FIG. 32 shows the frequency analysis results obtained by subjecting the detected pulse wave data in FIG. 31 to FFT.

FIG. 31 is a graph of a chronological arrangement of one example of the detected pulse wave data. FIG. 32 shows the frequency analysis results obtained by subjecting the detected pulse wave data in FIG. 31 to FFT.

First, the MPU 24 sequentially reads the detected pulse wave data, the detected X-axis acceleration data, the detected Y-axis acceleration data, and the detected Z-axis acceleration data stored in the RAM 25, and outputs the detected pulse wave data in a single sampling period to the synthesizer 43.

In parallel with this, the MPU 24 outputs the detected X-axis acceleration data Kx, the detected Y-axis acceleration data Ky, and the detected Z-axis acceleration data Kz corresponding to the detected pulse wave data outputted to the synthesizer 43 to the integrator 42.

The integrator 42 multiplies the combined acceleration vector data ($=\sqrt{(Kx^2+Ky^2+Kz^2)}$), which is a combination of the following three types of acceleration data: the X-axis acceleration data, the Y-axis acceleration data, and the Z-axis acceleration data, by a simulated low-frequency signal such as the one shown in FIGS. 14 and 15; and outputs the result to the filter coefficient generating section 41.

Thus, the filter coefficient generating section 41 generates the adaptive filter coefficient h based on the previously outputted data by the synthesizer 43 to which the filter has been applied.

The filter coefficient generating section 41 then applies the adaptive filter coefficient h to the inputted combined acceleration vector data ($=\sqrt{(Kx^2+Ky^2+Kz^2)}$), generates body motion removal data $h(Kx^2+Ky^2+Kz^2)$, and outputs the result to the synthesizer 43.

Thus, the synthesizer 43 combines the current pulse wave data with the body motion removal data $h(Kx^2+Ky^2+Kz^2)$, substantially removes (subtracts) the body motion components contained in the current detected pulse wave data, extracts the pulse wave components, and outputs the residual data, which is the data to which the adaptive filter has been applied.

Figure 33:
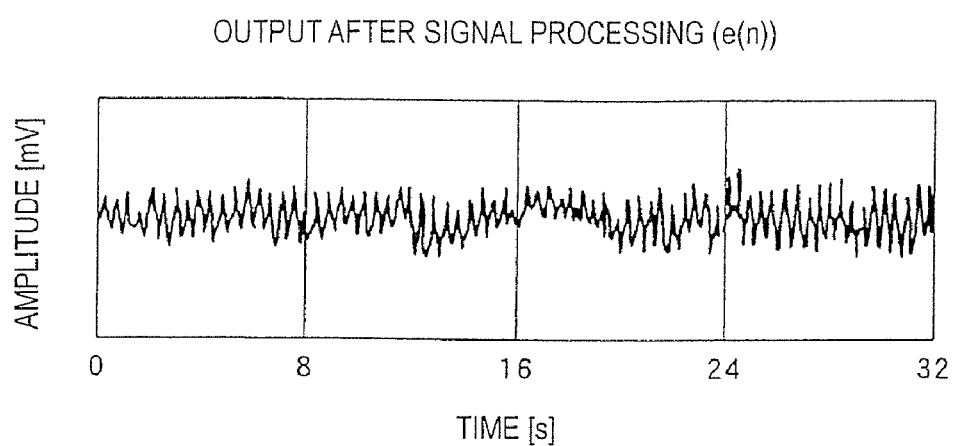
FIG. 33 is a graph of a chronological arrangement of residual data obtained by combining the data obtained by applying an adaptive filter to the combined acceleration vector data in FIG. 29 and the simulated low-frequency signal in FIG. 14 for the detected pulse wave data in FIG. 31.

FIG. 33 is a graph of a chronological arrangement of the residual data obtained by combining the data obtained by applying an adaptive filter to the combined acceleration vector data in FIG. 29 and the simulated low-frequency signal in FIG. 14 for the detected pulse wave data in FIG. 31.

Next, the MPU 24 subjects the residual data to FFT.

Figure 34:
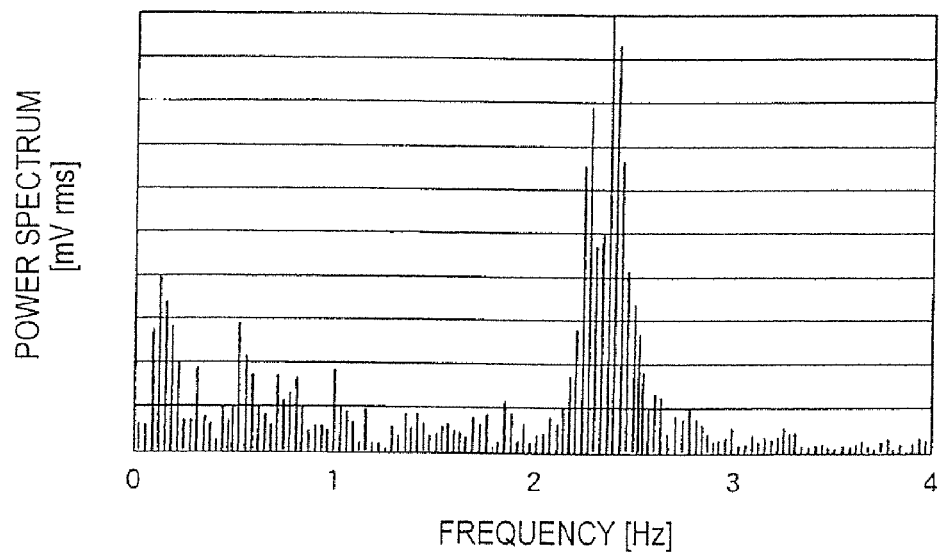
FIG. 34 shows the frequency analysis results obtained by subjecting the residual data in FIG. 33 to FFT.

FIG. 34 shows the frequency analysis results obtained by subjecting the residual data in FIG. 33 to FFT.

Thus, the frequency analysis results thus obtained retain spectra unrelated to the pulse wave components in a lower frequency range (<0.5 Hz) in comparison with the first embodiment, but they do not have any effect on the frequency band of the pulse wave components (2 Hz to 2.5 Hz). Therefore, the results have the body motion components originating in the veins substantially removed from the output signal of the pulse wave sensor (pulse wave components+body motion components), or, specifically, the results constitute pulse wave data corresponding primarily to the pulse wave components.

(1.2) Second Alternative of the First Embodiment

A pulse measurement device in a second alternative of the first embodiment is similar to the first embodiment, except that the use of a simulated low-frequency signal in the first embodiment is avoided in order to simplify the process and the device configuration, and that the use of combined acceleration vector data obtained by combining the Y-axis acceleration data and the Z-axis acceleration data is avoided as well. Therefore, the configuration in the second alternative of the first embodiment is essentially the same as the configuration of the pulse measurement device 10 shown in FIGS. 2 through 4, except that the MPU 24 is configured with an adaptive filter 50 of the second alternative instead of being configured with the adaptive filter 30 of the first embodiment.

Figure 35:
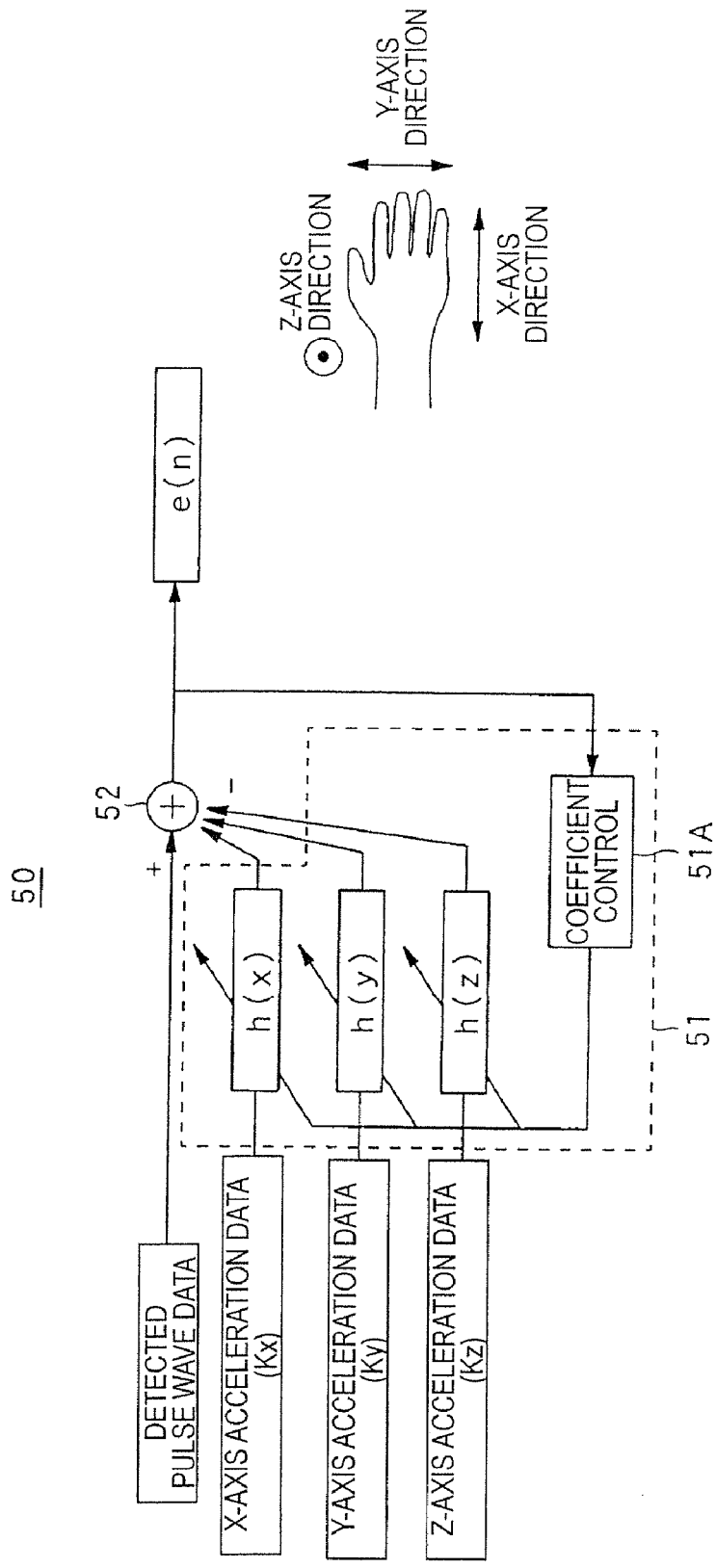
FIG. 35 is a schematic structural block diagram of one example of an adaptive filter according to a second alternative of the first embodiment.

FIG. 35 is a schematic structural block diagram of one example of an adaptive filter 50 according to the second alternative of the first embodiment. In general terms, the adaptive filter 50 has a filter coefficient generating section 51 and a synthesizer 52.

A coefficient controller 51A of the filter coefficient generating section 51 functions as a body motion component removing section and generates the adaptive filter coefficient h based on the data previously outputted from the synthesizer 52 to which the adaptive filter has been applied.

The filter coefficient generating section 51 applies the adaptive filter coefficient h generated by the coefficient controller 51A to the X-axis acceleration data Kx, the Y-axis acceleration data Ky, and the Z-axis acceleration data Kz, which are the inputted body motion component detection signals; generates body motion removal data h(x), h(y), and h(z); and outputs the result to the synthesizer 52.

The synthesizer 52 functions as a removal processing section; combines the extracted detected pulse wave data (=pulse wave components+body motion components) with the body motion removal data h(x), h(y), and h(z); substantially removes (subtracts) the body motion components contained in the current detected pulse wave data; and extracts the pulse wave components e(n).

An example of specific processed data will now be described.

Figure 36:
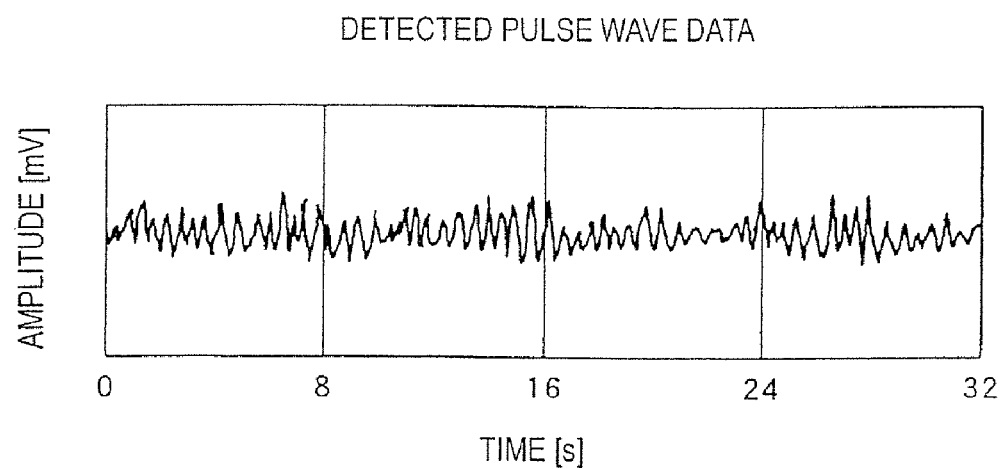
FIG. 36 is a graph of a chronological arrangement of one example of detected pulse wave data.
Figure 37:
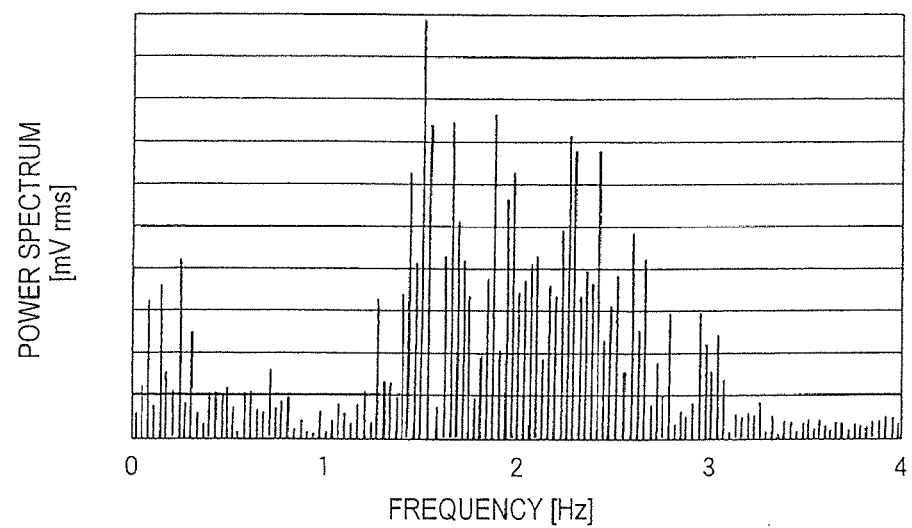
FIG. 37 shows the frequency analysis results obtained by subjecting the detected pulse wave data in FIG. 36 to FFT.

FIG. 36 is a graph of a chronological arrangement of one example of detected pulse wave data. FIG. 37 shows the frequency analysis results obtained by subjecting the detected pulse wave data in FIG. 36 to FFT.

Figure 38:
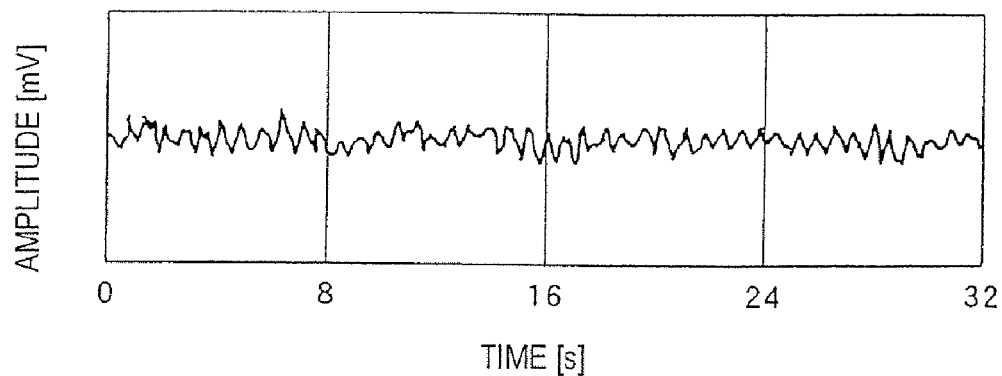
FIG. 38 is a graph of a chronological arrangement of residual data obtained by combining the signals obtained by applying an adaptive filter to the combined acceleration vector signal in FIG. 29 and the simulated low-frequency signal in FIG. 14 for the detected pulse wave data in FIG. 31.
Figure 39:
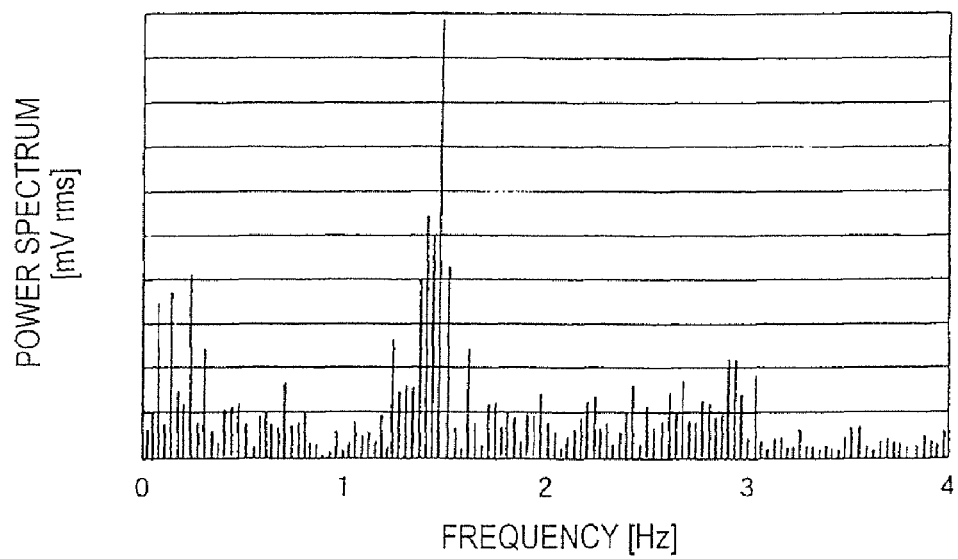
FIG. 39 shows the frequency analysis results obtained by subjecting the residual data in FIG. 38 to FFT.

FIG. 38 is a graph of a chronological arrangement of residual data obtained by combining the signals obtained by applying an adaptive filter to the combined acceleration vector signal in FIG. 29 and the simulated low-frequency signal in FIG. 14 for the detected pulse wave data in FIG. 31. FIG. 39 shows the frequency analysis results obtained by subjecting the residual data in FIG. 38 to FFT.

The MPU 24 subjects the residual data e(n) to FFT, whereby, as shown in FIG. 34, the frequency analysis results thus obtained have the body motion components originating in the veins substantially removed from the output signal of the pulse wave sensor (pulse wave components+body motion components) similar to the first embodiment, or, specifically, the results constitute pulse wave data corresponding primarily to the pulse wave components. Also, in the second alternative of the first embodiment, the process and device configuration can be simplified because a simulated low-frequency signal is not used for processing.

(1.3) Third Alternative of the First Embodiment

A third alternative of the first embodiment is similar to the first alternative of the first embodiment except for dispensing with the use of a simulated low-frequency signal to conduct processing in the first alternative of the first embodiment (1.1). Therefore, the configuration in the third alternative of the first embodiment is essentially the same as the configuration of the pulse measurement device 10 shown in FIGS. 2 through 4, except that the MPU 24 is configured with an adaptive filter 60 of the third alternative instead of being configured with the adaptive filter 30 of the first embodiment.

Figure 40:
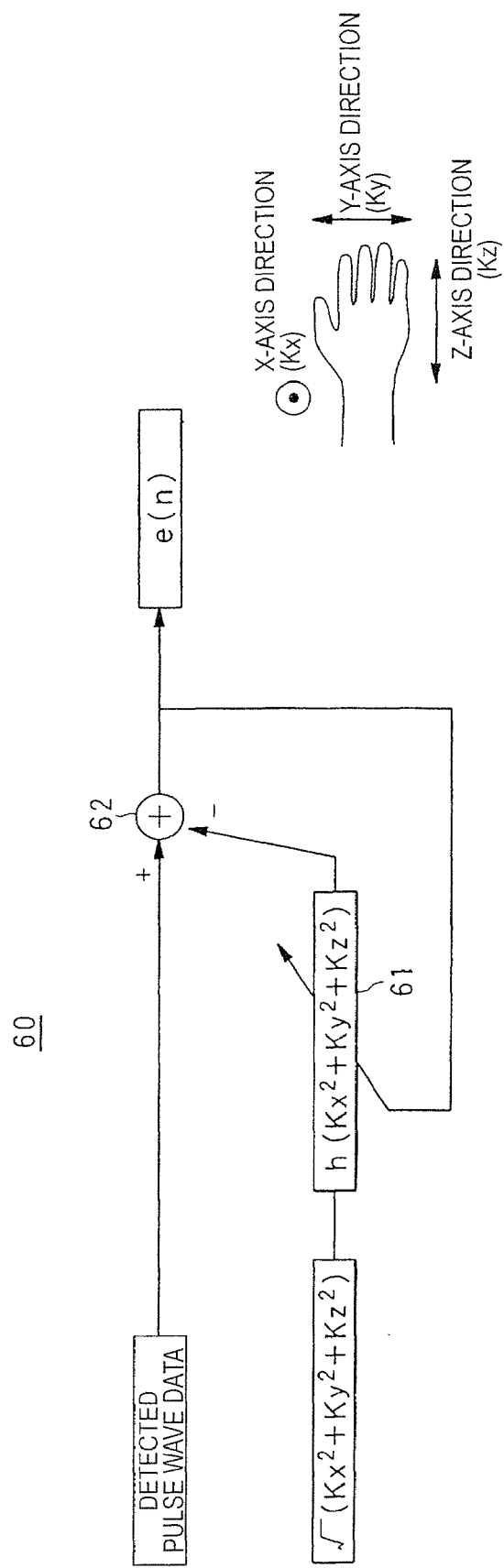
FIG. 40 is a schematic structural block diagram of one example of an adaptive filter according to a third alternative of the first embodiment.

FIG. 40 is a schematic structural block diagram of one example of the adaptive filter 60 according to the third alternative of the first embodiment. In general terms, the adaptive filter 60 has a filter coefficient generating section 61 and a synthesizer 62.

The filter coefficient generating section 61 functions as a body motion component removing section that generates the adaptive filter coefficient h based on the data previously outputted from the synthesizer 62 to which the adaptive filter has been applied. Furthermore, the filter coefficient generating section 61 applies the adaptive filter coefficient h generated by the combined acceleration vector data (= $\sqrt{(Kx^2+Ky^2+Kz^2)}$), which is a combination the following three types of acceleration data: the X-axis acceleration data Kx, the Y-axis acceleration data Ky, and the Z-axis acceleration data Kz; generates body motion removal data h($Kx^2+Ky^2+Kz^2$); and outputs the result to the synthesizer 62.

The synthesizer 62 functions as a removal processing section; combines the extracted detected pulse wave data (=pulse wave components+body motion components) with the body motion removal data h($Kx^2+Ky^2+Kz^2$); substantially removes (subtracts) the body motion components contained in the current detected pulse wave data; and extracts the pulse wave components e(n).

According to the third alternative of the first embodiment, it is possible to obtain the same effects as in the first alternative of the first embodiment, and it is also possible to further simplify the device structure and the processing because a simulated low-frequency signal is not used.

(1.4) Fourth Alternative of the First Embodiment

A fourth alternative of the first embodiment is similar to the first embodiment, except for dispensing with use of a simulated low-frequency signal to conduct processing in the first embodiment. Therefore, the configuration in the fourth alternative of the first embodiment is essentially the same as the configuration of the pulse measurement device 10 shown in FIGS. 2 through 4, except that the MPU 24 is configured with an adaptive filter 70 of the fourth alternative instead of being configured with the adaptive filter 30 of the first embodiment.

Figure 41:
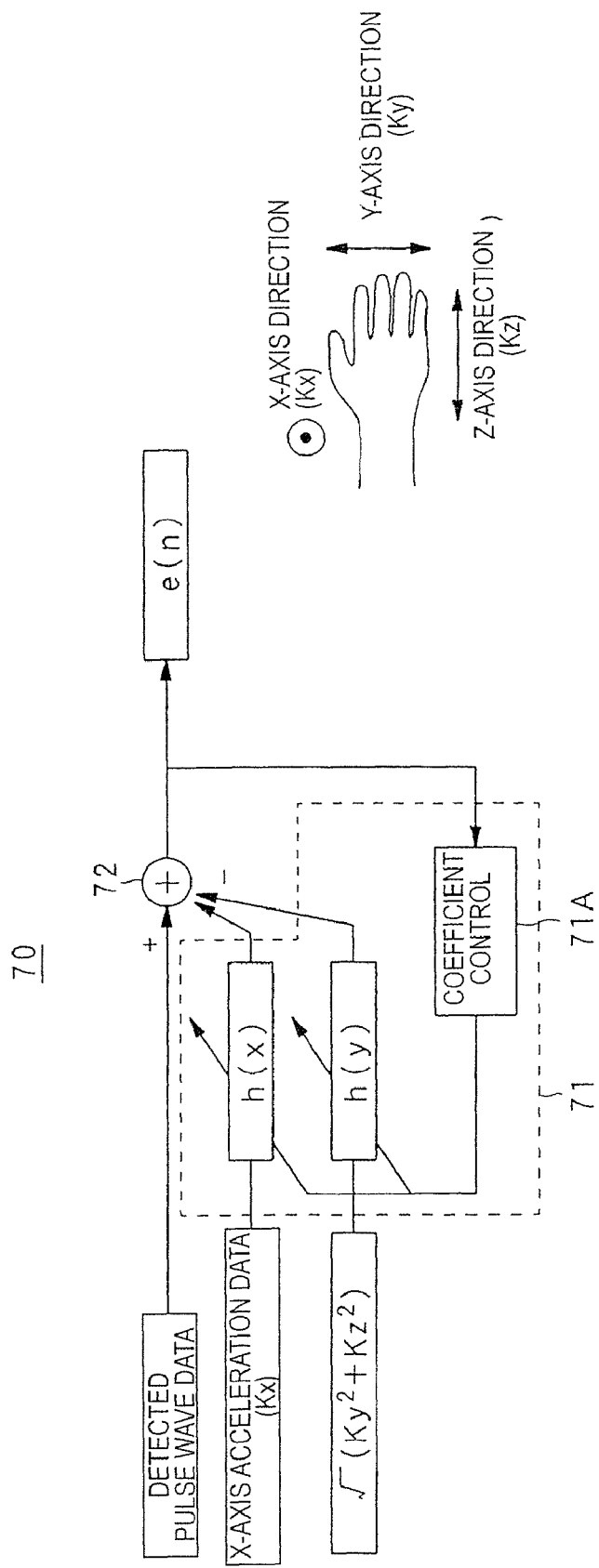
FIG. 41 is a schematic structural block diagram of one example of an adaptive filter according to a fourth alternative of the first embodiment.

FIG. 41 is a schematic structural block diagram of one example of the adaptive filter 70 according to the first embodiment. In general terms, the adaptive filter 70 has a filter coefficient generating section 71 and a synthesizer 72.

A coefficient controller 71A of the filter coefficient generating section 71 functions as a body motion component removing section that generates the adaptive filter coefficient h based on the data previously outputted from the synthesizer 72 to which the adaptive filter has been applied. The filter coefficient generating section 71 applies the adaptive filter coefficient h generated by the coefficient controller 71A to the detected X-axis acceleration data Kx (=x) and to the combined acceleration vector data (=y) consisting of the combined data from the Y-axis acceleration data Ky and the Z-axis acceleration data Kz, which are the inputted body motion component detection signals; generates body motion removal data h(x), h(y), and h(z); and outputs the result to the synthesizer 72.

The synthesizer 72 functions as a removal processing section; combines the extracted detected pulse wave data (=pulse wave components+body motion components) with the body motion removal data h(x), h(y), and h(z); substantially removes (subtracts) the body motion components contained in the current detected pulse wave data; and extracts the pulse wave components e(n).

According to the fourth alternative of the first embodiment, it is possible to obtain the same effects as in the first embodiment, and it is also possible to further simplify the device structure and the processing because a simulated low-frequency signal is not used.

In the first embodiment and in the first alternative and the third through fifth alternatives of the first embodiment, no weighting was done when calculating the combined acceleration vector data (= $\sqrt{(Kx^2+Ky^2+Kz^2)}$), which is a combination of the following three types of acceleration data: the X-axis acceleration data Kx, the Y-axis acceleration data Ky, and the Z-axis acceleration data Kz, or when calculating the combined acceleration vector data (= $\sqrt{Ky^2+Kz^2}$), which is a combination of the following two types of acceleration data: the Y-axis acceleration data Ky and the Z-axis acceleration data Kz; but it is also possible to use a configuration such that the acceleration data constituting the basis of all the combined acceleration vector data is suitably weighted.

For example, the following formula can be used when determining the combined acceleration vector data from the following three types of acceleration data: the X-axis acceleration data Kx, the Y-axis acceleration data Ky, and the Z-axis acceleration data Kz.

$$\sqrt{(a \cdot Kx^2 + b \cdot Ky^2 + cKz^2)}; \text{ wherein } a > b \geq c > 0.$$

Also, the X-axis acceleration data Kx, the Y-axis acceleration data Ky, and the Z-axis acceleration data Kz may similarly be suitably weighted and the adaptive filter coefficient may be applied thereto even when the combined acceleration vector data is not used, as in the second alternative of the first embodiment.

Furthermore, the simulated low-frequency signal may also be weighted.

Furthermore, as shown in FIG. 2, in the above descriptions, the case of fitting the triaxial acceleration sensor 12 on the arm was described, but it is also possible to mount the sensor on the base of the fingers or the fingertips.

(2) Second Embodiment

A pulse measurement device 80 according to a second embodiment of the present invention will now be described with reference to FIGS. 42 through 60. The main difference between the second embodiment and the first embodiment is that the body motion components are measured in the second embodiment using a pressure sensor instead of the triaxial acceleration sensor of the first embodiment. Otherwise the basic configuration is similar to the first embodiment; therefore, in view of the similarity between the first embodiment and the second embodiment, descriptions of the parts of the second embodiment with identical or similar functions to the parts of the first embodiment are omitted for the sake of simplicity.

First, the operating principle of the second embodiment will be described prior to a detailed description of the second embodiment.

The output of the pulse wave sensor for detecting pulse waves includes various body motion components in addition to pulse wave components. It is known that these body motion components are generated by changes in the body originating in the movements (walking/running, arm movement, and the like) of the user whose pulse is to be measured. Therefore, it is possible to detect the movements of the user when an acceleration sensor is used as the sensor for detecting body motion components, but the body motion components contained in the output of the pulse wave sensor are generated by changes in the body originating from these movements, and it is difficult to accurately detect the true body motion components contained in the output of the pulse wave sensor.

The effect of venous blood as a body motion component generated in the body cannot be ignored because this component has the greatest effect on an optical sensor used as a pulse wave sensor.

It is known that since the vein walls are highly extensible, they are stretched out when blood pressure increases, large quantities of blood accumulate in these sections, and this process is accompanied by an increase of pressure on the body surface along with the stretching of the veins. The inventors have accordingly researched the relationship between the amount of change in pressure on the body surface and the amount of body motion components (amount of stroke components) included in the pulse wave sensor when the same body motion components are generated.

Figure 42:
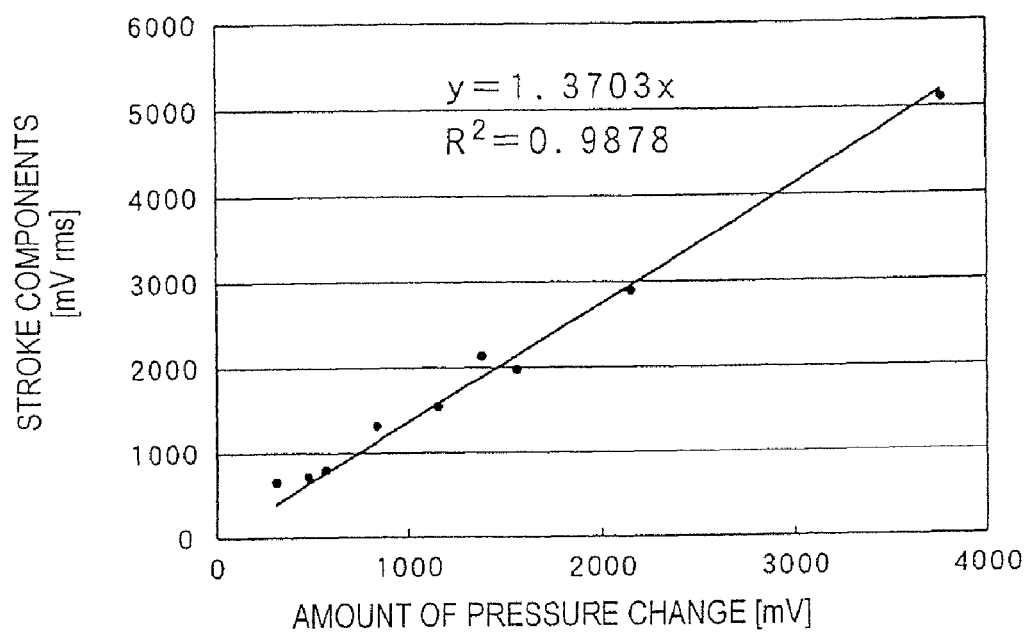
FIG. 42 is an explanatory diagram of the relationship between the amount of change in pressure and the amount of body motion components (amount of stroke components) included in the pulse wave sensor output.

FIG. 42 is an explanatory diagram of the relationship between the amount of change in pressure and the amount of body motion components (amount of stroke components) included in the pulse wave sensor output. As shown in FIG. 42, it is clear that the amount of change in pressure and the amount of body motion components (amount of stroke components) included in the pulse wave sensor output have an essentially proportional relationship. In other words, it is possible to surmise the effect of the venous blood included in the output of the pulse wave sensor if the amount of change in pressure in the body surface can be detected.

In view of this, in the second embodiment, the pulse rate is accurately detected based on a signal from which the effect of venous blood has been removed by detecting the stretching of the veins, or, specifically, the body motion components originating in the veins with an external pressure sensor, and subtracting them from the pulse wave sensor output at a specific rate.

Figure 43:
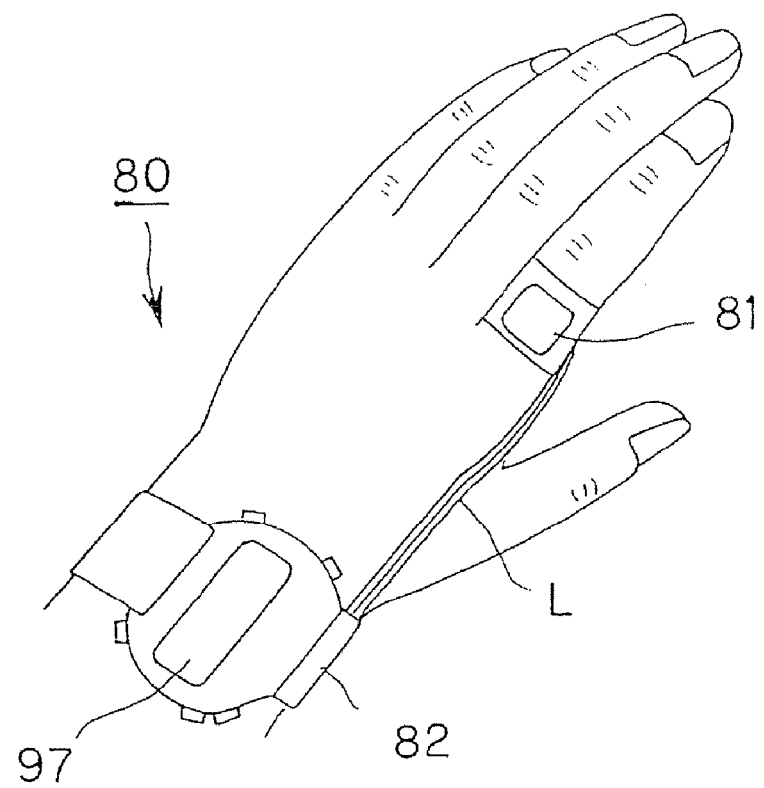
FIG. 43 is a schematic structural diagram of a pulse measurement device of the second embodiment.

The second embodiment will now be described in detail. FIG. 43 is a schematic structural diagram of a pulse measurement device 80 of the second embodiment. In general terms, the pulse measurement device 80 has a sensor module 81 mounted on the finger of the user, and a device main body 82 connected to the sensor module 81 via a wiring L and mounted on the arm of the user.

Figure 44:
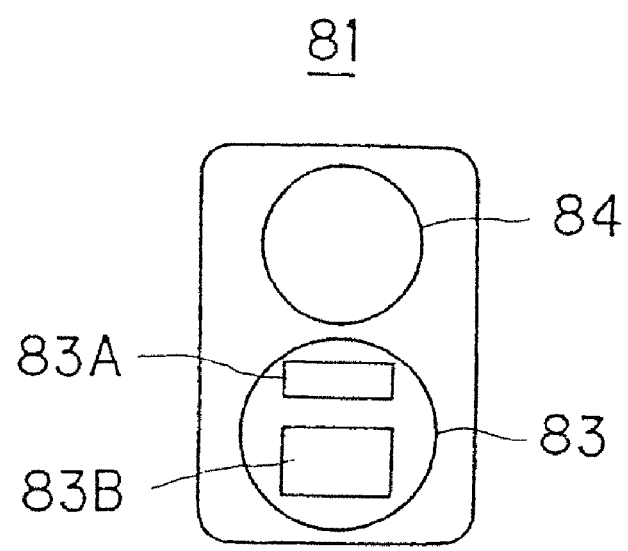
FIG. 44 is an explanatory diagram of the arrangement of sensors in the sensor module of the pulse measurement device of the second embodiment.

FIG. 44 is an explanatory diagram of the arrangement of sensors in the sensor module 81. In general terms, the sensor module 81 is configured with a pulse wave sensor 83 for primarily detecting pulse wave components and a pressure sensor 84 for primarily detecting body motion components.

The pulse wave sensor 83 has an LED 83A for emitting detection light and a PD (Photo Detector) 83B for receiving the detection light reflected by the body.

Figure 45:
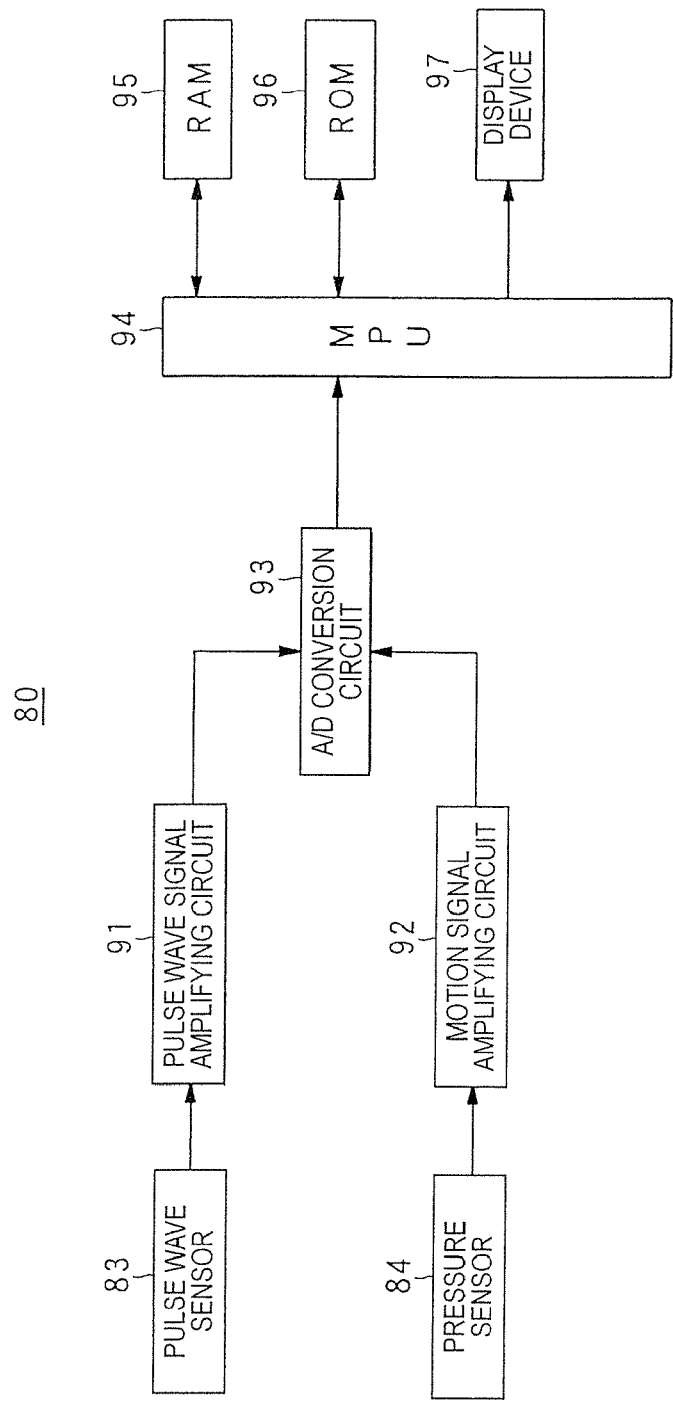
FIG. 45 is a schematic structural block diagram of the pulse measurement device of the second embodiment.

FIG. 45 is a schematic structural block diagram of the pulse measurement device 80. In general terms, the pulse measurement device 80 has a pulse wave signal amplifying circuit 91, a body motion signal amplifying circuit 92, an A/D conversion circuit 93, an MPU 94, a RAM 95, a ROM 96, and a liquid crystal display device or other such display device 97 in addition to the pulse wave sensor 83 and the pressure sensor 84 previously described. As described above, the pressure sensor 84 is used as the body motion sensor in the second embodiment.

The pulse wave signal amplifying circuit 91 amplifies the pulse wave detection signal outputted from the pulse wave sensor 83 at a prescribed rate of amplification, and outputs the result to the A/D conversion circuit 93 as an amplified pulse wave detection signal.

The body motion signal amplifying circuit 92 amplifies the pressure detection signal outputted from the pressure sensor 84 at a prescribed rate of amplification, and outputs the result to the A/D conversion circuit 93 as an amplified pressure detection signal.

The A/D conversion circuit 93 performs analog/digital conversion separately on the inputted amplified pulse wave detection signal and the amplified pressure detection signal, and outputs the result to the MPU 94 as detected pulse wave data and detected pressure data.

The MPU 94 stores the detected pulse wave data and the detected pressure data (detected body motion data) in the RAM 95, calculates the pulse rate based on a control program stored in the ROM 96, and displays the result on the display device 97. More specifically, the MPU 94 chronologically arranges the detected pulse wave data and the detected pressure data (detected body motion data) stored in the RAM 95, and determines the differential data, which is the difference between the detected pulse wave data and the detected pressure data, for each corresponding sampling time.

Frequency analysis (FFT: Fast Fourier Transformation) is then performed on the differential data, the harmonic components of the pulse wave are extracted, and the pulse rate is calculated from the frequency.

A more specific pulse rate calculation process will now be described.

Figure 46:
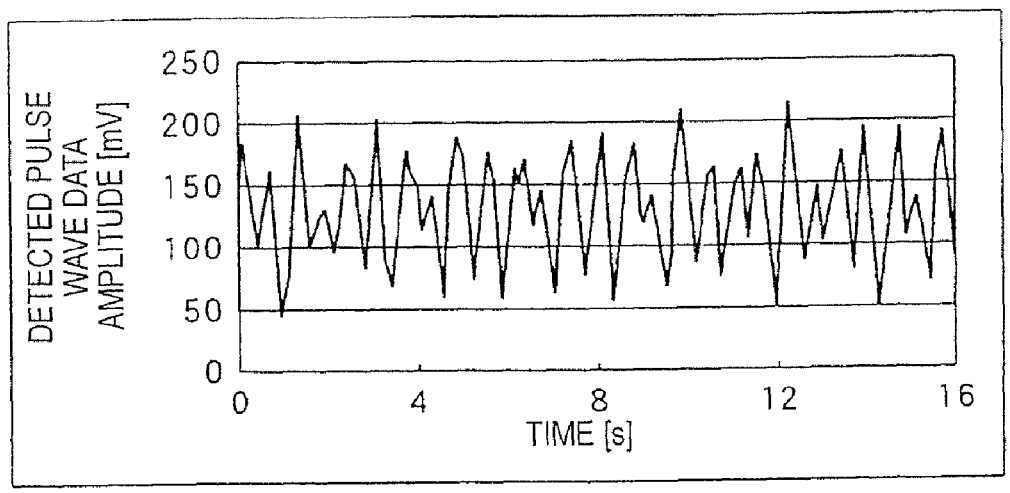
FIG. 46 is a graph of a chronological arrangement of one example of detected pulse wave data.
Figure 47:
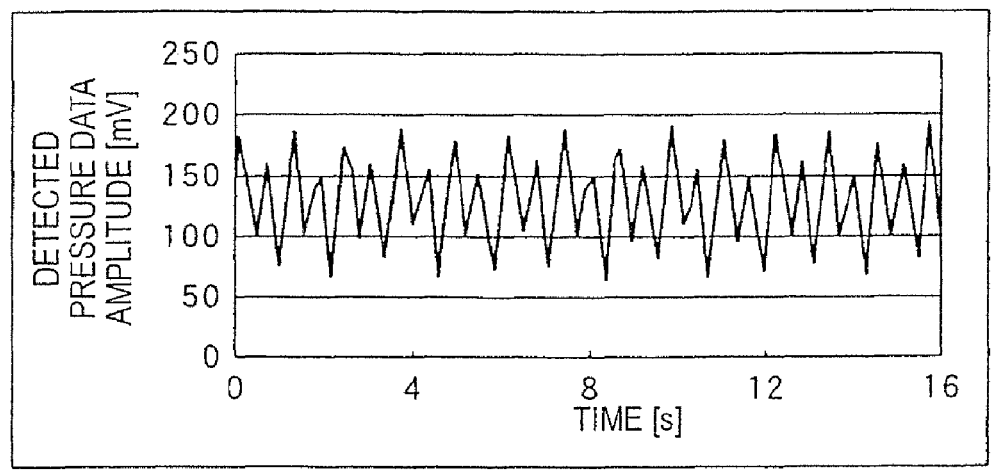
FIG. 47 is a graph in which detected pressure data correlated with the detected pulse wave data in FIG. 46 is chronologically arranged along the same time axis.

FIG. 46 is a graph of a chronological arrangement of one example of detected pulse wave data. FIG. 47 is a graph in which detected pressure data correlated with the detected pulse wave data in FIG. 46 is chronologically arranged along the same time axis.

First, the MPU 94 sequentially reads out the detected pulse wave data and the detected pressure data stored in the RAM 95 and calculates the differential data by subtracting the detected pressure data in a certain sampling period from the detected pulse wave data for the same sampling timing.

Figure 48:
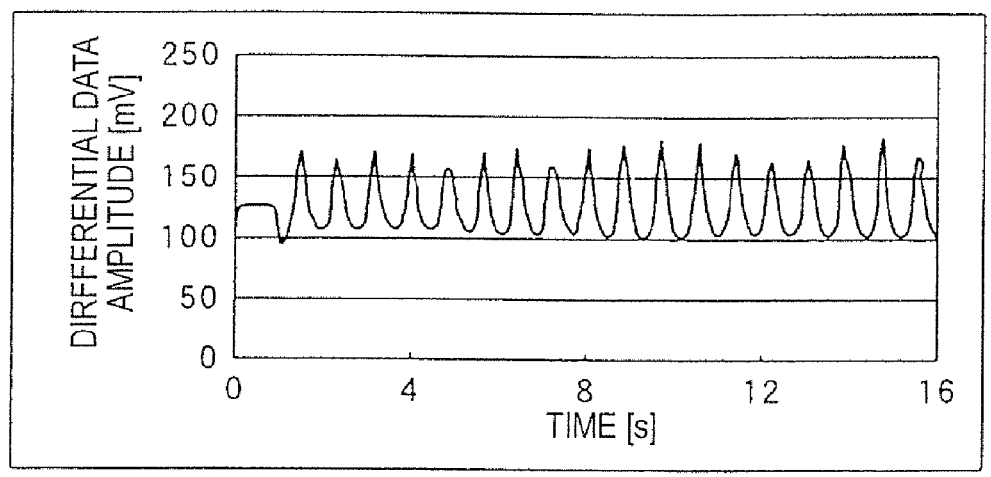
FIG. 48 is a graph of a chronological arrangement of differential data calculated from the detected pulse wave data in FIG. 46 and the detected pressure data in FIG. 6.

FIG. 48 is a graph of a chronological arrangement of differential data calculated from the detected pulse wave data in FIG. 46 and the detected pressure data in FIG. 47.

Next, the MPU 94 subjects the differential data to FFT.

Figure 49:
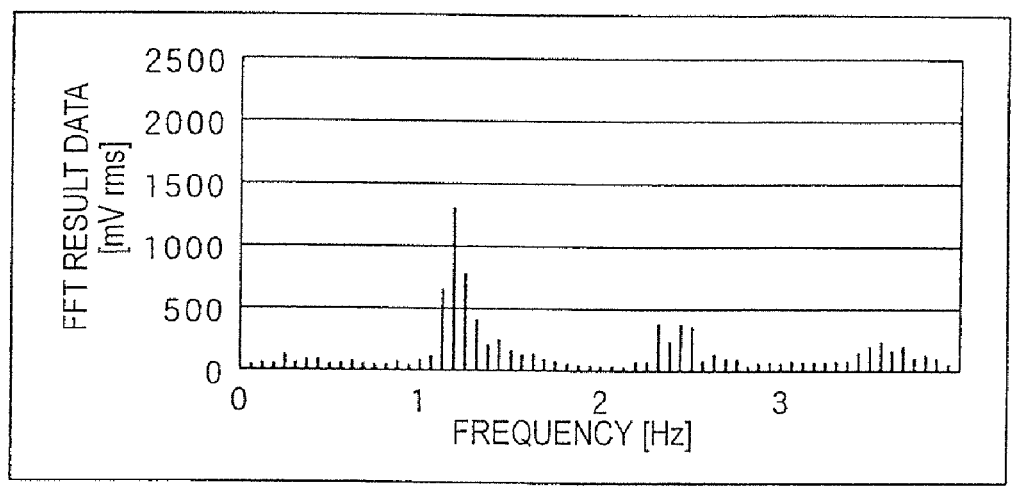
FIG. 49 shows the frequency analysis results obtained by subjecting the differential data in FIG. 48 to FFT.

FIG. 49 shows the frequency analysis results obtained by subjecting the differential data in FIG. 48 to FFT.

Thus, the frequency analysis results thus obtained have the body motion components originating in the veins substantially removed from the output signal (pulse wave components+body motion components) of the pulse wave sensor, and are, specifically, pulse wave data that primarily corresponds to the pulse wave components.

Furthermore, the MPU 94 calculates the pulse rate from the frequency on the assumption that the maximum frequency components of the resulting pulse wave data constitute the pulse spectrum.

The MPU 94 then displays the pulse rate on the display device 97.

As described above, according to the second embodiment, variation in the veins, which is the main factor in the body motion components generated in the body, can be accurately detected and registered by using a pressure sensor. Therefore, the body motion components can be accurately removed, making it possible to accurately detect pulse wave components, and hence to accurately measure the pulse rate.

(2.1) First Alternative of the Second Embodiment

A first alternative of the second embodiment is similar to the second embodiment, except that the second embodiment has a configuration in which the differential data is calculated by subtracting the detected pressure data from the detected pulse wave data prior to frequency analysis (FFT), while in the first alternative, the differential data is calculated after performing frequency analysis on the detected pulse wave data and the detected pressure data. Therefore, the configuration of the first alternative of the second embodiment is essentially the same as the configuration of the pulse measurement device 80 of the second embodiment shown in FIGS. 43 through 45.

In the first alternative of the second embodiment, the MPU 94 performs frequency analysis (FFT) on both the detected pulse wave data and the detected pressure data (detected body motion data) stored in the RAM 95. Therefore, the MPU 94 essentially constitutes a first frequency analyzing section and a second frequency analyzing section.

Next, the MPU 94 determines the differential data, which is the difference between the detected pulse wave data after analyzed for frequency and the detected pressure data after analyzed for frequency. The harmonic components of the pulse wave are then extracted from the resulting differential data, and the pulse rate is calculated from the frequency thereof.

A more specific pulse rate calculation process will now be described.

Figure 50:
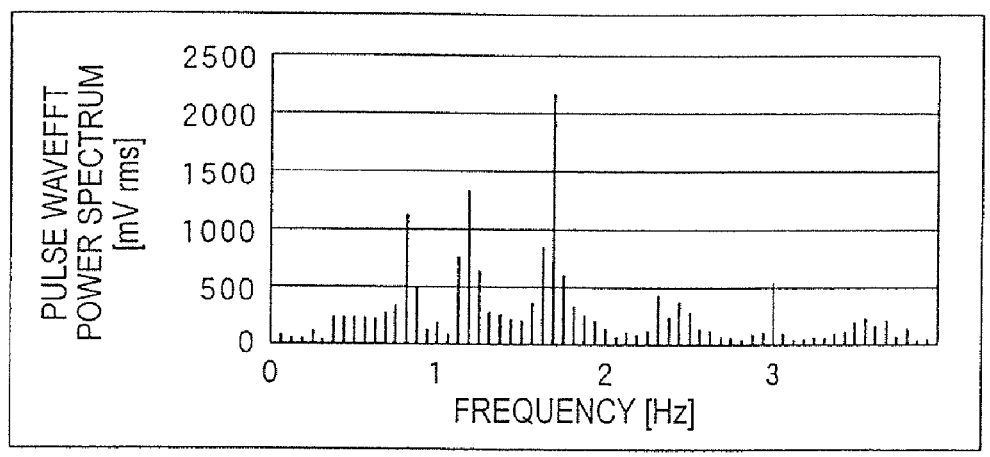
FIG. 50 is an explanatory diagram of the frequency analysis results of the detected pulse wave data according to a first alternative of the second embodiment.
Figure 51:
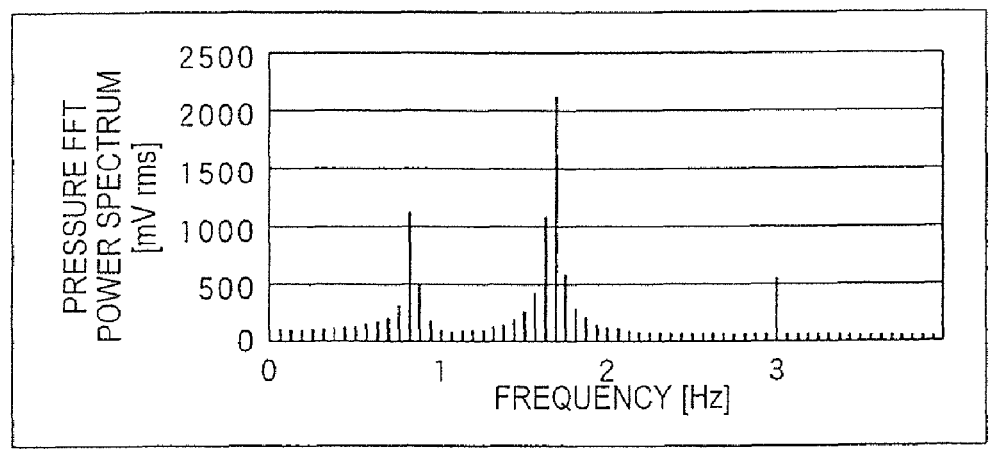
FIG. 51 is an explanatory diagram of the frequency analysis results of the detected pressure data according to the first alternative of the second embodiment.

FIG. 50 is an explanatory diagram of the frequency analysis results for detected pulse wave data. FIG. 51 is an explanatory diagram of the frequency analysis results for detected pressure data.

First, the MPU 94 sequentially reads out the detected pulse wave data and the detected pressure data stored in the RAM 95, and subjects them to FFT for frequency analysis.

Figure 52:
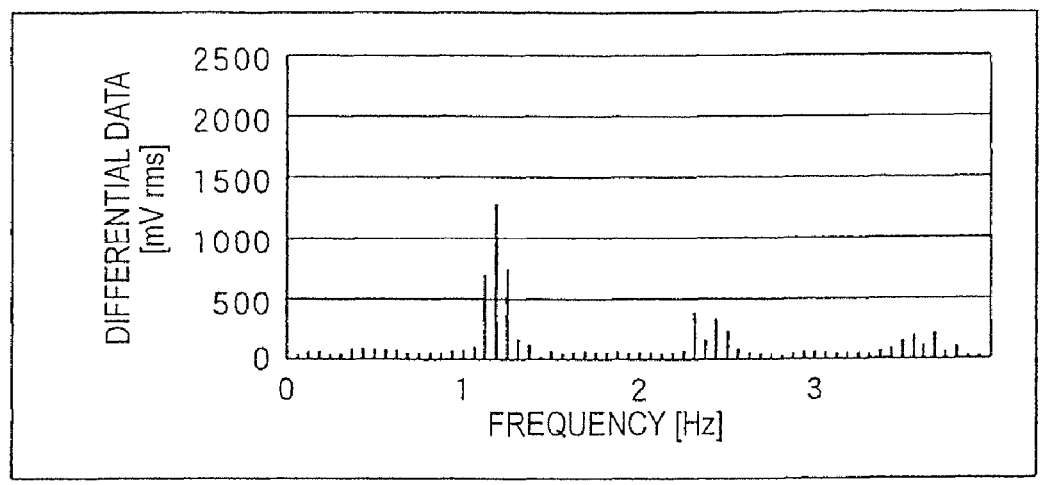
FIG. 52 is an explanatory diagram of differential data, which is the difference between the detected pulse wave data analyzed for frequency and the detected pressure data analyzed for frequency, according to the first alternative of the second embodiment.

FIG. 52 is an explanatory diagram of differential data, which is the difference between the detected pulse wave data after analyzed for frequency and the detected pressure data after analyzed for frequency.

Next, the MPU 94 compares the detected pulse wave data after analyzed for frequency with the detected pressure data after analyzed for frequency, and determines the difference between these frequency components to create the differential data.

Thus, the frequency analysis results as the differential data have the body motion components originating in the veins substantially removed from the output signal (pulse wave components+body motion components) of the pulse wave sensor, and are, specifically, pulse wave data that primarily corresponds to the pulse wave components.

Furthermore, the MPU 94 calculates the pulse rate from the frequency on the assumption that the maximum frequency components of the resulting pulse wave data constitute the pulse spectrum.

The MPU 94 then displays the pulse rate on the display device 97.

As described above, according to the first alternative of the second embodiment, variation in the veins, which is the main factor in the body motion components generated in the body, can be also accurately detected and registered. Therefore, the body motion components can be accurately removed, making it possible to accurately detect the pulse wave components, and hence to accurately measure the pulse rate.

(2.2) Second Alternative of the Second Embodiment

A second alternative of the second embodiment is similar to the second embodiment, except that the second embodiment has a configuration in which the differential data is calculated by subtracting the detected pressure data from the detected pulse wave data prior to frequency analysis (FFT), while in the second alternative, the MPU 94 is configured with an adaptive filter 100 and the body motion components are removed from the detected pulse wave data. Therefore, the second alternative of the second embodiment has the same configuration, except that the MPU 94 of the pulse measurement device 80 of the second embodiment is configured with an adaptive filter 100.

Figure 53:
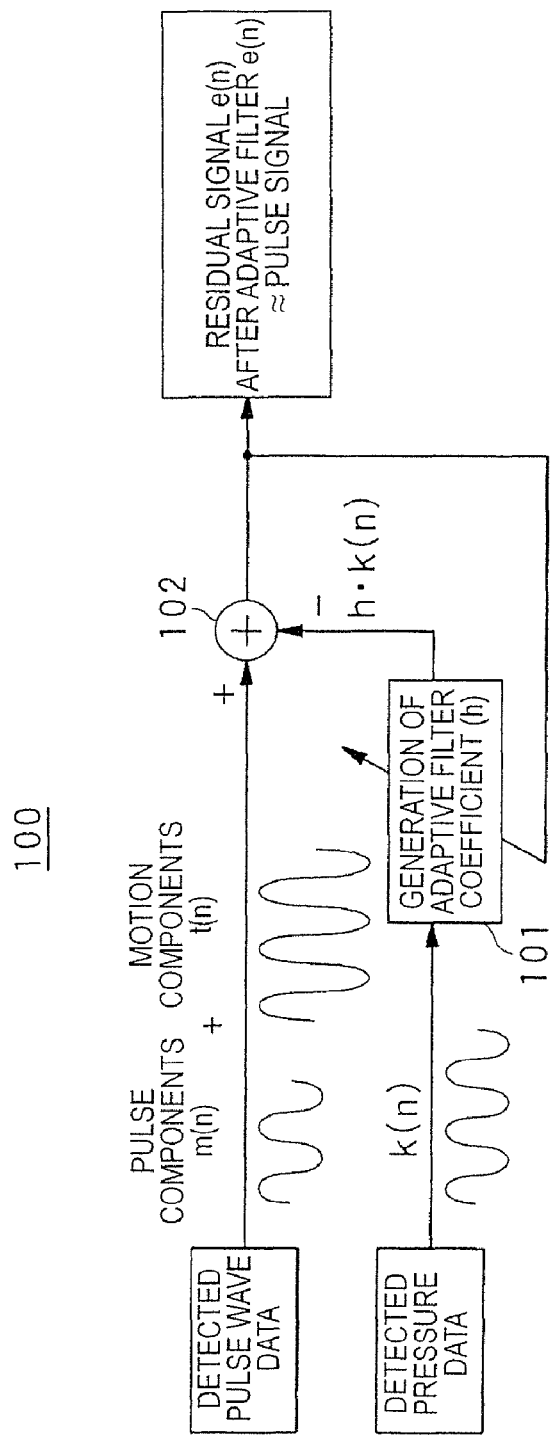
FIG. 53 shows a schematic structural block diagram of one example of the adaptive filter in accordance with a second alternative of the second embodiment.

FIG. 53 shows a schematic structural block diagram of one example of the adaptive filter 100. In general terms, the adaptive filter 100 has a filter coefficient generating section 101 and a synthesizer 102.

The filter coefficient generating section 101 functions as a body motion component removing section and generates the adaptive filter coefficient h based on data previously outputted by the synthesizer 102 to which the filter has been applied. The adaptive filter coefficient h is then applied to the detected pressure data (=k(n)), which functions as the inputted body motion component detection signal; body motion removal data (=h·k(n)) is generated; and this data is outputted to the synthesizer 102.

The synthesizer 102 functions as a removal processing section, combines the extracted detected pulse wave data (=pulse wave components+body motion components) and the body motion removal data, substantially removes (subtracts) the body motion components contained in the current detected pulse wave data, and extracts pulse wave components.

A more specific pulse rate calculation process according to the second alternative of the second embodiment will now be described.

Figure 54:
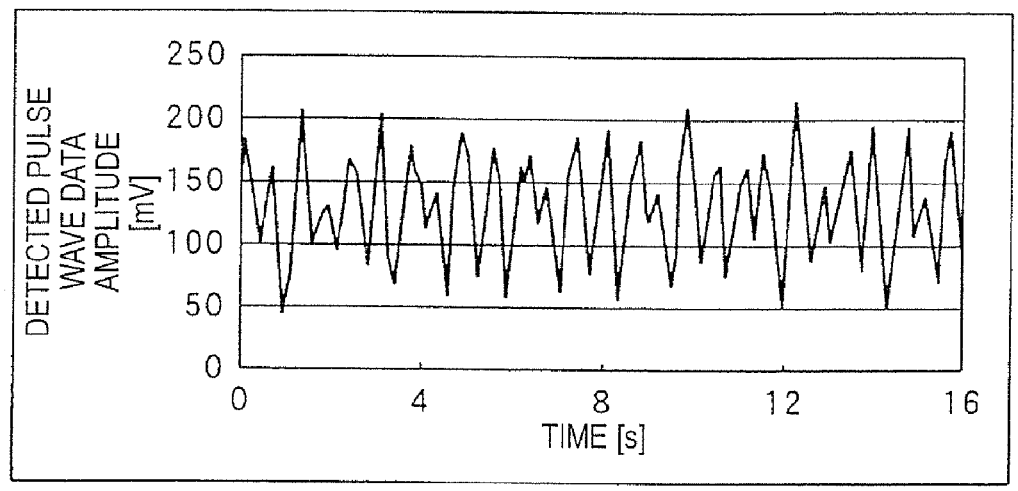
FIG. 54 is a graph of a chronological arrangement of an example of the detected pulse wave data according to the second alternative of the second embodiment.
Figure 55:
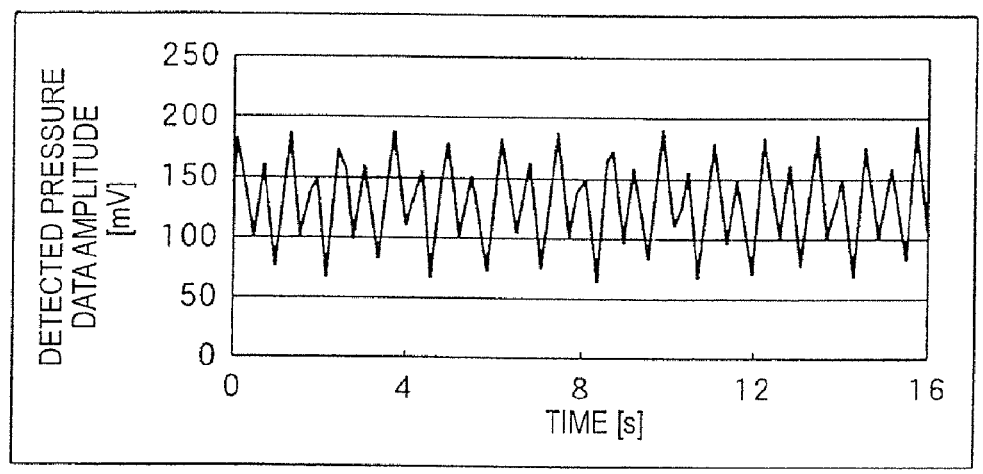
FIG. 55 is a graph in which detected pressure data correlated with the detected pulse wave data in FIG. 54 is chronologically arranged along the same time axis.

FIG. 54 is a graph of a chronological arrangement of an example of the detected pulse wave data. FIG. 55 is a graph in which detected pressure data correlated with the detected pulse wave data in FIG. 54 is chronologically arranged along the same time axis.

First, the MPU 94 sequentially reads out the detected pulse wave data and the detected pressure data stored in the RAM 95, and outputs the detected pulse wave data in a certain sampling period to the synthesizer 102.

Also, the MPU 94 presents the filter coefficient generating section 101 with detected pressure data that corresponds to the detected pulse wave data outputted to the synthesizer 102.

Thus, the filter coefficient generating section 101 creates an adaptive filter coefficient h based on the data previously outputted from the synthesizer 102 to which the adaptive filter has been applied. The adaptive filter coefficient h is then applied to the detected pressure data (=k(n)) functioning as the inputted body motion component detection signal, and body motion removal data (=h·k(n)) is outputted to the synthesizer 102.

Thus, the synthesizer 102 combines the current pulse wave data and the body motion removal data, substantially removes (subtracts) the body motion components contained in the current detected pulse wave data, extracts the pulse wave components, and outputs the residual data (=data to which the filter has been applied).

Figure 56:
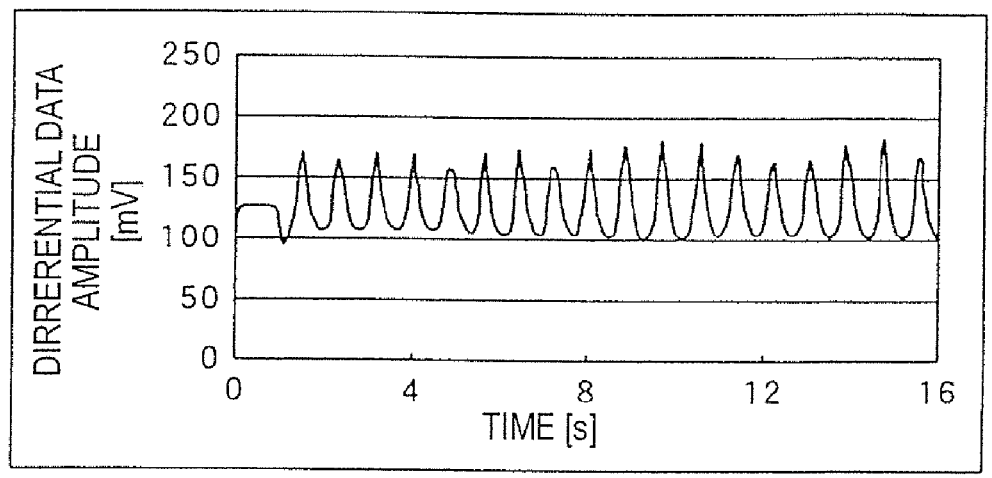
FIG. 56 is a graph of a chronological arrangement of residual data obtained by applying an adaptive filter to the detected pulse wave data in FIG. 54 and the detected pressure data in FIG. 55.

FIG. 56 is a graph of a chronological arrangement of residual data obtained by applying an adaptive filter to the detected pulse wave data in FIG. 54 and the detected pressure data in FIG. 55.

Next, the MPU 94 subjects the residual data to FFT.

Figure 57:
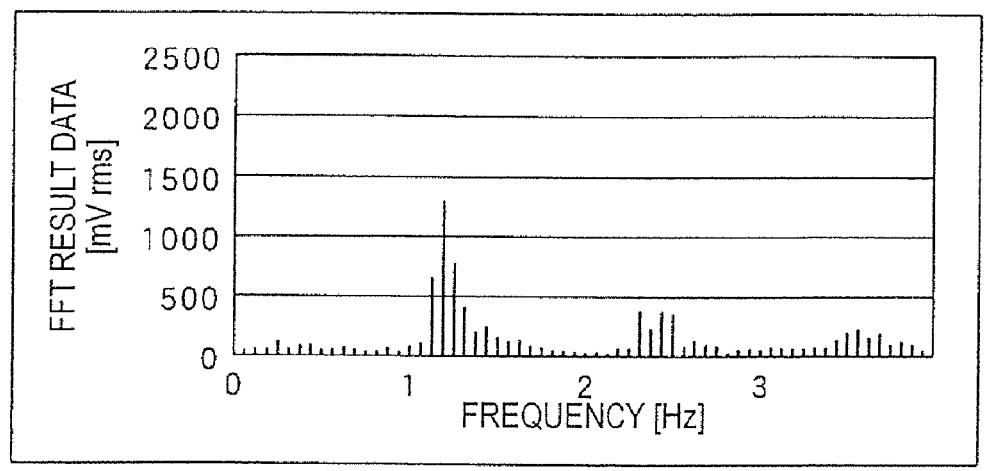
FIG. 57 shows the frequency analysis results obtained by subjecting the residual data in FIG. 56 to FFT.

FIG. 57 shows the frequency analysis results obtained by subjecting the residual data in FIG. 56 to FFT.

Thus, the frequency analysis results thus obtained have the body motion components originating in the veins substantially removed from the output signal (pulse wave components+body motion components) of the pulse wave sensor, and are, specifically, pulse wave data that primarily corresponds to the pulse wave components.

Furthermore, the MPU 94 calculates the pulse rate from the frequency on the assumption that the maximum frequency components of the resulting pulse wave data that primarily contains pulse wave components constitute the pulse spectrum.

The MPU 94 then displays the pulse rate on the display device 97.

As described above, according to the second alternative of the second embodiment, variation in the veins, which is the main factor in the body motion components generated in the body, can be also accurately detected and registered. Therefore, the body motion components can be accurately removed, making it possible to accurately detect the pulse wave components, and hence to accurately measure the pulse rate.

(2.3) Third Alternative of the Second Embodiment

A third alternative of the second embodiment is an alternative in the sense that the sensor module 81 has both the pulse wave sensor 83 and the pressure sensor 84 in the second embodiment, while in the third alternative, the sensor module 81 is divided into a sensor module 111A and a sensor module 111B, and the pulse wave sensor 83 and pressure sensor 84 are mounted on separate fingers. Aside from the above-mentioned differences, the configuration of a pulse measurement device 110 in the third alternative of the second embodiment is the same as the pulse measurement device 80 of the second embodiment.

Figure 58:
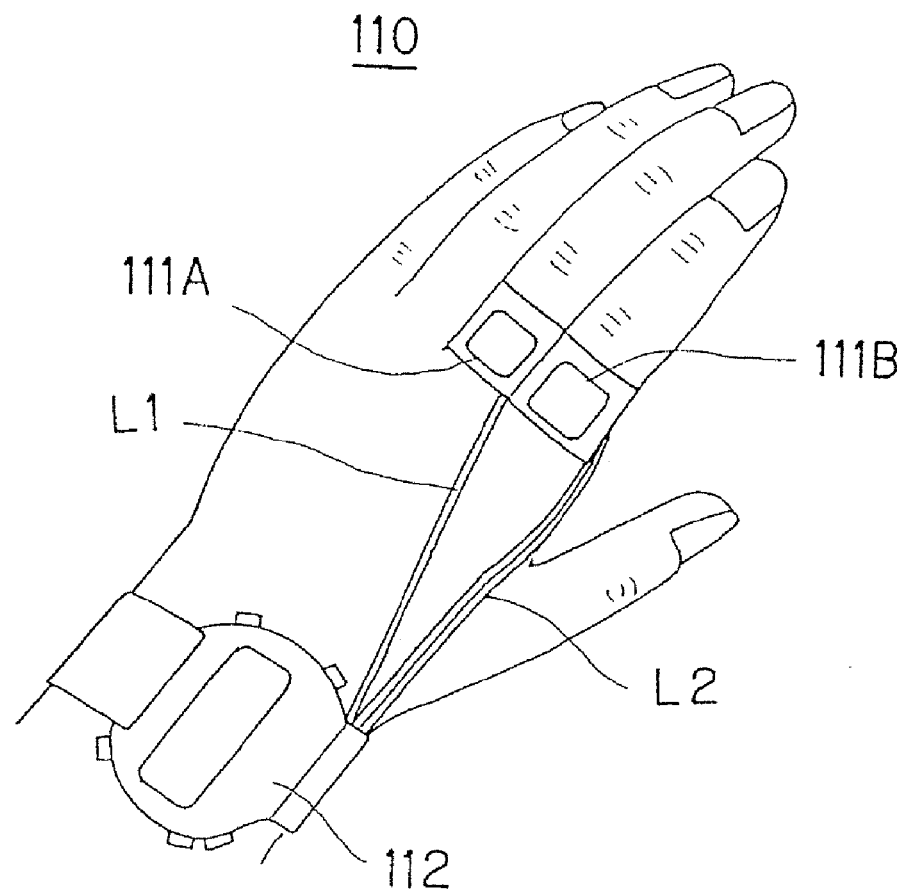
FIG. 58 is a schematic structural block diagram of a pulse measurement device according to a third alternative of the second embodiment.

FIG. 58 is a schematic structural block diagram of a pulse measurement system according to the third alternative of the second embodiment. In general terms, the pulse measurement device 110 has a sensor module 111A mounted on a first finger of the user, a sensor module 111B mounted on a second finger of the user, and a device main body 112 that is connected to the sensor module 111A via a wiring L1, is also connected to the sensor module 111B via a wiring L2, and is mounted on the arm of the user.

Figure 59:
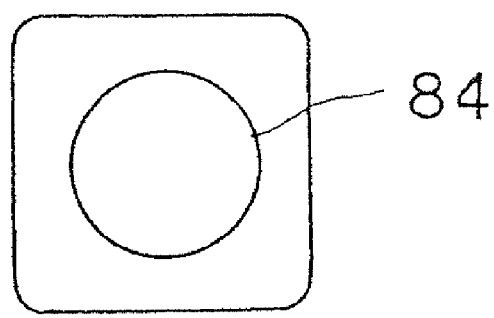
FIG. 59 is an explanatory diagram of the arrangement of sensors in a sensor module 111A of the third alternative of the second embodiment.

FIG. 59 is an explanatory diagram of the arrangement of sensors in the sensor module 111A. The sensor module 111A has the pressure sensor 84 for primarily detecting body motion components.

Figure 60:
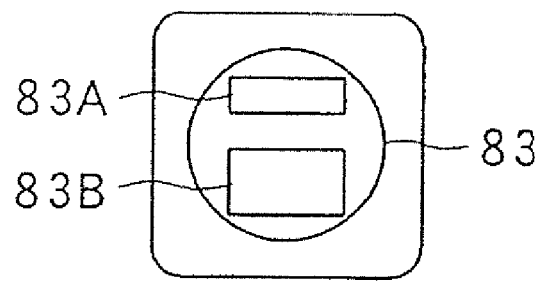
FIG. 60 is an explanatory diagram of the arrangement of the sensors in a sensor module 111B of the third alternative of the second embodiment.

FIG. 60 is an explanatory diagram of the arrangement of the sensors in the sensor module 111B. The sensor module 111B has the pulse wave sensor 83 for primarily detecting pulse wave components. As mentioned above, the pulse wave sensor 83 has the LED 83A for emitting detection light, and the PD (Photo Detector) 83B for receiving the detection light reflected by the body.

The actual detection operation is the same as in the second embodiment described above, so a detailed description thereof is omitted.

According to the third alternative of the second embodiment, measurement is taken with the pressure sensor 84 for primarily detecting body motion components and with the pulse wave sensor 83 for primarily detecting pulse wave components, mounted on separate fingers, so it is possible to reduce the effect of the mechanical arrangement of the other sensor and the effect of noise on the output signal due to the output signal of the other sensor.

In the second embodiment and the first through third alternatives of the second embodiment described above, the pressure sensor 84 was provided either adjacent to or separate from the pulse wave sensor 83, but it is also possible to use a configuration in which the pressure sensor 84 is disposed in a substantially layered state over the pulse wave sensor 83 in a direction away from the body.

(3) Third Embodiment

A pulse measurement device 120 according to a third embodiment of the present invention will now be described with reference to FIGS. 61 through 81. The main difference between the third embodiment and the second embodiment is that in the second embodiment, venous blood pressure is detected using the pressure sensor 84, while in the third embodiment, venous blood pressure is estimated by detecting the relative difference in the vertical direction between the position of the heart of the user and the mounted position of the pulse meter with the aid of an angle sensor 122. Otherwise the basic configuration is similar to the first embodiment or the second embodiment, therefore, in view of the similarity between the first/second embodiment and the third embodiment, descriptions of the parts of the third embodiment with identical or similar functions to the parts of the first/second embodiment are omitted for the sake of simplicity.

First, the operating principle of the third embodiment will be described prior to a detailed description of the third embodiment.

The second embodiment is configured to detect venous blood pressure with a pressure sensor in order to detect body motion components originating in venous blood. However, the third embodiment focuses on the concept that the relative difference in the vertical direction between the position of the heart of the user and the mounted position of the pulse meter has a proportional relationship with the vein meter pressure. Specifically, the third embodiment is designed for a case in which the relative difference in the vertical direction between the position of the heart of the user and the mounted position of the pulse meter is detected as an angle about the shoulder joint of the arm on which the pulse meter is mounted (for example, 0° when the arm hangs straight down, and 90° when the arm is horizontal).

Accordingly, the inventors have researched the relationship between the amount of change in height (of the arm) and the amount of body motion components (amount of stroke components) included in the pulse wave sensor output when the same body motion components are generated.

Figure 61:
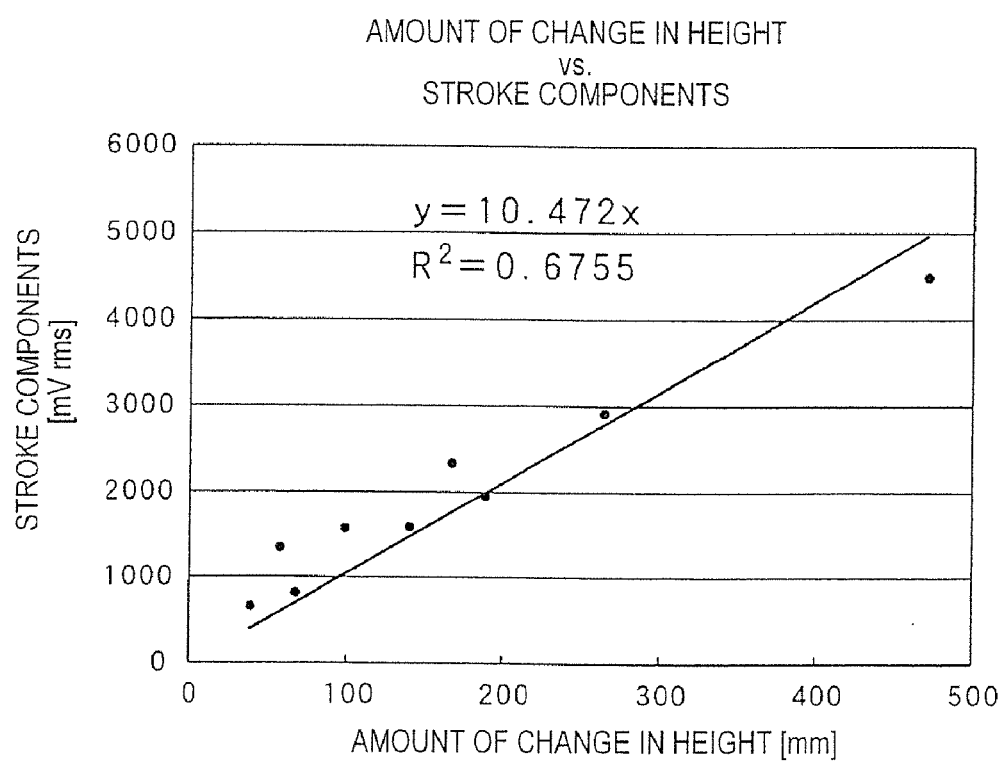
FIG. 61 is an explanatory diagram of the relationship between the amount of change in height of the arm and the amount of body motion components (amount of stroke components) included in the pulse wave sensor output.

FIG. 61 is an explanatory diagram of the relationship between the amount of change in height of the arm and the amount of body motion components (amount of stroke components) included in the pulse wave sensor output. As shown in FIG. 61, it is clear that the amount of change in height of the arm and the amount of body motion components (amount of stroke components) included in the pulse wave sensor output have a substantially proportional relationship. In other words, it is possible to surmise the effect of venous blood included in the pulse wave sensor output if the amount of change in height of the arm can be detected.

Figure 62:
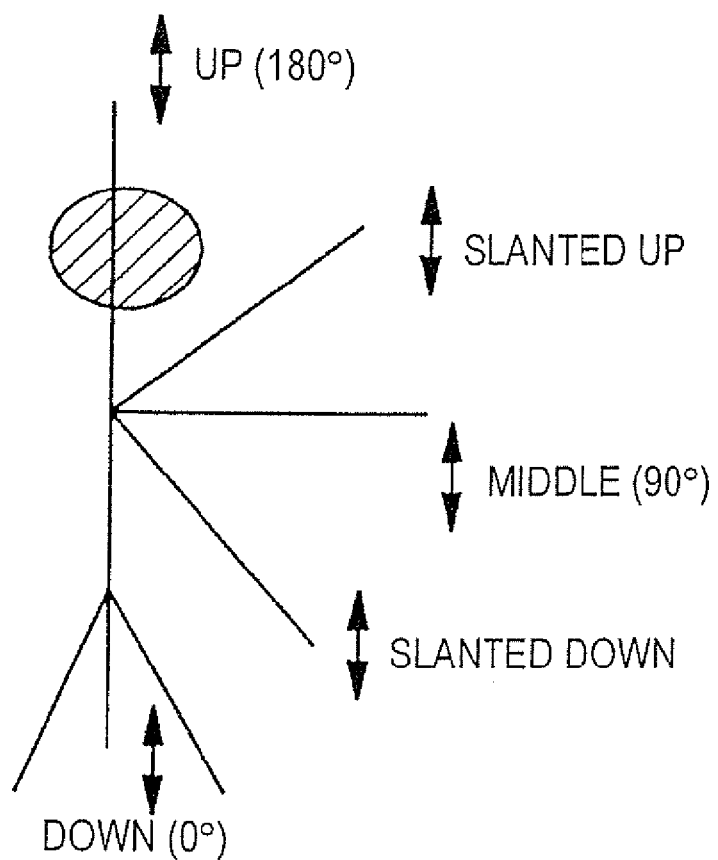
FIG. 62 is an explanatory diagram of the relationship between the angle and direction of the arm.

FIG. 62 is an explanatory diagram of the relationship between the angle and direction of the arm. In the third embodiment, the angle of the arm is 0° and the direction is down when the arm hangs straight down, the angle of the arm is 90° and the direction is middle when the arm is horizontal, and the angle of the arm is 180° and the direction is up when the arm is extended straight up. Also, the direction is slanted down when the arm is intermediate between the position of the arm hanging straight down and the position of the arm being horizontal, and the direction is slanted up when the arm is intermediate between the position of the arm being horizontal and the position of the arm extending straight up.

Figure 63:
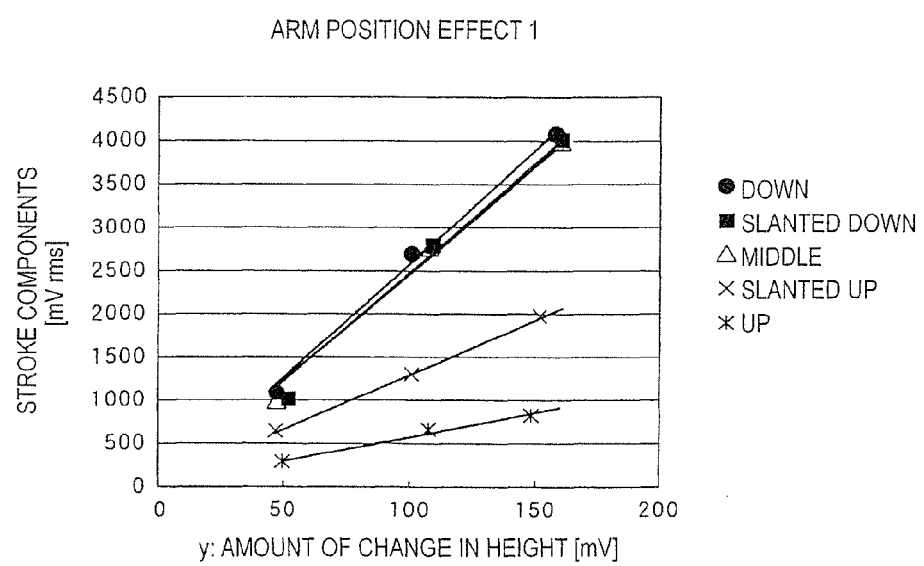
FIG. 63 is an explanatory diagram of the relationship between the amount of change in height of the arm position in the arm position (direction of the arm) in its initial state and the amount of body motion components (stroke components) as an angle sensor output.

FIG. 63 is an explanatory diagram of the relationship between the amount of change in height of the arm position (direction of the arm) in its initial state and the amount of body motion components (amount of stroke components) as an angle sensor output. As shown in FIG. 63, it is clear that when the position of the vertical direction of the arm in its initial state is level with or lower than the position of the heart of the user, or, specifically, when the direction of the arm is between the down and middle directions, the change in the amount of body motion components (amount of stroke components), which is the output of the angle sensor, displays the same tendency with any direction of the arm even if the height of the position of the arm is varied. On the other hand, when the position of the vertical direction of the arm in its initial state is higher than the position of the heart of the user, or, specifically, when the direction of the arm is between the slanted up and up directions, it is clear that the amount of body motion components (amount of stroke components) as the angle sensor output has an overall tendency to decrease along with a reduction in venous blood pressure.

Figure 64:
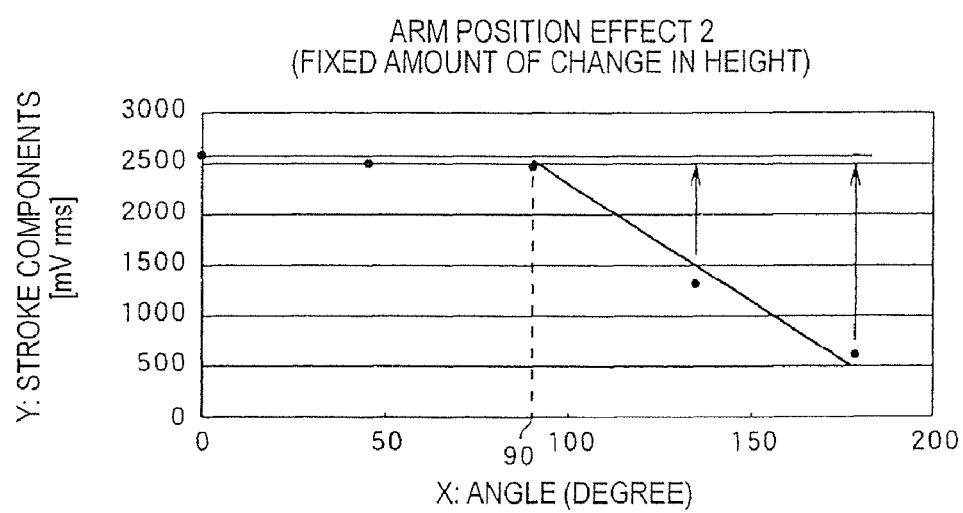
FIG. 64 is an explanatory diagram of the change in the amount of body motion components (stroke components) as the angle sensor output depending on the position of the arm when the amount of change in height is fixed.

FIG. 64 is an explanatory diagram of the change in the amount of body motion components (stroke components) as the angle sensor output due to the position of the arm when the amount of change in height is fixed. As seen in FIG. 64, it is clear that the amount of body motion components as the angle sensor output is low when the angle of the arm is greater than 90°.

From these results, the angle sensor output shall be corrected when the angle of the arm is greater than 90°.

Figure 65:
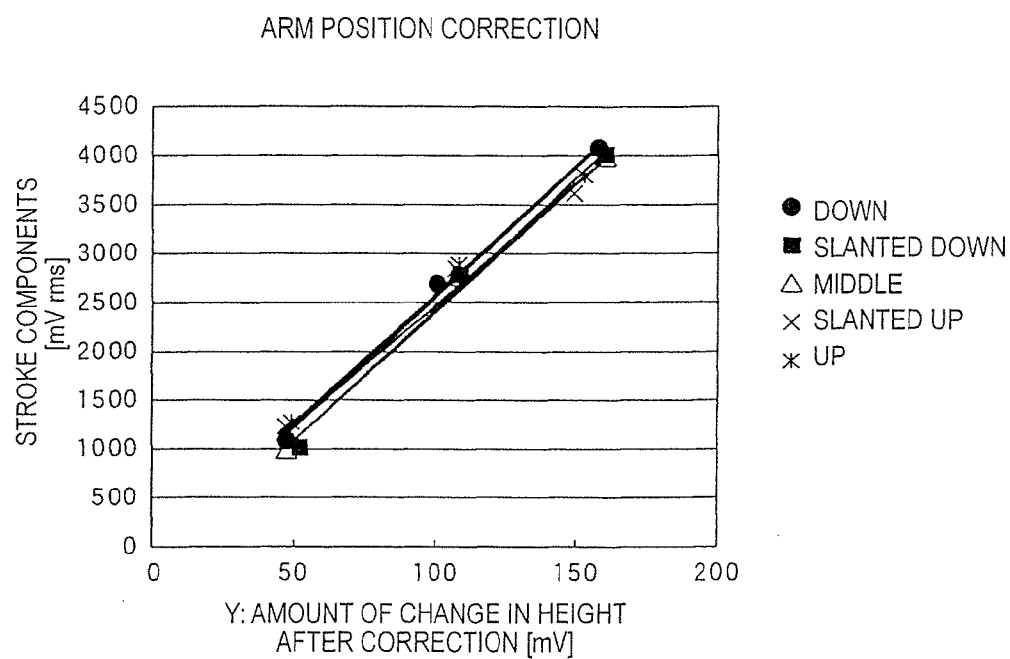
FIG. 65 is an explanatory diagram of the relationship between the amount of change in height of the arm position in the position of the arm (direction of the arm) in its initial state and the amount of body motion components (stroke components) included in the angle sensor output after correction.

FIG. 65 is an explanatory diagram of the relationship between the amount of change in height of the position of the arm (direction of the arm) in its initial state and the amount of body motion components (stroke components) included in the angle sensor output after correction. This case involves the example in FIG. 63, in which the amount of body motion components (amount of stroke components) Y corresponding to the angle sensor output is corrected by the angle X of the arm according to the following formula when the angle of the arm is greater than 90°.

$Y = y \cdot (X-90)/22.2$, where y is the amount of change in height (mV),
X is the angle (degree), and
Y is the amount of change in height (mV) after correction.

As a result, as shown in FIG. 65, it is possible to detect the amount of body motion components (amount of stroke com-ponents) included in the pulse wave sensor output without any influence from the arm position.

In view of this, in the third embodiment, the relative difference in the vertical direction between the position of the heart of the user and the mounted position of the pulse meter is detected by an external angle sensor, and the body motion components originating in the veins are subtracted from the pulse wave sensor output at a specific rate, whereby the pulse rate is accurately detected based on a signal from which the effect of venous blood has been removed.

The third embodiment will now be described in detail.

Figure 66A:
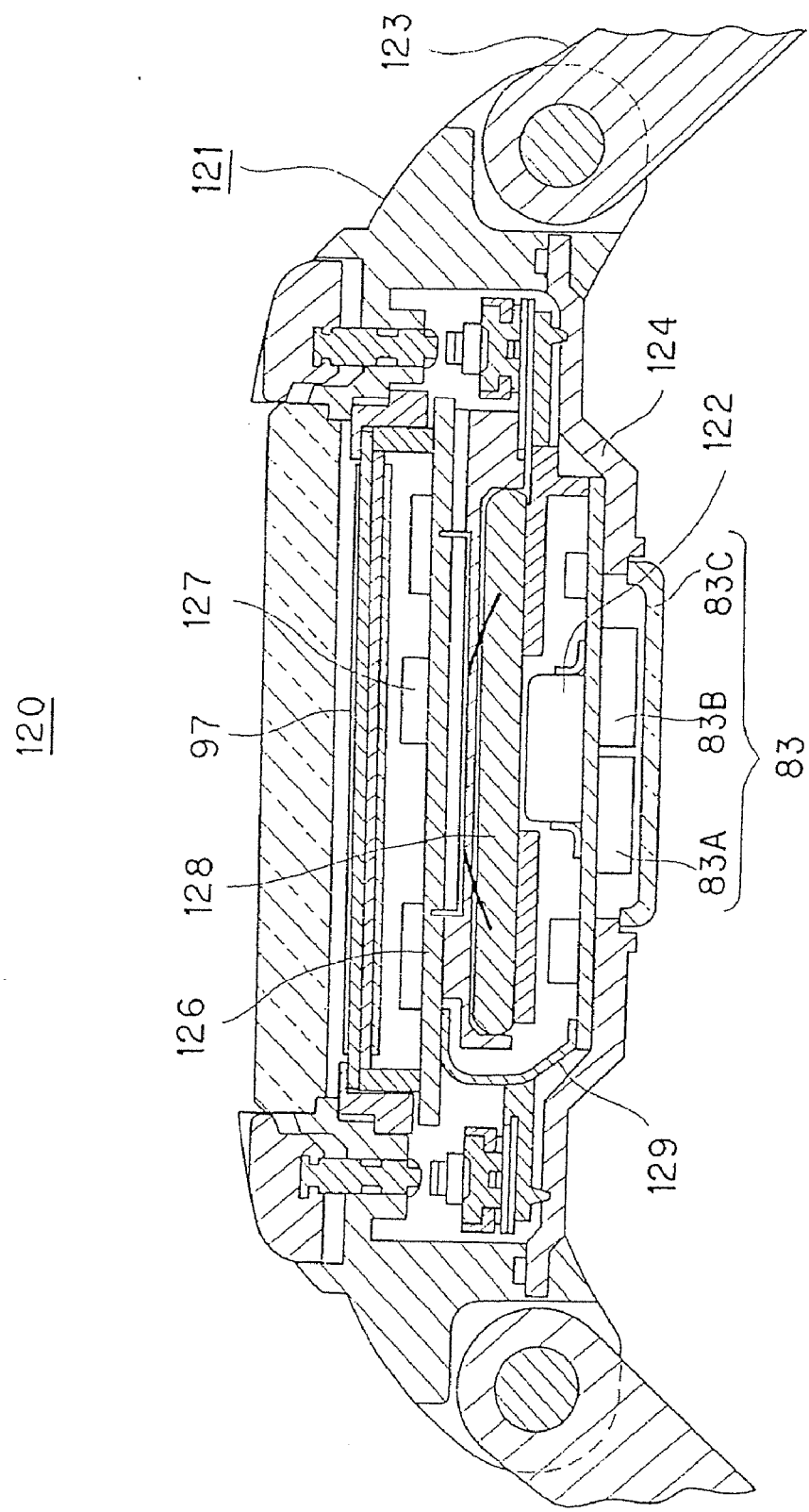
FIG. 66A is a cross-sectional view of a pulse measurement device of a third embodiment which is incorporated into a watchcase.

FIG. 66A is a cross-sectional view of the pulse measurement device 120 wherein the pulse meter of the third embodiment is incorporated into a watchcase. In this example, the pulse wave sensor 83 and an angle sensor 122 are provided on the reverse surface of a watchcase 121 of the pulse measurement device 120. As shown in FIG. 66A, the pulse wave sensor 83 described above is formed integrally with the main body on the reverse side of the watchcase 121. The watchcase 121 is provided with a wristband 123 for arm mounting, and the reverse side of the watchcase 121 is pressed against the back of the wrist when the wristband 123 is mounted by being wound around the wrist.

The reverse side of the watchcase 121 is provided with transparent glass 83C as a component of the pulse wave sensor 83. The transparent glass 83C is fixed to the watchcase 121 by a back lid 124. The transparent glass 83C protects the LED 83A and the PD 83B, which are components of the pulse wave sensor 83, and also transmits the light incident on the LED 13C and reflected light obtained via the body, and directs the light to the PD 83B.

The front side of the watchcase 121 is provided with a liquid crystal display device or another such display device 97 for displaying the pulse rate HR and other such living organism information based on the detection results from the pulse wave sensor 83 in addition to the current time and date. Also, the interior of the watchcase 121 has a CPU and other such IC circuits on a main board 126, whereby a data processing circuit 127 is configured.

Also, the reverse side of the main board 126 is provided with a battery 128, and the battery 128 supplies power to the display device 97, the main board 126, and the pulse wave sensor 83.

The main board 126 and the pulse wave sensor 83 are designed to be connected by a heat seal 129, wherein power is supplied to the pulse wave sensor 83 and the angle sensor 122 from the main board 126, the pulse wave detection signal is fed to the main board 126 from the pulse wave sensor 83, and the angle detection signal is fed from the angle sensor 122 by a wiring formed by the heat seal 129.

The data processing circuit 127 subjects the pulse wave signal to FFT and calculates the pulse rate HR by analyzing the processing results thereof. The external surface of the watchcase 121 is provided with button switches (not shown) for time setting, display mode switching, and the like.

The reverse side of the watchcase 121 faces the back of the wrist when the wristband 123 is wound around the wrist. Therefore, the light from the LED 83A is directed to the back of the wrist via the transparent glass 83C, and the reflected light is received by the PD 83B.

The angle sensor 122 outputs an angle detection signal used to determine the relative difference in the vertical direction between the position of the heart of the user and the mounted position of the pulse meter. Therefore, the angle sensor 122 essentially constitutes a difference detecting section. A differential capacitive sensor 122A or a rotary-spindle angle sensor 122B is preferably used as the angle sensor 122.

Figure 67:
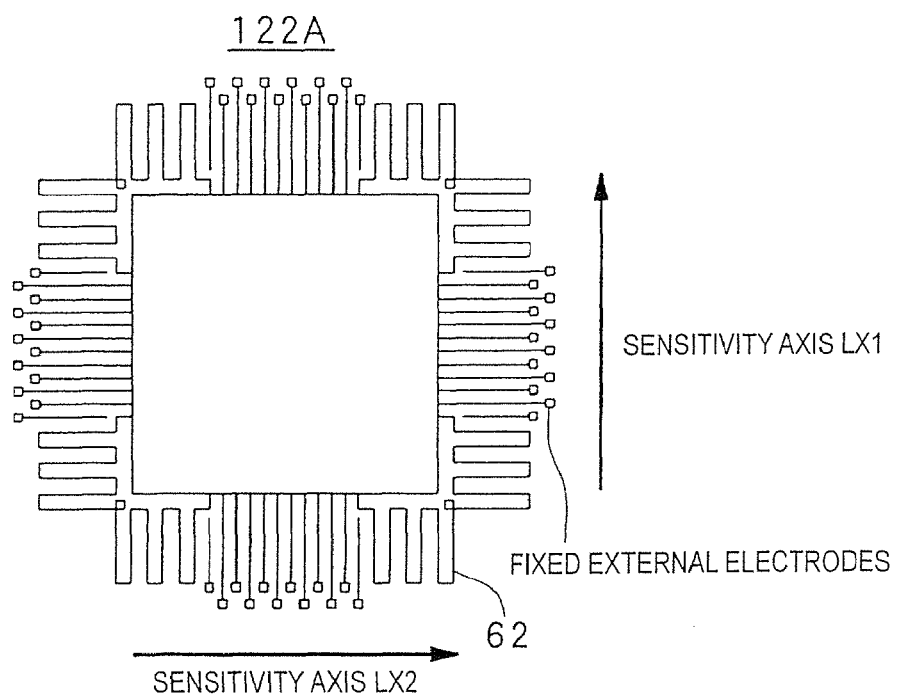
FIG. 67 is a schematic structural diagram of a differential capacitive sensor, which is an angle sensor.
Figure 68:
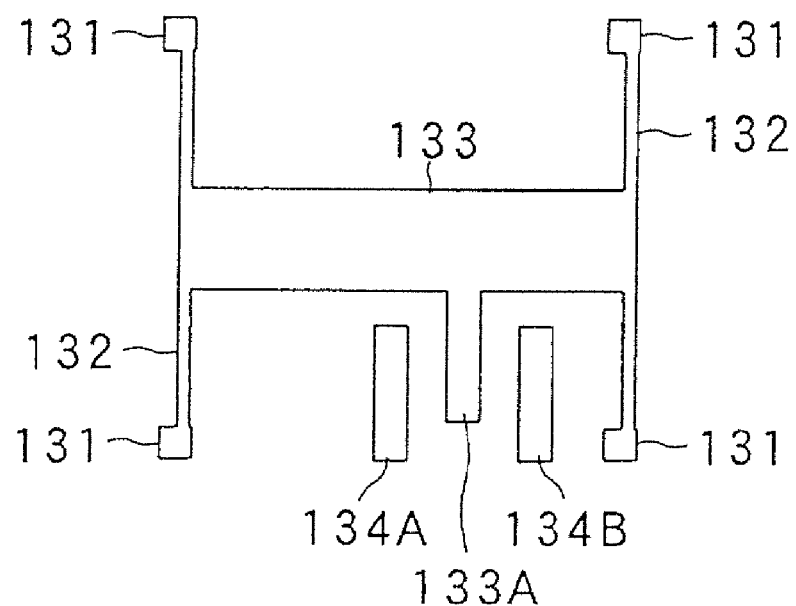
FIG. 68 is a partial enlarged diagram of the differential capacitive sensor.

FIG. 67 is a structural schematic diagram of the differential capacitive sensor 122A used as the angle sensor. FIG. 68 is a partial enlarged diagram of the differential capacitive sensor 122A before acceleration is applied.

The differential capacitive sensor 122A is a biaxial acceleration sensor and has a first sensitivity axis LX1 and a second sensitivity axis LX2. The differential capacitive sensor 122A has flexible tethers 132 supported by a pair of fixed shafts 131. The tethers 132 support a beam 133 from both sides. The beam 133 is provided with an electrode 133A protruding from the side, which is held by a pair of fixed external electrodes 134A and 134B so as to face both fixed external electrodes 134 at a position virtually equidistant from the fixed external electrodes 134A and 134B. Thus, the electrode 133A and the fixed external electrodes 134A and 134B each function as capacitors with roughly the same capacitance.

Figure 69:
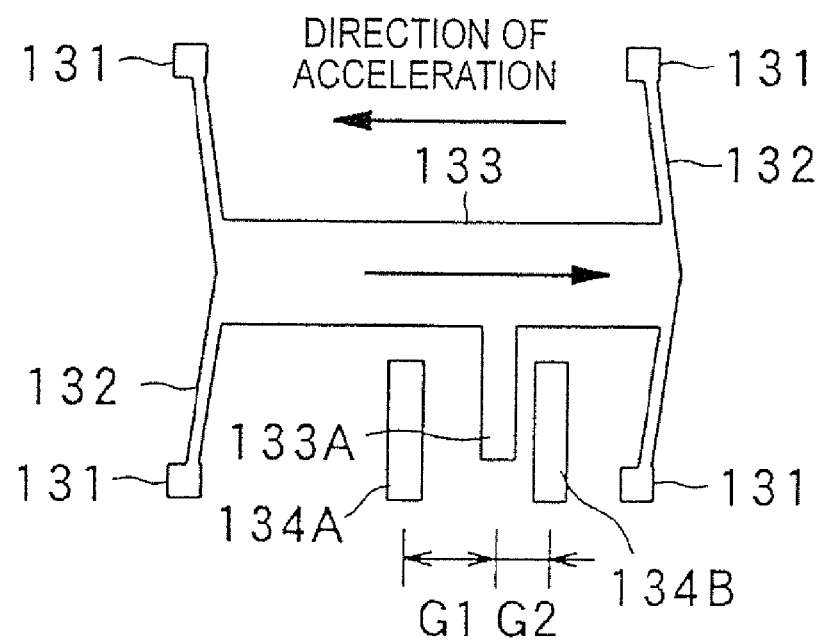
FIG. 69 is an explanatory diagram of the operation of the differential capacitive sensor.

FIG. 69 is a partial enlarged diagram of a differential capacitive sensor to which acceleration has been applied. In the state shown in FIG. 68, when the differential capacitive sensor 122A is tilted, the tethers 132 bend due to gravitational acceleration, resulting in the state shown in FIG. 69. As a result, for example, the distance G1 between the electrode 133A and the fixed external electrode 134A becomes greater than the distance G2 between the electrode 133A and the fixed external electrode 134B, as shown in FIG. 69. Specifically, the capacitance of the capacitor configured by the electrode 133A and the fixed external electrode 134B becomes greater. Therefore, since this difference in capacitance is proportional to the extent of gravitational acceleration, or, specifically, to the angle of inclination, it is possible to detect the angle by measuring the difference in capacitance.

Figure 70:
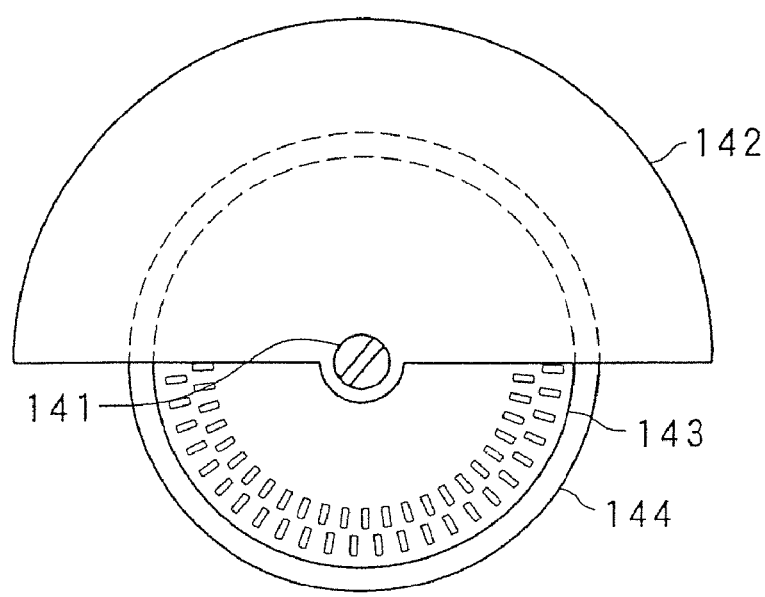
FIG. 70 is a front view of a rotary-spindle angle sensor used as an angle sensor.
Figure 71:
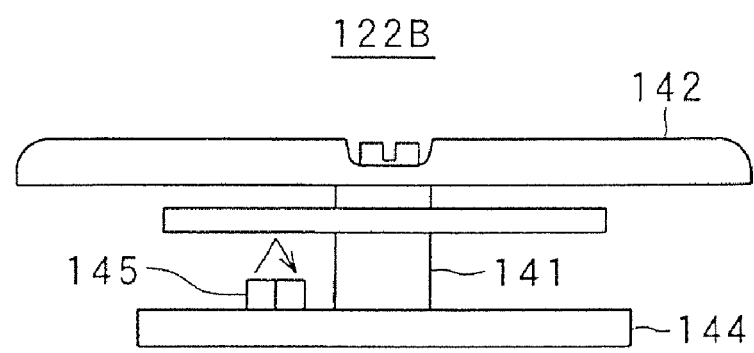
FIG. 71 is a side view of the rotary-spindle angle sensor in FIG. 70.

FIG. 70 is a front view of the rotary-spindle angle sensor 122B used as the angle sensor. FIG. 71 is a side view of the rotary-spindle angle sensor 122B in FIG. 70.

In general terms, the rotary-spindle angle sensor 122B has a supporting axle 141, a rotary spindle 142 rotatably supported by the supporting axle 141, a slitted plate 143 that rotates uniformly with the rotary spindle 142 and has two groups of slits formed with different phases, a fixed plate 144 for holding the supporting axle 141, and an optical sensor unit 145 disposed in a position on the fixed plate 144 facing the slitted plate 143. According to this configuration, the optical sensor unit 145 outputs an angle detection signal with a pulse rate corresponding to the amount of rotations of the slitted plate 143 for each group of slits when the rotary spindle 142 rotates due to a change in the angle. At this point it is also possible to detect the changing direction of the angle because the phase relationship of the angle detection signals for both groups of slits differs in terms of the rotating direction of the rotary spindle.

The specific pulse rate calculation process in the third embodiment will now be described.

Figure 72:
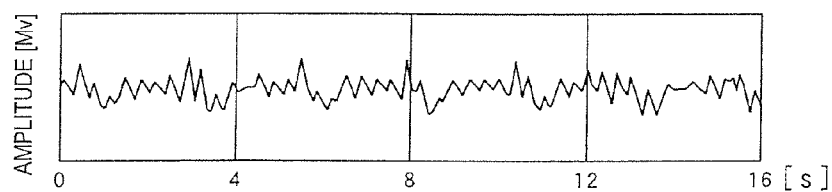
FIG. 72 is a graph of a chronological arrangement of one example of detected pulse wave data.
Figure 73:
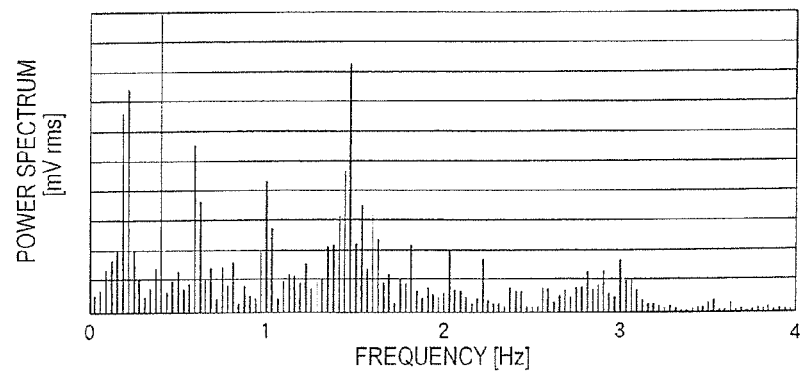
FIG. 73 shows the frequency analysis results obtained by subjecting the detected pulse wave data in FIG. 72 to FFT.
Figure 74:
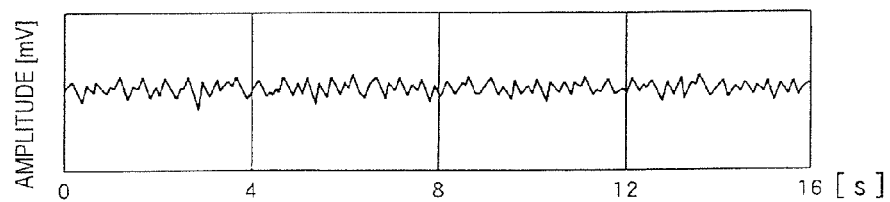
FIG. 74 is a graph of a chronological arrangement of one example of detected angle data.
Figure 75:
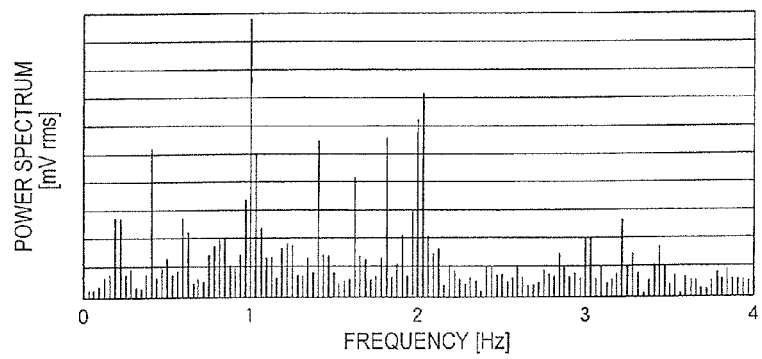
FIG. 75 shows the frequency analysis results obtained by subjecting the detected angle data in FIG. 74 to FFT.

FIG. 72 is a graph of a chronological arrangement of one example of detected pulse wave data. FIG. 73 shows the frequency analysis results obtained by subjecting the detected pulse wave data in FIG. 72 to FFT. FIG. 74 is a graph of a chronological arrangement of one example of detected angle data. FIG. 75 shows the frequency analysis results obtained by subjecting the detected angle data in FIG. 74 to FFT.

Figure 66B:
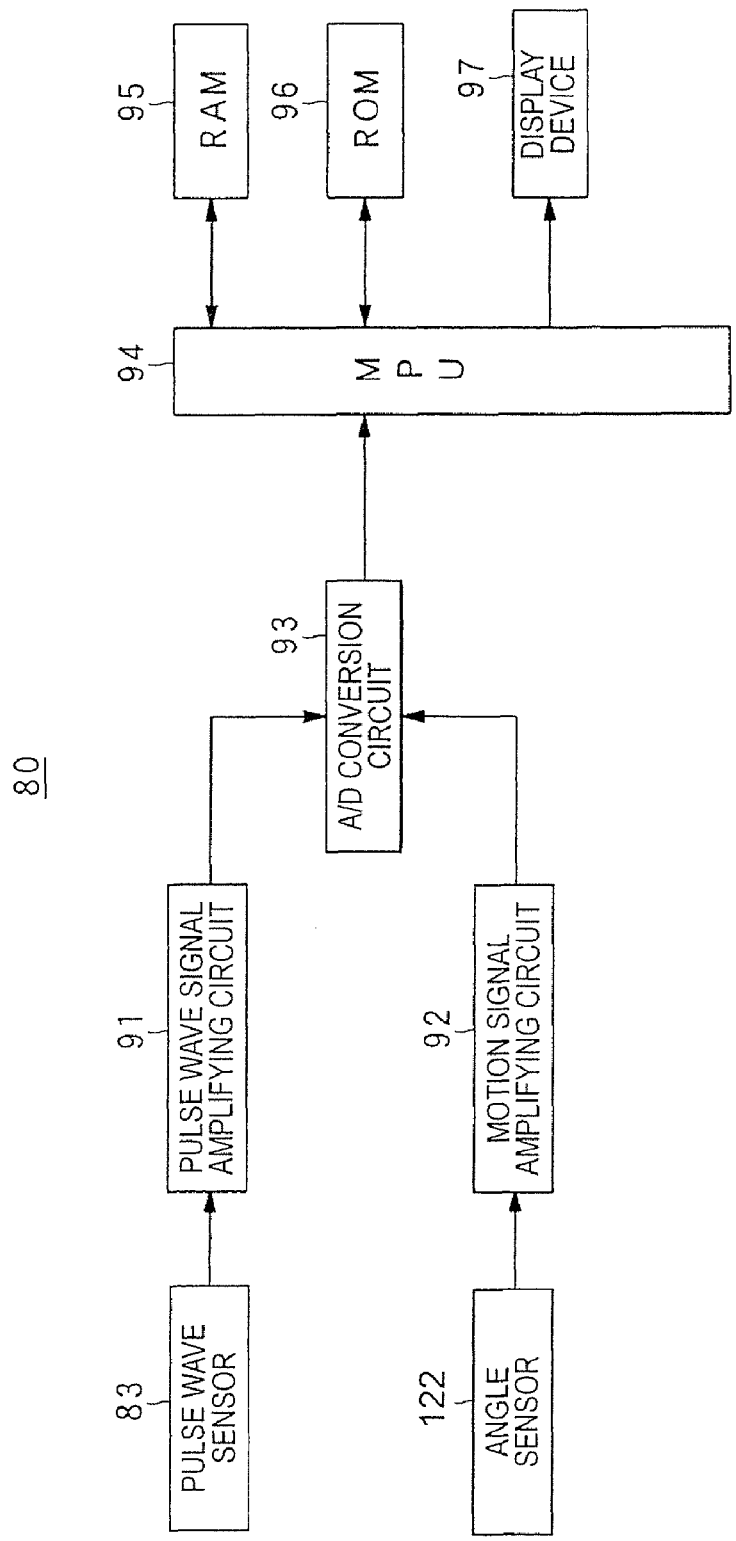
FIG. 66B is a schematic structural block diagram of the pulse measurement device of the third embodiment.

The configuration as a pulse measurement device is essentially the same as the second embodiment, and will now be described with reference to the schematic structural block diagram in FIG. 66B. In this case, the body motion sensor 122 is an angle sensor.

Figure 66C:
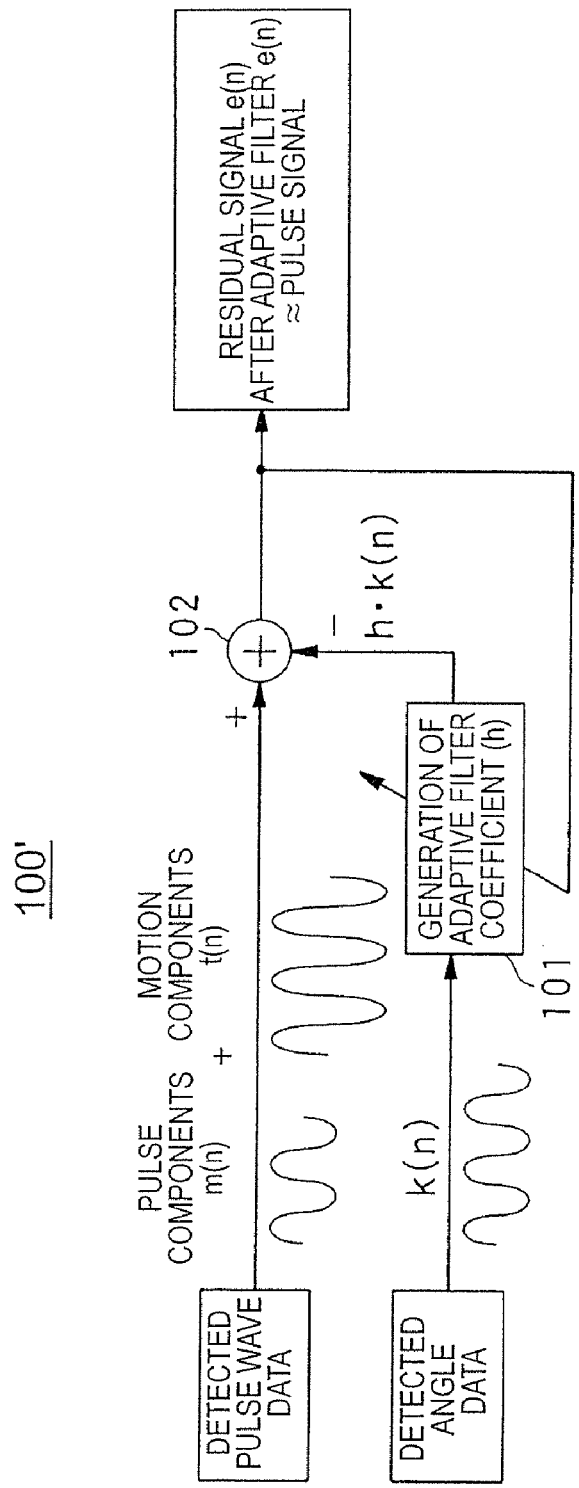
FIG. 66C shows a schematic structural block diagram of one example of an adaptive filter of the third embodiment.

The MPU 94 has the functions of the adaptive filter 100' shown in FIG. 66C.

First, the MPU 94 sequentially reads out the detected pulse wave data and the detected angle data stored in the RAM 95, and outputs the detected pulse wave data in a certain sampling period to the synthesizer 102.

The MPU 94 also presents the filter coefficient generating section 101 with detected angle data that corresponds to the detected pulse wave data.

Thus, the filter coefficient generating section 101 generates the adaptive filter coefficient h based on the data previously outputted by the synthesizer 102 to which the filter has been applied. The adaptive filter coefficient h is then applied to the inputted detected angle data (=k(n)) functioning as a body motion component detection signal, and body motion removal data (=h·k(n)) is outputted to the synthesizer 102.

The synthesizer 102 thereby combines the current pulse wave data and body motion removal data, substantially removes (subtracts) the body motion components contained in the current detected pulse wave data, extracts the pulse wave components, and outputs the residual data (=data to which the filter has been applied).

Figure 76:
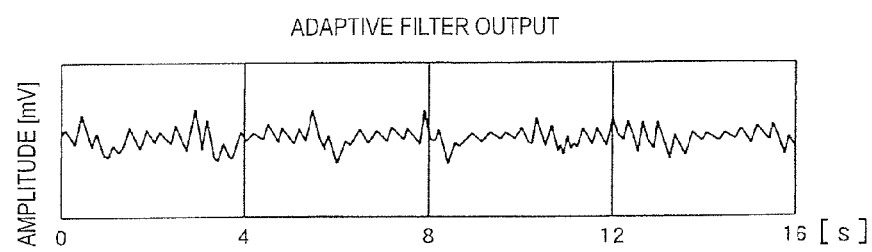
FIG. 76 is a graph of a chronological arrangement of residual data obtained by applying an adaptive filter to the detected pulse wave data in FIG. 72 and the detected angle data in FIG. 74.

FIG. 76 is a graph of a chronological arrangement of residual data obtained by applying an adaptive filter to the detected pulse wave data in FIG. 72 and the detected angle data in FIG. 74.

Next, the MPU 94 subjects the residual data in FIG. 76 to FFT.

Figure 77:
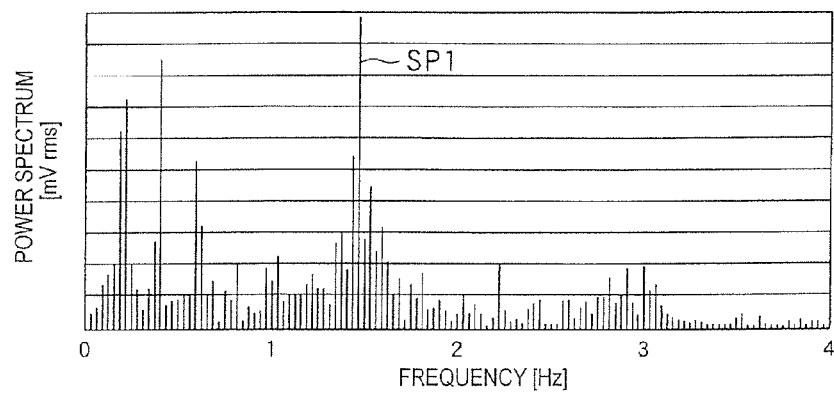
FIG. 77 shows the frequency analysis obtained by subjecting the residual data in FIG. 76 to FFT.

FIG. 77 shows the frequency analysis obtained by subjecting the residual data in FIG. 76 to FFT. Thus, the frequency analysis results thus obtained have the body motion components originating in the veins substantially removed from the output signal (pulse wave components+body motion components) of the pulse wave sensor, and are, specifically, pulse wave data that primarily corresponds to the pulse wave components.

Furthermore, the MPU 94 calculates the pulse rate from the frequency on the assumption that the maximum frequency components of the resulting pulse wave data that primarily contains pulse wave components constitute the pulse spectrum SP1.

The MPU 94 then displays the pulse rate on the display device 97.

Figure 78:
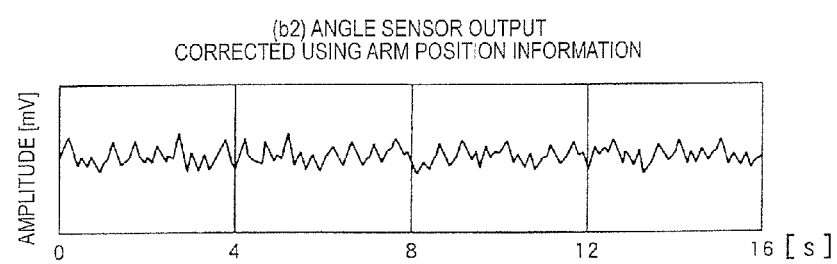
FIG. 78 is a graph of a chronological arrangement of one example of corrected detected angle data.
Figure 79:
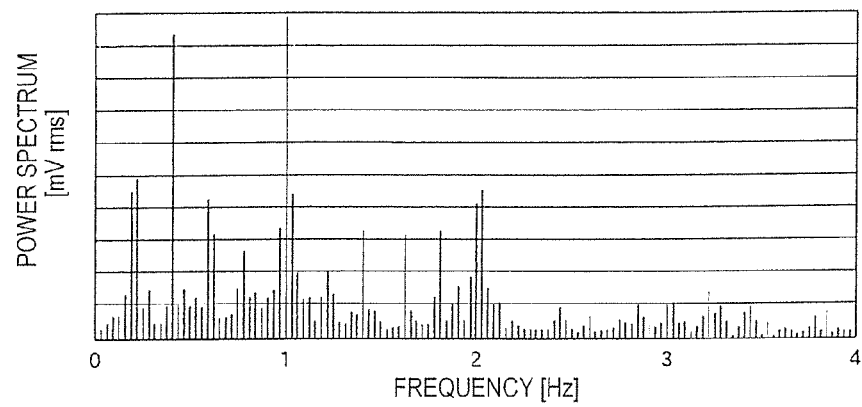
FIG. 79 shows the frequency analysis obtained by subjecting the corrected detected angle data to FFT.

The above description pertained to a case in which the output from the angle sensor 122 was not corrected, but as described above, the body motion components as an output from the angle sensor 122 is detected small when the angle of the arm is greater than 90°. Therefore, the output from the pulse wave sensor 83 is corrected when the angle of the arm is greater than 90°. FIG. 78 is a graph of a chronological arrangement of one example of corrected detected angle data. FIG. 79 shows the frequency analysis obtained by subjecting the corrected detected angle data in FIG. 78 to FFT.

Similarly, the MPU 94 sequentially reads out the detected pulse wave data and the detected angle data stored in the RAM 95, outputs the detected pulse wave data in a certain sampling period to the synthesizer 102, and outputs the corrected detected angle data that corresponds to the detected pulse wave data to the filter coefficient generating section 101.

Thus, the filter coefficient generating section 101 creates the adaptive filter coefficient h based on the data previously outputted by the synthesizer 102 to which the filter has been applied. The adaptive filter coefficient h is then applied to the inputted detected angle data functioning as a body motion component detection signal and the body motion removal data (=h·k(n)) is outputted to the synthesizer 102. The synthesizer 102 then combines the current pulse wave data and body motion removal data, substantially removes (subtracts)

the body motion components contained in the current detected pulse wave data, extracts the pulse wave components, and outputs the residual data (=data to which the filter has been applied).

Figure 80:
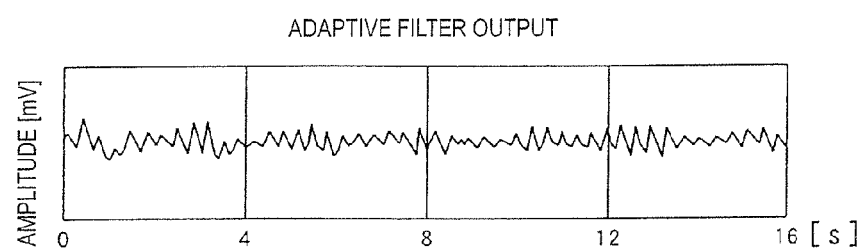
FIG. 80 is a graph of a chronological arrangement of residual data obtained by applying an adaptive filter to the detected pulse wave data in FIG. 72 and the corrected detected angle data in FIG. 78.

FIG. 80 is a graph of a chronological arrangement of residual data obtained by applying an adaptive filter to the detected pulse wave data in FIG. 72 and the corrected detected angle data in FIG. 78. The MPU 94 subjects this residual data to FFT.

Figure 81:
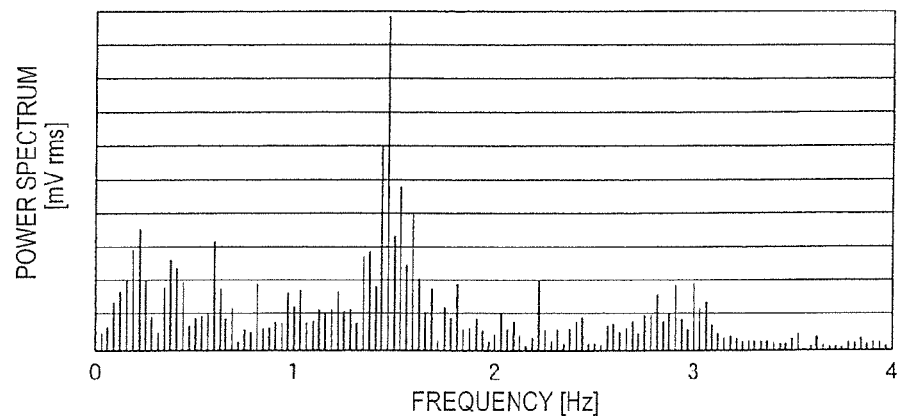
FIG. 81 shows the frequency analysis results obtained by subjecting the residual data in FIG. 80 to FFT.

FIG. 81 shows the frequency analysis results obtained by subjecting the residual data in FIG. 80 to FFT. As shown in FIG. 81, it is clear from the frequency analysis results thus obtained that although the frequency analysis results and the height of the peak on the pulse spectrum SP1 shown in FIG. 77 do not change, the height of the peaks of other spectra is suppressed, and the MPU 94 can more accurately calculate the pulse rate from the frequency on the assumption that the maximum frequency components of the pulse wave data constitute the pulse spectrum SP1.

As described above, according to the third embodiment, variation in the veins, which is the main factor in the body motion components generated in the body, can be more accurately detected and registered, particularly when angle correction is performed. Therefore, the body motion components can be accurately removed, making it possible to accurately detect pulse wave components, and hence to accurately measure the pulse rate.

In the third embodiment described above, the angle sensor 122 was provided adjacent to or separate from the pulse wave sensor 83, but it is also possible to use a configuration in which the angle sensor 122 is disposed in a substantially layered state over the pulse wave sensor 83 in a direction away from the body.

Furthermore, the third embodiment described a case in which the control program is stored in the ROM 96 in advance, but another possibility is a configuration in which the control program is stored in advance on various magnetic disks, optical disks, memory cards, and other such storage media, and is read from these storage media and installed. Another possibility is a configuration in which a communication interface is provided for downloading the control program via the Internet, LAN, or another such network; installing the program; and running this program.

(4) Fourth Embodiment

A pulse measurement device 190 according to a fourth embodiment of the present invention will now be described with reference to FIGS. 82 through 109. The main difference between the second embodiment and the fourth embodiment is that the fourth embodiment uses a configuration in which, instead of using the pressure sensor 84 of the second embodiment, body motion components are estimated using a blood vessel simulation sensor 150, 160, 170, or 180 for simulating the movement of venous blood, and these body motion components are removed from the output signal of the pulse wave sensor. Otherwise the basic configuration is similar to that of the second embodiment; therefore, in view of the similarity between the second embodiment and the fourth embodiment, descriptions of the parts of the fourth embodiment with identical or similar functions to the parts of the second embodiment may be omitted for the sake of simplicity.

First, the operating principle of the fourth embodiment will be described prior to a detailed description of the fourth embodiment.

The output of the pulse wave sensor for detecting pulse waves includes various body motion components in addition to pulse wave components. These body motion components are known to be generated by changes in the body originating in the movements (walking/running, arm movement, and the like) of the user whose pulse is to be measured, and, as described above, means in which detection light from an LED, which is a light-emitting element, is directed into the body, and reflected light is received by a PD (Photo Detector), which is a light receiving element, is used as the means for detecting the body motion components inside the body.

In this case, the detection light directed into the body is absorbed and scattered by arteriolovenous blood flowing near the skin and by the body tissue, the change in the amount of detection light received by the PD at rest in the absence of movement is primarily determined by the change in arterial blood due to pulsation, and absorbed light components due to venous blood and tissues are substantially constant.

However, in addition to changes in arterial blood due to pulsation, the movement of venous blood due to inertia and deformation of tissues and other such variations are generated synchronously with body motion during movement (walking, running, and the like) that accompanies body motion. As a result, the detection light directed to the inside of the body changes in terms of its absorptive and reflective characteristics and is received in the PD, and the effect thereof cannot be ignored.

On the other hand, when the sensor for detecting body motion components is mounted on the body surface of the user in a pressurized state by an elastic band (for example, a supporter), the movement of venous blood is primarily detected under such circumstances because variations in tissue and other such fluctuations are suppressed.

In view of the foregoing, the fourth embodiment involves estimating the body motion components by focusing on the movement of venous blood and simulating the movement of venous blood when the body motion components in the body are to be removed, and removing the body motion components from the output signal of the pulse wave sensor.

Figure 82:
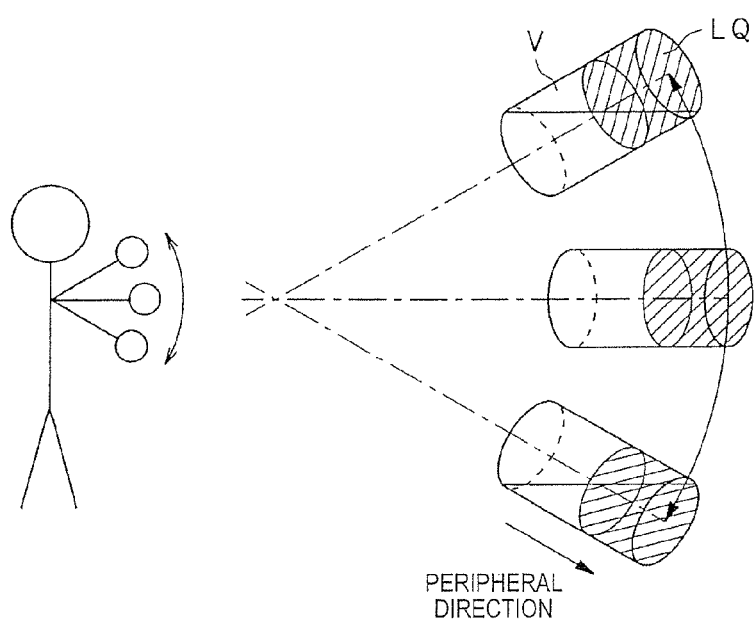
FIG. 82 is a diagram illustrating the principle of a blood vessel simulation sensor mounted on the body and designed for simulating the movement (behavior) of venous blood.

FIG. 82 is a diagram illustrating the principle of a blood vessel simulation sensor mounted on the body and designed for simulating the movement (behavior) of venous blood.

Compared to arterial blood, venous blood has low blood pressure and is therefore susceptible to the effect of inertial force due to gravity and arm movements. Therefore, as shown in FIG. 82, a solution LQ with a specific viscosity is sealed inside a cylindrical sealed container that models a blood vessel in the peripheral direction, whereby it is possible to estimate the body motion (behavior) of venous blood by observing the body motion (behavior) of the solution from the outside, and the body motion components generated in the body can be observed from the estimated movement of venous blood.

In the fourth embodiment, the movement of the solution sealed inside a cylindrical sealed container is detected by a pressure sensor, an optical sensor or another such sensor, and body motion components generated in the body are detected based on the output signal of this sensor.

As a result, according to the fourth embodiment, the pulse rate is accurately detected based on the signal from which the effect of venous blood has been removed.

The embodiments of the blood vessel simulation sensor will now be described with reference to FIGS. 83 through 88. In general terms, the embodiments of the blood vessel simulation sensor are classed into a rigid type, an elastic type, and an acceleration sensor type. The rigid type is a sensor in which a solution with a viscosity (for example, 1 to 100 cP) that exhibits the same behavior as blood is sealed in a rigid cylindrical container. The elastic type is a sensor in which a resilient tube is closed off at both ends and a solution with a viscosity (for example, 1 to 100 cP) that exhibits the same behavior as blood is sealed in the tube. The blood vessel simulation sensor of the acceleration sensor type is one in which the acceleration sensor in FIG. 82 whose direction of sensitivity is the peripheral direction is used as a blood vessel simulation sensor.

Figure 83:
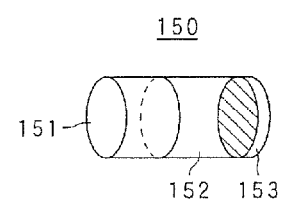
FIG. 83 is a schematic diagram of a first rigid type of blood vessel simulation sensor.

FIG. 83 is a schematic diagram of a first rigid type of blood vessel simulation sensor 150. The blood vessel simulation sensor 150 has a resinous (plastic) casing 151 closed off at both ends, and simulation blood 152 whose viscosity is set to ensure a behavior similar to that of venous blood is sealed in the casing 151 inside the sensor. Furthermore, a pressure sensor (behavior detection sensor) 153 for detecting pressure changes in accordance with the movement of the simulation blood 152 is provided to one end of the casing 151 in the longitudinal direction.

Figure 84:
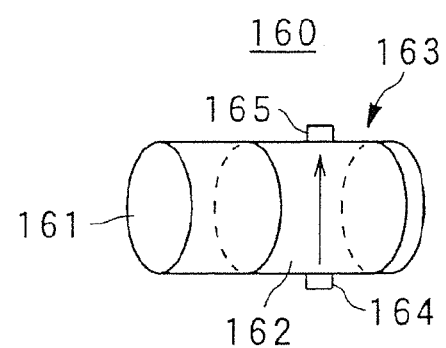
FIG. 84 is a schematic diagram of a second rigid type of blood vessel simulation sensor.

FIG. 84 is a schematic diagram of a second rigid type of blood vessel simulation sensor 160. The blood vessel simulation sensor 160 has a resinous (plastic) casing 161 closed off at both ends, and simulation blood 162 whose viscosity is set to ensure a behavior similar to that of venous blood is sealed in the casing 161 inside the sensor. Furthermore, an optical sensor (behavior detection sensor) 163 for detecting the state of movement of the simulation blood 162 is provided to the sidewall of the casing 161. The optical sensor 163 has an LED 164 for emitting detection light and a PD 165 for receiving the detection light. In this case, the simulation blood 162 is colored the same as the detection light, and the optical sensor 163 detects changes in the state of the liquid surface.

Figure 85:
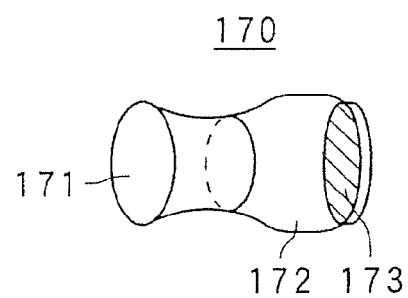
FIG. 85 is a schematic diagram of a first elastic type of blood vessel simulation sensor.

FIG. 85 is a schematic diagram of a first elastic type of blood vessel simulation sensor 170. The blood vessel simulation sensor 170 has a resinous (plastic) casing 171 closed off at both ends, and simulation blood 172 whose viscosity is set to ensure a behavior similar to that of venous blood is sealed in the casing 171 inside the sensor. Furthermore, a pressure sensor (behavior detection sensor) 173 for detecting pressure changes in accordance with the movement of the simulation blood 172 is provided to one end of the casing 171 in the longitudinal direction.

Figure 86:
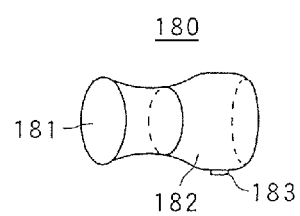
FIG. 86 is a schematic diagram of a second elastic type of blood vessel simulation sensor.

FIG. 86 is a schematic diagram of a second elastic type of blood vessel simulation sensor 180. The blood vessel simulation sensor 180 has a resilient resinous casing 181 made of rubber or the like and closed off at both ends, and simulation blood 182 whose viscosity is set to ensure a behavior similar to that of venous blood is sealed in the casing 181 inside the sensor. Furthermore, a pressure sensor (behavior detection sensor) 183 for detecting pressure changes in accordance with the movement of the simulation blood 182 is provided to the sidewall of the casing 181.

The relationship between the rigid type and elastic type of blood vessel simulation sensors 150 through 180 and the body motion components (stroke components) detected by the separate pulse wave sensors will now be described.

Figure 87:
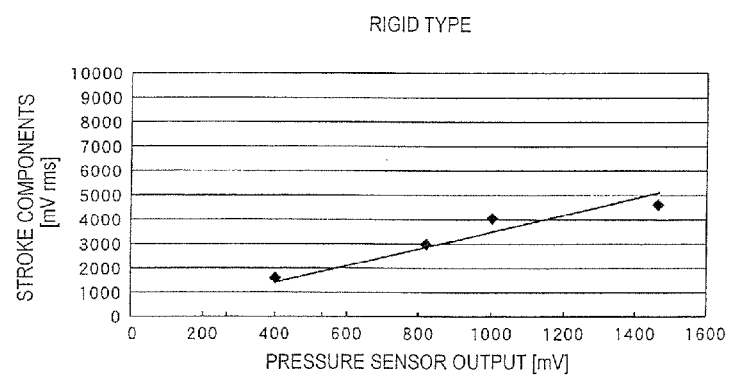
FIG. 87 is an explanatory diagram of the relationship between a rigid type of blood vessel simulation sensor and the body motion components (stroke components) included in the pulse wave sensor output.

FIG. 87 is an explanatory diagram of the relationship between the rigid type of blood vessel simulation sensor 150 or 160 and the body motion components (stroke components) included in the output of the pulse wave sensor 83. As shown in FIG. 87, it is clear that the output of the rigid type of blood vessel simulation sensor 150 or 160 has a substantially proportional correlation with the size of the body motion components (stroke components) included in the output of the pulse sensor 83.

Figure 88:
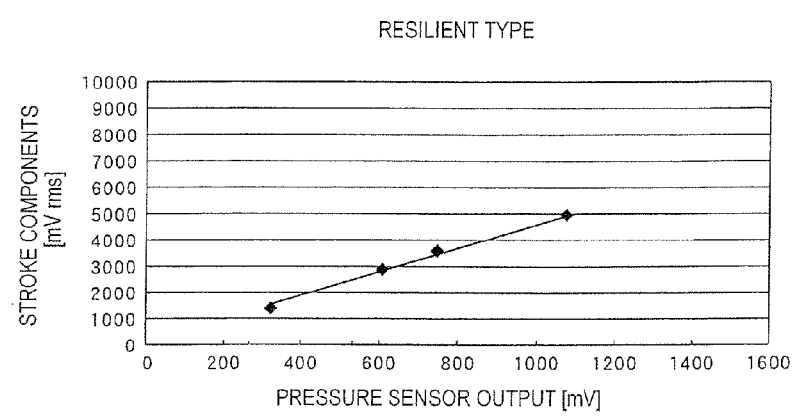
FIG. 88 is an explanatory diagram of the relationship between an elastic type of blood vessel simulation sensor and the body motion components (stroke components) included in the pulse sensor output.

FIG. 88 is an explanatory diagram of the relationship between the elastic type of blood vessel simulation sensor 170 or 180 and the body motion components (stroke components) included in the output of the pulse sensor 83. As shown in FIG. 88, it is clear that the output of the elastic type of blood vessel simulation sensor 170 or 180 has a substantially proportional correlation with the size of the body motion components (stroke components) included in the output of the pulse wave sensor 83, similar to the output of the rigid type of blood vessel simulation sensor 150 or 160.

Therefore, it is clear that when the body motion components (stroke components) included in the output signal of the pulse wave sensor 83 are assumed to be primarily determined by the movement of venous blood, it is possible to estimate the amount of body motion components contained in the output signal of the pulse wave sensor using any of the blood vessel simulation sensors 150 through 180 or an acceleration sensor type of blood vessel simulation sensor.

Figure 89:
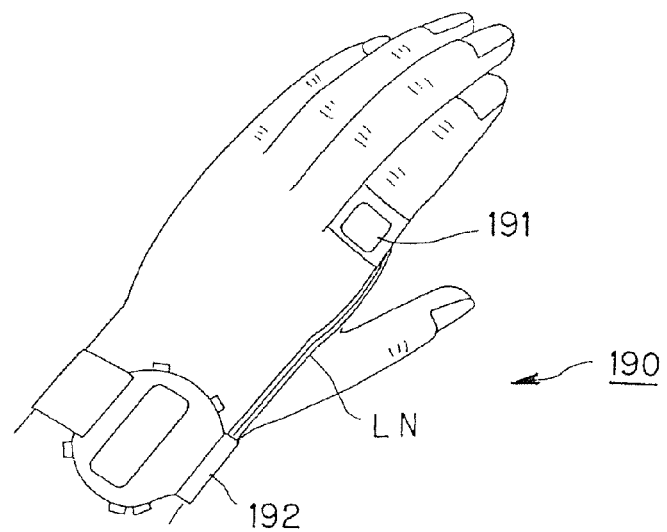
FIG. 89 is a schematic structural block diagram of a pulse measurement device of the fourth embodiment.

The fourth embodiment will now be described in detail. FIG. 89 is a schematic structural block diagram of a pulse measurement device 190 of the fourth embodiment.

In general terms, the pulse measurement device 190 has a sensor module 191 mounted on the finger of the user, and a device main body 192 connected to the sensor module 191 via a wiring LN and mounted on the arm of the user.

Figure 90:
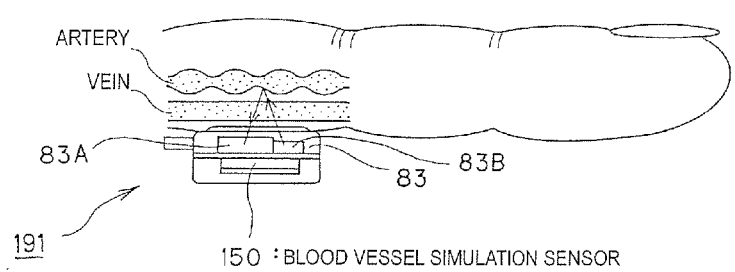
FIG. 90 is an explanatory diagram of the arrangement of the sensors in a sensor module of the pulse measurement device of the fourth embodiment in a mounted state.

FIG. 90 is an explanatory diagram of the arrangement of the sensors in the sensor module in a mounted state. In general terms, the sensor module 191 is configured with a pulse wave sensor 83 for primarily detecting pulse wave components and a blood vessel simulation sensor described above for primarily detecting body motion components. In the fourth embodiment, the first rigid type of blood vessel simulation sensor 150 is used as the blood vessel simulation sensor. In this case, the first rigid type of blood vessel simulation sensor 150 is disposed near the pulse wave sensor 83 and is also disposed in a substantially layered state over the pulse wave sensor 83 in a direction away from the user (the body). The pulse wave sensor 83 referred to herein has an LED 83A for emitting detection light and a PD 83B for receiving the detection light reflected by the body.

Figure 91:
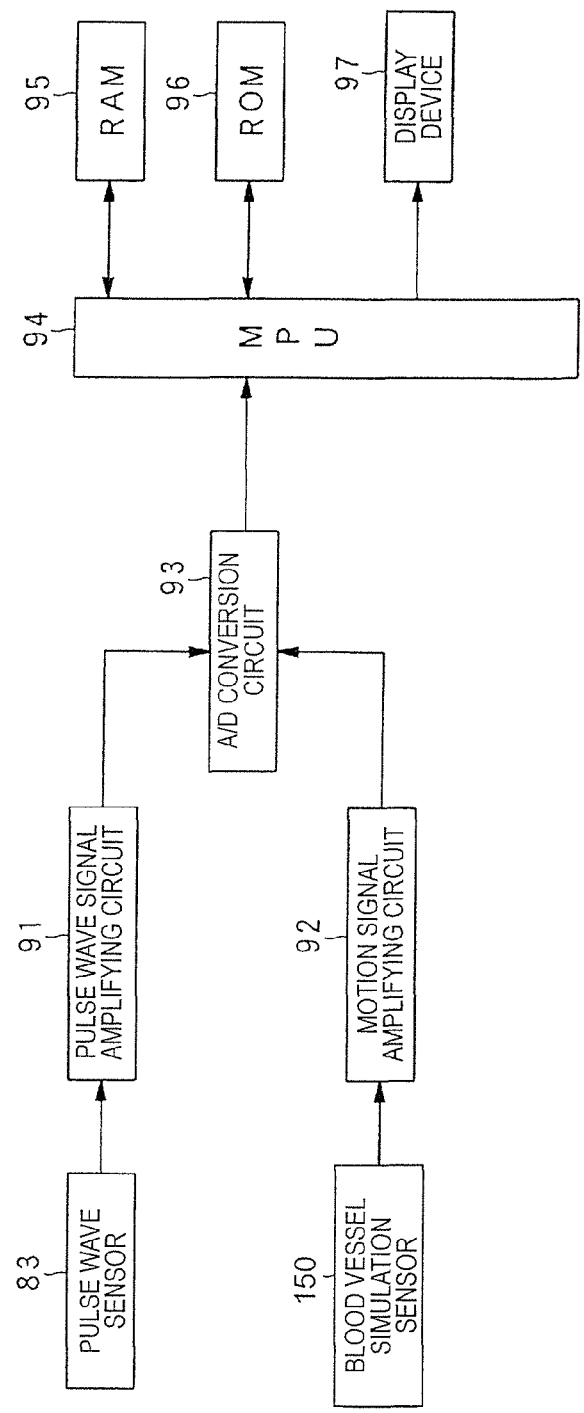
FIG. 91 is a schematic structural block diagram of the pulse measurement device of the fourth embodiment.

FIG. 91 is a schematic structural block diagram of the pulse measurement device 190. In general terms, the pulse measurement device 190 has, in addition to the pulse wave sensor 83 described above, a blood vessel simulation sensor 150 as a body motion sensor, a pulse wave signal amplifying circuit 91, a body motion signal amplifying circuit 92, an A/D conversion circuit 93, an MPU 94, a RAM 95, a ROM 96, and a display device 97.

The pulse wave signal amplifying circuit 91 amplifies the pulse wave detection signal outputted from the pulse wave sensor 83 at a prescribed rate of amplification, and outputs the result as an amplified pulse wave detection signal to the A/D conversion circuit 93.

The body motion signal amplifying circuit 92 amplifies the pressure detection signal based on the movement of the simulation blood 152 and outputted from the first rigid type of blood vessel simulation sensor 150 functioning as a body motion sensor at a specific rate, and outputs the result as an amplified pressure detection signal to the A/D conversion circuit 93.

The A/D conversion circuit 93 performs analog/digital conversion separately on the inputted amplified pulse wave detection signal and the amplified pressure detection signal, and outputs the result as detected pulse wave data and detected pressure data to the MPU 94.

The MPU 94 stores the detected pulse wave data and detected pressure data (detected body motion data) for the pressure detection signal outputted from the first rigid type of blood vessel simulation sensor 150 in the RAM 95, calculates the pulse rate based on a control program stored in the ROM 96, and displays the result on the display device 97.

More specifically, the MPU 94 chronologically arranges the detected pulse wave data and the detected pressure data (detected body motion data) stored in the RAM 95 and determines the differential data, which is the difference between the detected pulse wave data and the detected pressure data for each corresponding sampling time.

Frequency analysis (FFT: Fast Fourier Transformation) is then performed on the differential data, the harmonic components of the pulse wave are extracted, and the pulse rate is calculated from the frequency.

The specific pulse rate calculation process will now be described.

Figure 92:
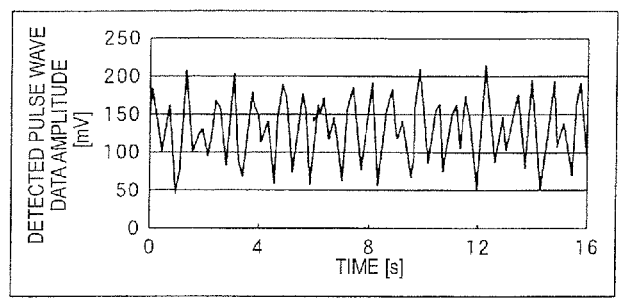
FIG. 92 is a graph of a chronological arrangement of one example of the detected pulse wave data according to the fourth embodiment.
Figure 93:
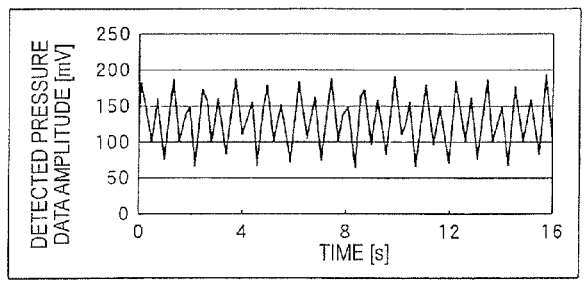
FIG. 93 is a graph in which detected pressure data correlated with the detected pulse wave data in FIG. 92 is chronologically arranged along the same time axis.

FIG. 92 is a graph of a chronological arrangement of one example of the detected pulse wave data. FIG. 93 is a graph in which detected pressure data correlated with the detected pulse wave data in FIG. 92 is chronologically arranged along the same time axis.

First, the MPU 94 sequentially reads out the detected pulse wave data and the detected pressure data stored in the RAM 95 and calculates the differential data by subtracting the detected pressure data in a certain sampling period from the detected pulse wave data at the same sampling timing.

Figure 94:
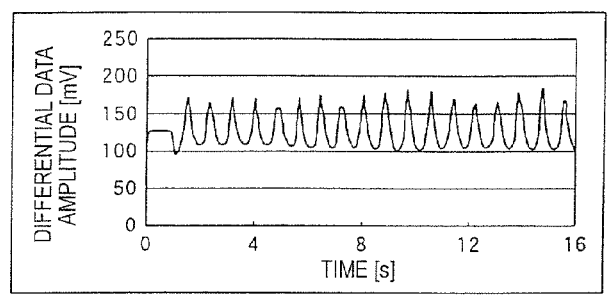
FIG. 94 is a graph of a chronological arrangement of differential data calculated from the detected pulse wave data in FIG. 92 and the detected pressure data in FIG. 93.

FIG. 94 is a graph of a chronological arrangement of differential data calculated from the detected pulse wave data in FIG. 92 and the detected pressure data in FIG. 93.

Next, the MPU 94 subjects the differential data to FFT.

Figure 95:
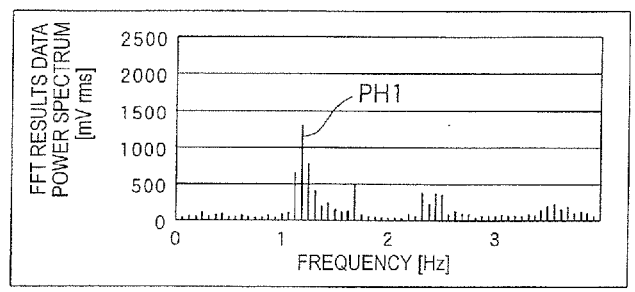
FIG. 95 shows the frequency analysis results obtained by subjecting the differential data in FIG. 94 to FFT.

FIG. 95 shows the frequency analysis results obtained by subjecting the differential data in FIG. 94 to FFT.

Thus, the frequency analysis results thus obtained have the body motion components originating in the veins substantially removed from the output signal (pulse wave components+body motion components) of the pulse wave sensor 83, and are, specifically, pulse wave data that primarily corresponds to the pulse wave components.

Furthermore, the MPU 94 calculates the pulse rate from the frequency on the assumption that the maximum frequency components of the resulting pulse wave data constitute the pulse spectrum PH1.

The MPU 94 then displays the pulse rate on the display device 97.

As described above, according to the fourth embodiment, variation in the veins, which is the main factor in the body motion components generated in the body, can be accurately estimated based on the output signal from the blood vessel simulation sensor. Therefore, the body motion components can be accurately removed, making it possible to accurately detect pulse wave components, and hence to accurately measure the pulse rate.

The fourth embodiment describes the first rigid type of blood vessel simulation sensor 150 used as the rigid type of blood vessel simulation sensor, but the second rigid type of blood vessel simulation sensor 160 may also be used.

(4.1) First Alternative of the Fourth Embodiment

A first alternative of the fourth embodiment is similar to the fourth embodiment except that the fourth embodiment uses a configuration in which differential data is calculated by subtracting detected pressure data, which corresponds to the pressure detection signal outputted from the first rigid type of blood vessel simulation sensor 150, from the detected pulse wave data prior to frequency analysis (FFT), while the first alternative uses a configuration in which the differential data is calculated after frequency analysis is performed on the detected pulse wave data and on the detected pressure data that corresponds to the pressure detection signal outputted from the first rigid type of blood vessel simulation sensor 150.

In the first alternative of the fourth embodiment, the MPU 94 performs frequency analysis (FFT) separately on the detected pulse wave data and the detected pressure data (detected body motion data) that corresponds to the pressure detection signal outputted from the first rigid type of blood vessel simulation sensor 150 stored in the RAM 95.

Next, the MPU 94 determines the differential data, which is the difference between the detected pulse wave data after analyzed for frequency and the detected pressure data after analyzed for frequency. The harmonic components of the pulse wave are then extracted from the resulting differential data, and the pulse rate is calculated from the frequency thereof.

A more specific pulse rate calculation process will now be described.

Figure 96:
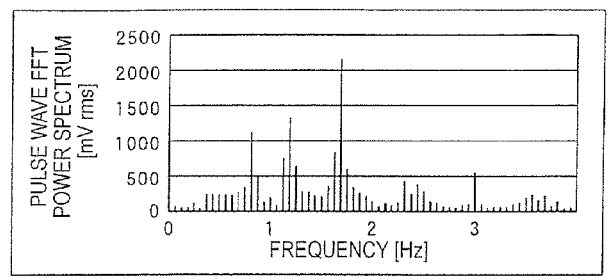
FIG. 96 is an explanatory diagram of the frequency analysis results of the detected pulse wave data in a first alternative of the fourth embodiment.

FIG. 96 is an explanatory diagram of the frequency analysis results for detected pulse wave data.

Figure 97:
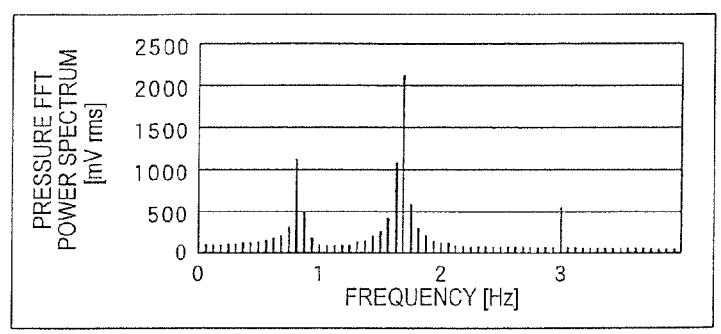
FIG. 97 is an explanatory diagram of the frequency analysis results of detected pressure data.

FIG. 97 is an explanatory diagram of the frequency analysis results for detected pressure data that corresponds to the pressure detection signal outputted from the first rigid type of blood vessel simulation sensor 150.

First, the MPU 94 sequentially reads out the detected pulse wave data and the detected pressure data stored in the RAM 95, and subjects them to FFT.

Figure 98:
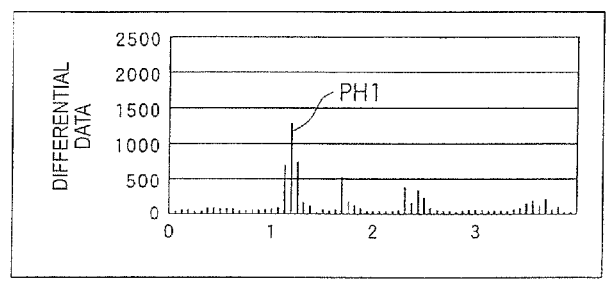
FIG. 98 is an explanatory diagram of differential data, which is the difference between detected pulse wave data after analyzed for frequency and detected pressure data after analyzed for frequency.

FIG. 98 is an explanatory diagram of differential data, which is the difference between the detected pulse wave data after analyzed for frequency and the detected pressure data after analyzed for frequency.

Next, the MPU 94 compares the detected pulse wave data after analyzed for frequency with the detected pressure data after analyzed for frequency, and determines the difference between these frequency components to create the differential data.

Thus, the frequency analysis results thus obtained as the differential data have the body motion components originating in the veins substantially removed from the output signal (pulse wave components+body motion components) of the pulse wave sensor, and are, specifically, pulse wave data that primarily corresponds to the pulse wave components.

Furthermore, the MPU 94 calculates the pulse rate from the frequency on the assumption that the maximum frequency components of the resulting pulse wave data constitute the pulse spectrum PH1.

The MPU 94 then displays the pulse rate on the display device 97.

As described above, according to the first alternative of the fourth embodiment, variation in the veins, which is the main factor of the body motion components generated in the body, can be surely estimated with a blood vessel simulation sensor. Therefore, the body motion components can be surely removed, making it possible to accurately detect pulse wave components, and hence to accurately measure the pulse rate.

(4.2) Second Alternative of the Fourth Embodiment

A second alternative of the fourth embodiment is similar to the fourth embodiment except that the fourth embodiment uses a configuration in which differential data is calculated by subtracting detected pressure data, which corresponds to the pressure detection signal outputted from the first rigid type of blood vessel simulation sensor 150, from the detected pulse wave data prior to frequency analysis (FFT), while the second alternative uses a configuration in which the MPU 94 has an adaptive filter 200, and the body motion components that correspond to the pressure detection signal outputted from the blood vessel simulation sensor 150 are removed from the detected pulse wave data.

Figure 99:
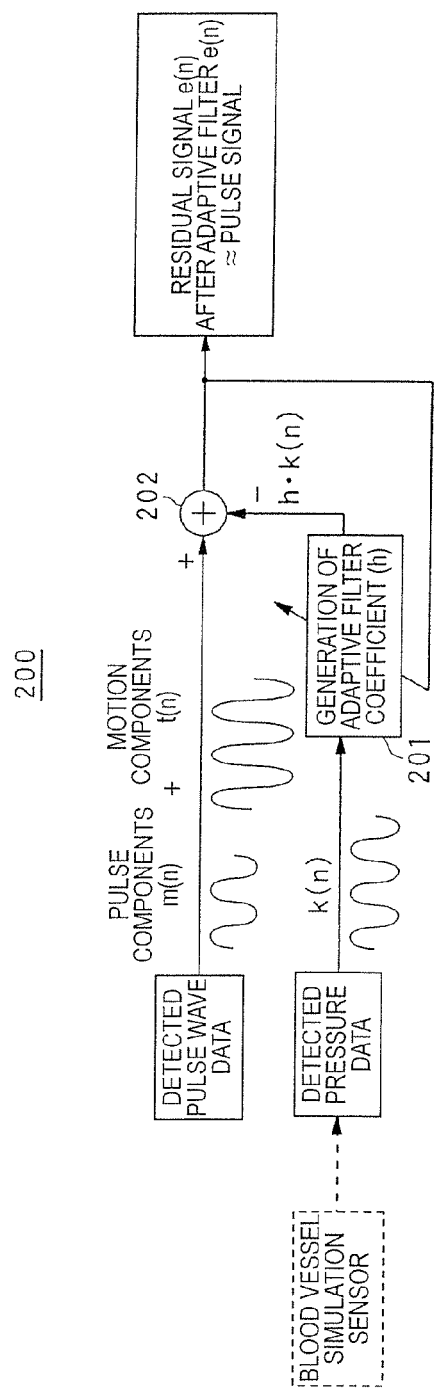
FIG. 99 is a schematic structural block diagram of one example of an adaptive filter in a second alternative of the fourth embodiment.

FIG. 99 is a schematic structural block diagram of one example of the adaptive filter 200. In general terms, the adaptive filter 200 has a filter coefficient generating section 201 and a synthesizer 202.

The filter coefficient generating section 201 functions as a body motion component removing section and generates the adaptive filter coefficient h based on data previously outputted by the synthesizer 202 to which the filter has been applied. The adaptive filter coefficient h is then applied to the detected pressure data (=k(n)), which functions as the body motion component detection signal inputted from the blood vessel simulation sensor; body motion removal data (=h·k(n)) is generated; and this data is outputted to the synthesizer 202.

The synthesizer 202 functions as a removal processing section, combines the extracted detected pulse wave data (=pulse wave components+body motion components) and the body motion removal data, substantially removes (subtracts) the body motion components contained in the current detected pulse wave data, and extracts pulse wave components.

A more specific pulse rate calculation process according to the second alternative will now be described.

Figure 100:
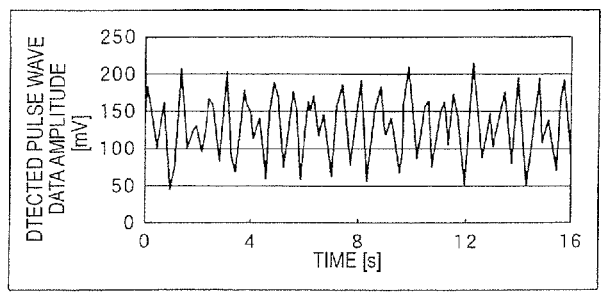
FIG. 100 is a graph of a chronological arrangement of one example of the detected pulse wave data in the second alternative of the fourth embodiment.
Figure 101:
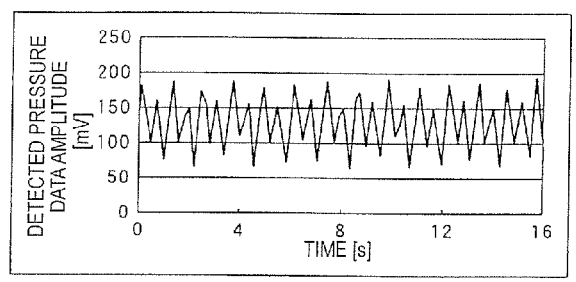
FIG. 101 is a graph in which pressure detection data correlated with the detected pulse wave data in FIG. 100 is chronologically arranged along the same time axis.

FIG. 100 is a graph of a chronological arrangement of an example of the detected pulse wave data. FIG. 101 is a graph in which the detected pressure data inputted from the blood vessel simulation sensor and correlated with the detected pulse wave data in FIG. 100 is chronologically arranged along the same time axis.

First, the MPU 94 sequentially reads out the detected pulse wave data and the detected pressure data stored in the RAM 95, and outputs the detected pulse wave data in a certain sampling period to the synthesizer 202.

Also, the MPU 94 presents the filter coefficient generating section 201 with detected pressure data that corresponds to the detected pulse wave data.

Thus, the filter coefficient generating section 201 creates an adaptive filter coefficient h based on the data previously outputted from the synthesizer 202 to which the adaptive filter has been applied. The adaptive filter coefficient h is then applied to the detected pressure data (=k(n)) functioning as the body motion component detection signal inputted from a result simulation sensor, and body motion removal data (=h·k (n)) is outputted to the synthesizer 202.

Thus, the synthesizer 202 combines the current pulse wave data and the body motion removal data, substantially removes (subtracts) the body motion components contained in the current detected pulse wave data, extracts the pulse wave components, and outputs the residual data (=data to which the filter has been applied).

Figure 102:
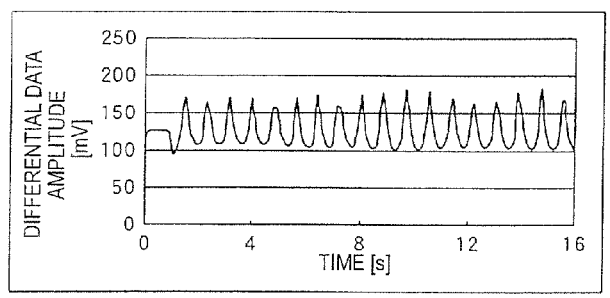
FIG. 102 is a graph of a chronological arrangement of differential data obtained by applying an adaptive filter to the detected pulse wave data in FIG. 100 and the detected pressure data in FIG. 20.

FIG. 102 is a graph of a chronological arrangement of residual data obtained by applying an adaptive filter to the detected pulse wave data in FIG. 100 and the detected pressure data outputted from the blood vessel simulation sensor in FIG. 101.

Next, the MPU 94 subjects the residual data to FFT.

Figure 103:
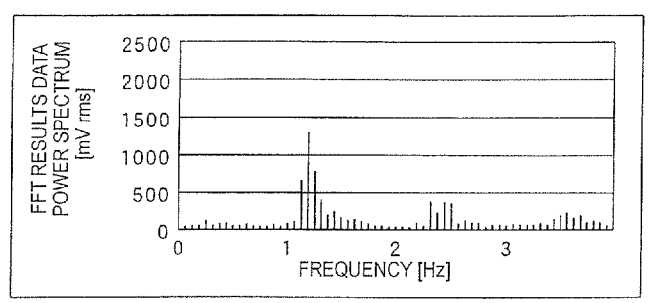
FIG. 103 shows the frequency analysis results obtained by subjecting the differential data in FIG. 102 to FFT.

FIG. 103 shows the frequency analysis results obtained by subjecting the residual data in FIG. 102 to FFT.

Thus, the frequency analysis results thus obtained have the body motion components originating in the veins, which are estimated based on the blood vessel simulation sensor output, substantially removed from the output signal (pulse wave components+body motion components) of the pulse wave sensor, and are, specifically, pulse wave data that primarily corresponds to the pulse wave components.

Furthermore, the MPU 94 calculates the pulse rate from the frequency on the assumption that the maximum frequency components of the resulting pulse wave data that primarily contains pulse wave components constitute the pulse spectrum.

The MPU 94 then displays the pulse rate on the display device 97.

As described above, according to the second alternative of the fourth embodiment, variation in the veins, which is the main factor of the body motion components generated in the body, can be surely estimated with a blood vessel simulation sensor, whereby the body motion components can be accurately removed, making it possible to surely detect pulse wave components, and hence to accurately measure the pulse rate.

(4.3) Third Alternative of the Fourth Embodiment

A third alternative of the fourth embodiment will now be described. The third alternative of the fourth embodiment is similar to the fourth embodiment, except that the sensor module 191 having the rigid type of blood vessel simulation sensor 150 in the fourth embodiment is replaced by a sensor module 191A having a resilient type of blood vessel simulation sensor 170.

Figure 104A:
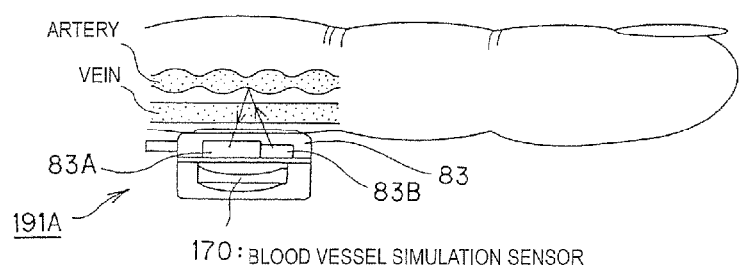
FIG. 104A is an explanatory diagram of the arrangement of sensors in a sensor module of a mounted pulse measurement device according to a third alternative of the fourth embodiment, in a mounted state.
Figure 104B:
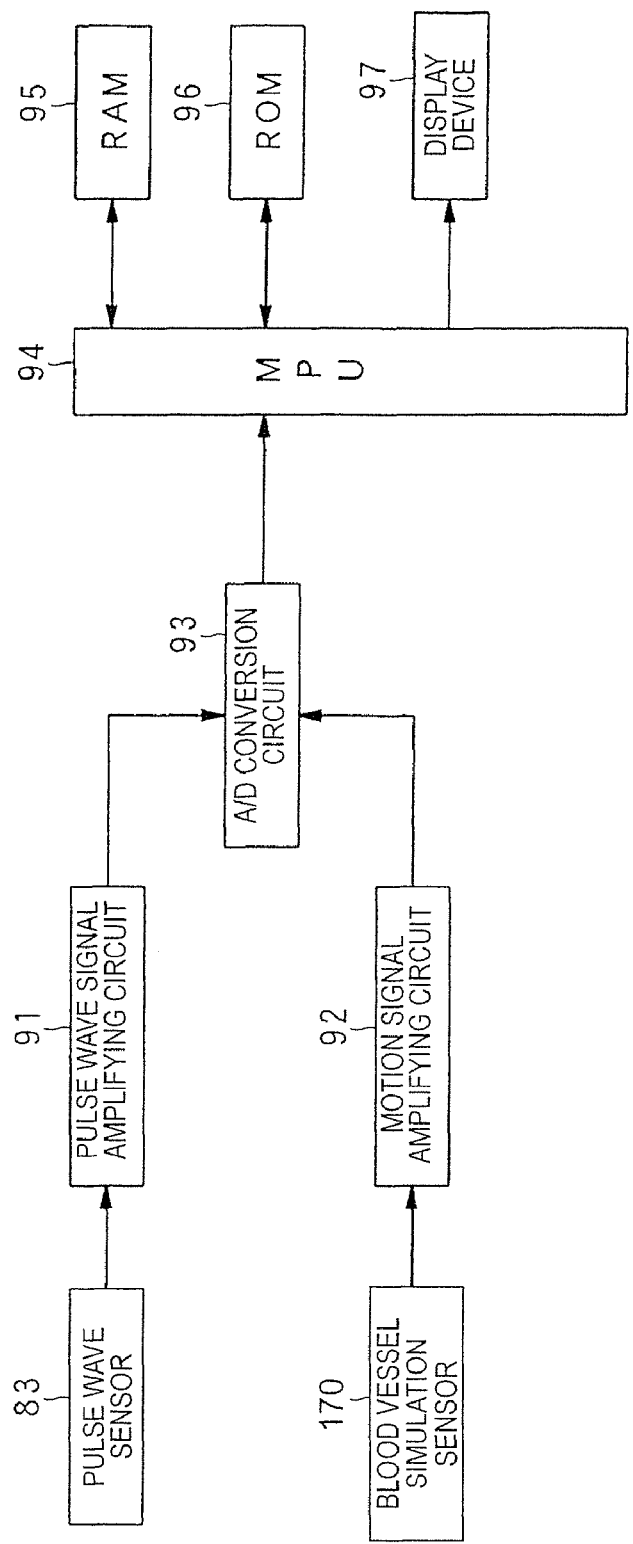
FIG. 104B is a schematic structural block diagram of the pulse measurement device according to the third alternative of the fourth embodiment.

FIG. 104A is an explanatory diagram of the arrangement of sensors in the sensor module 191A in a mounted state. FIG. 104B is a schematic structural block diagram of the pulse measurement device according to the third alternative of the fourth embodiment.

As shown in FIG. 104A, in general terms, the sensor module 191A is configured to include the pulse wave sensor 83 for primarily detecting pulse wave components, and the first resilient type of blood vessel simulation sensor 170 described above for primarily detecting body motion components.

Such a configuration makes it possible to surely estimate body motion components generated in the body and to remove the body motion components in a more similar to the actual veins.

The third alternative of the fourth embodiment describes the use of the first elastic type of blood vessel simulation sensor 170 as an elastic type of blood vessel simulation sensor, but a second elastic type of blood vessel simulation sensor 180 may also be used.

(4.4) Fourth Alternative of the Fourth Embodiment

A fourth alternative of the fourth embodiment will now be described. The fourth alternative of the fourth embodiment is similar to the fourth embodiment, except that the sensor module 191 having the rigid type of blood vessel simulation sensor 150 in the fourth embodiment is replaced by a sensor module 191B having an acceleration sensor 210 as a blood vessel simulation sensor.

Figure 105A:
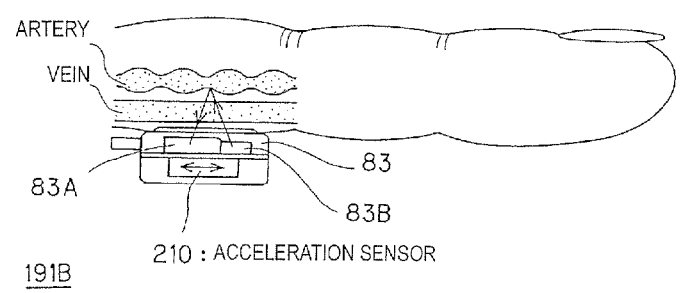
FIG. 105A is an explanatory diagram of the arrangement of sensors in a sensor module of a pulse measurement device according to a fourth alternative of the fourth embodiment, in a mounted state.
Figure 105B:
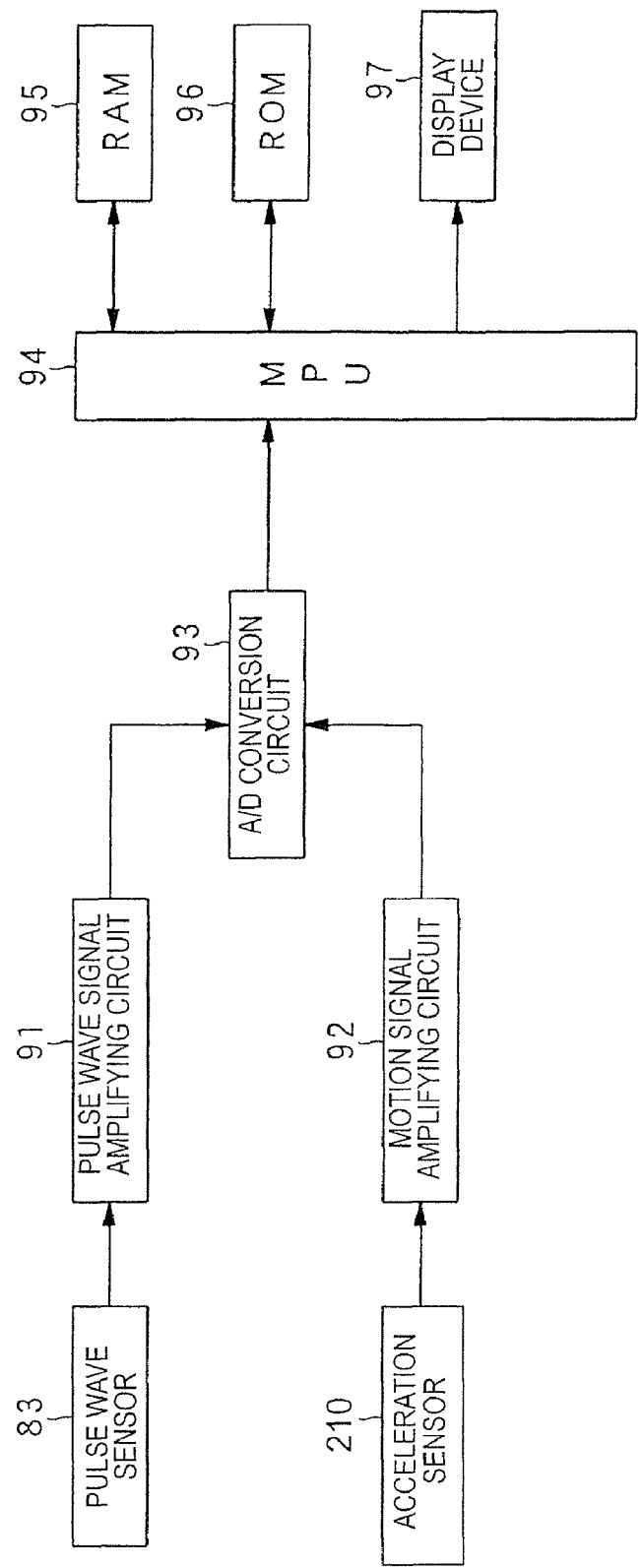
FIG. 105B is a schematic structural block diagram of the pulse measurement device according to the fourth alternative of the fourth embodiment.

FIG. 105A is an explanatory diagram of the arrangement of sensors in the sensor module 191B in a mounted state. FIG. 105B is a schematic structural block diagram of the pulse measurement device according to the fourth alternative of the fourth embodiment.

As shown in FIG. 105A, in general terms, the sensor module 191B is configured having a pulse wave sensor 83 for primarily detecting pulse wave components, and the acceleration sensor 210 for primarily detecting acceleration in the peripheral direction shown in FIG. 82.

In this case, the acceleration sensor 210 as the blood vessel simulation sensor is disposed near the pulse wave sensor 83 and is also disposed in a substantially layered state over the pulse wave sensor 83 in a direction away from the user (the body).

The configuration of the acceleration sensor 210 will now be examined in detail.

Figure 106:
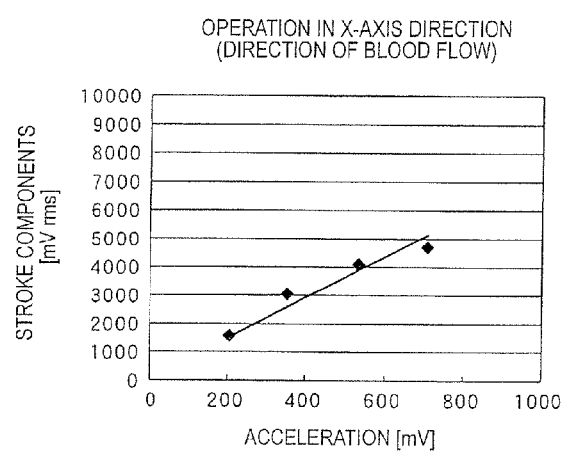
FIG. 106 is an explanatory diagram of the relationship between acceleration in the direction of the X-axis described hereinbelow, when a triaxial (X, Y, Z-axes) acceleration sensor is used as an acceleration sensor, and the body motion components (stroke components) included in the pulse wave sensor output signal.

FIG. 106 is an explanatory diagram of the relationship between acceleration in the direction of the X-axis described hereinbelow when a triaxial (X, Y, Z-axes) acceleration sensor is used as the acceleration sensor, and the body motion components (stroke components) included in the output signal of the pulse wave sensor 83.

Figure 107:
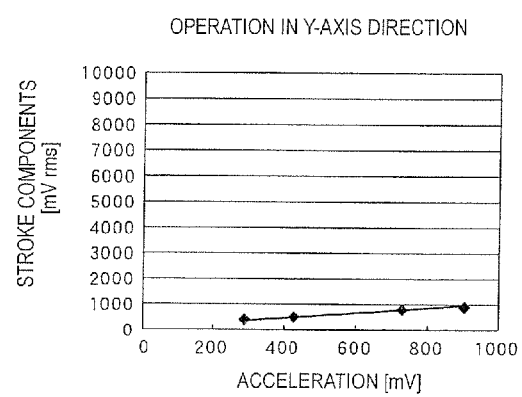
FIG. 107 is an explanatory diagram of the relationship between acceleration in the direction of the Y-axis described hereinbelow, when a triaxial acceleration sensor described hereinbelow is used as an acceleration sensor, and the body motion components (stroke components) included in the pulse wave sensor output signal.

FIG. 107 is an explanatory diagram of the relationship between acceleration in the direction of the Y-axis described hereinbelow when a triaxial acceleration sensor described hereinbelow is used as the acceleration sensor, and the body motion components (stroke components) included in the output signal of the pulse wave sensor 83.

Figure 108:
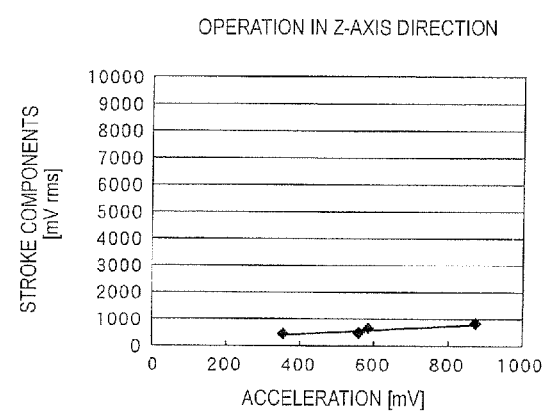
FIG. 108 is an explanatory diagram of the relationship between acceleration in the direction of the Z-axis, when a triaxial (X, Y, Z-axes) acceleration sensor described hereinbelow is used as an acceleration sensor, and the body motion components (stroke components) included in the pulse wave sensor output signal.

FIG. 108 is an explanatory diagram of the relationship between acceleration in the direction of the Z-axis described hereinbelow when a triaxial (X, Y, Z-axes) acceleration sensor described hereinbelow is used as the acceleration sensor, and the body motion components (stroke components) included in the output signal of the pulse wave sensor 83.

Figure 109:
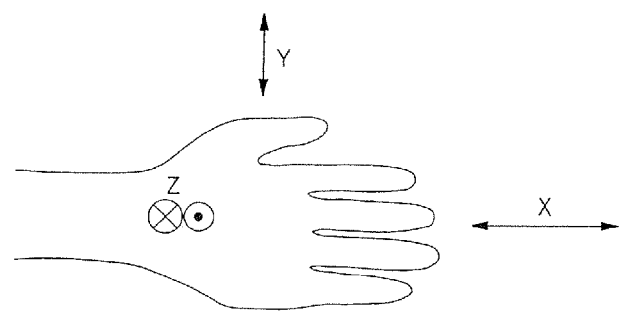
FIG. 109 is an explanatory diagram of the three axes.

FIG. 109 is an explanatory diagram of the three axes. As shown in FIG. 109, the X-axis extends in the peripheral direction (direction of the fingertips) shown in FIG. 82, the Y-axis is perpendicular to and lies in the same plane as the X-axis when the palm of the hand is aligned in this plane, and the Z-axis is perpendicular to the plane containing the palm of the hand.

As shown in FIGS. 106 through 108, it is clear that the body motion components contained in the output signal of the pulse wave sensor 83 are primarily based on components in the X-axis direction. Therefore, it is possible to estimate the body motion components detected by the pulse wave sensor 83 if a uniaxial acceleration sensor capable of detecting acceleration only in the X-axis direction, or, specifically, in the peripheral direction shown in FIG. 82, is used as the acceleration sensor 210.

(5) Fifth Embodiment

A pulse measurement device 220 according to a fifth embodiment of the present invention will now be described with reference to FIGS. 110 and 111. The main difference between the fourth embodiment and the fifth embodiment is that in the fourth embodiment, the pulse wave sensor 83 and the blood vessel simulation sensor 150 are configured integrally as the sensor module 191, while in the fifth embodiment, the blood vessel simulation sensor 150 is incorporated into the main body of the device. Otherwise the basic configuration is similar to the fourth embodiment; therefore, in view of the similarity between the fourth embodiment and the fifth embodiment, descriptions of the parts of the fifth embodiment with identical or similar functions to the parts of the fourth embodiment may be omitted for the sake of simplicity.

Figure 110:
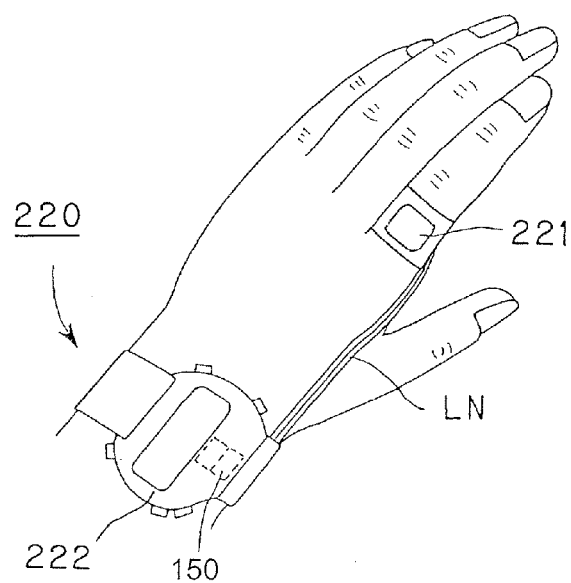
FIG. 110 is an external perspective view of a pulse measurement device of a fifth embodiment.

FIG. 110 is an external perspective view of the pulse measurement device 220 of the fifth embodiment. FIG. 111 is a cross-sectional view of a sensor module 221 in FIG. 110.

In general terms, the pulse measurement device 220 has the sensor module 221 mounted on the finger of the user, and a device main body 222 connected to the sensor module 221 via a wiring LN and mounted on the arm of the user.

Figure 111:
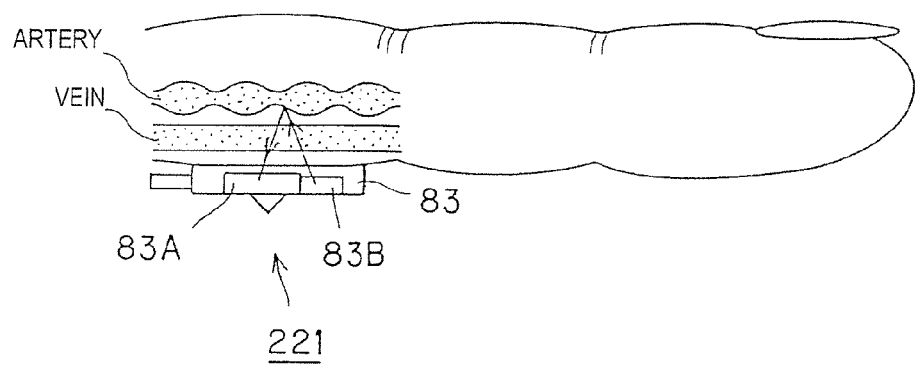
FIG. 111 is a cross-sectional view of the sensor module in FIG. 110.

As shown in FIG. 111, in general terms, the sensor module 221 is configured having a pulse wave sensor 83 for primarily detecting pulse wave components.

The pulse wave sensor 83 has an LED 83A for emitting detection light and a PD 83B for receiving the detection light reflected by the body.

Also, as shown in FIG. 110, the blood vessel simulation sensor 150 is accommodated in the device main body 222 in such a state that the sensitivity axis virtually coincides with the peripheral direction of the body (direction of the fingertips).

Since the specific operation of the fifth embodiment is similar to the fourth embodiment, a detailed description is omitted.

As described above, according to the fifth embodiment, in addition to the effects of the fourth embodiment, finger movements and other such small movements are not erroneously detected by the blood vessel simulation sensor 150, the size of the sensor module can be reduced, mounting is made easier, and the user's sensation of wearing the device is improved because the blood vessel simulation sensor 150 is incorporated into the main body of the device.

A case of using the first rigid type of blood vessel simulation sensor 150 as a body motion sensor was described above as an example, but it is also possible to use the second rigid type of blood vessel simulation sensor, the first elastic type of blood vessel simulation sensor 170, the second resilient type of blood vessel simulation sensor 180, or the acceleration sensor 210 as a blood vessel simulation sensor for the body motion sensor instead of the first rigid type of blood vessel simulation sensor 150. Also in such cases, finger movements and other such small movements are not erroneously detected, the size of the sensor module is reduced, mounting is made easier, and the user's sensation of wearing the device is improved by incorporating the sensor used as the body motion sensor into the main body of the device.

(6) Sixth Embodiment

A pulse measurement device 230 according to a sixth embodiment of the present invention will now be described with reference to FIGS. 112 and 113. The main difference between the fourth embodiment and the sixth embodiment is that in the fourth embodiment, the sensor module 191 and the device main body 192 are provided separately and are connected by wiring, while in the sixth embodiment, the sensor module is incorporated into the main body of the device. Otherwise the basic configuration is similar to the fourth embodiment; therefore, in view of the similarity between the fourth embodiment and the sixth embodiment, descriptions of the parts of the sixth embodiment with identical or similar functions to the parts of the fourth embodiment may be omitted for the sake of simplicity.

Figure 112:
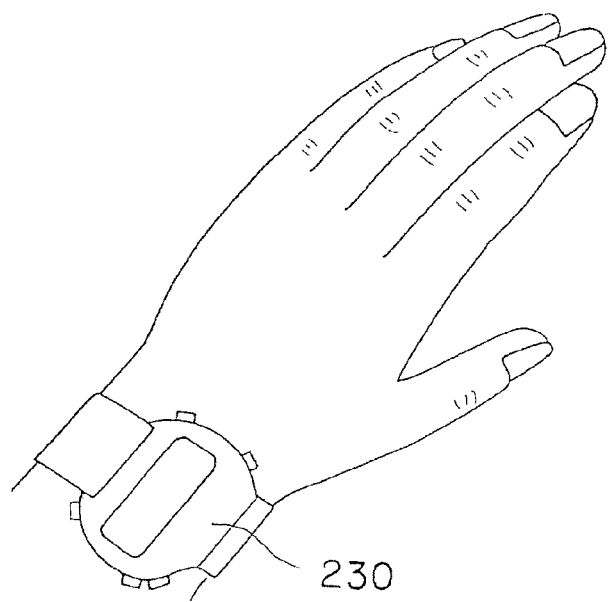
FIG. 112 is an external perspective view of a case in which a pulse measurement device of a sixth embodiment is incorporated in a watchcase.
Figure 113:
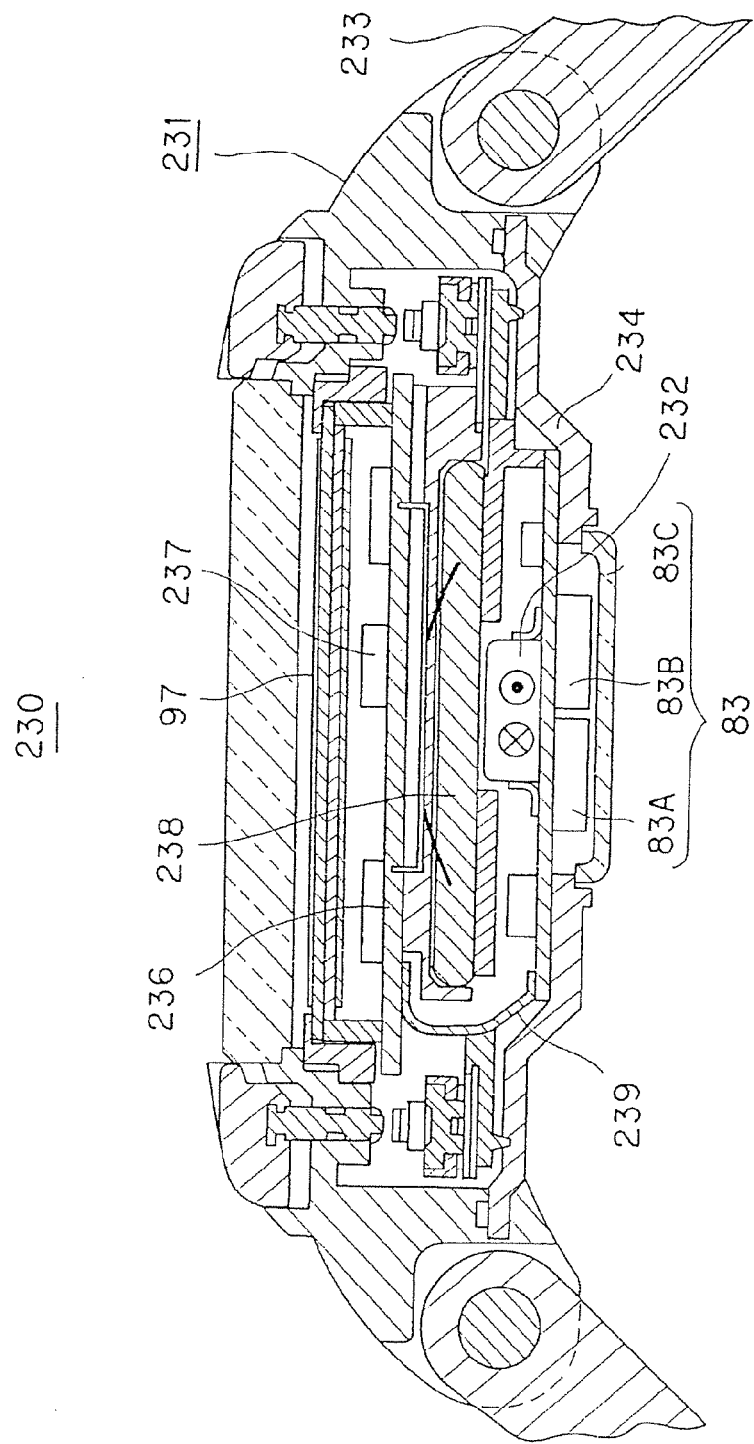
FIG. 113 is a cross-sectional view of the pulse measurement device in FIG. 112.

FIG. 112 is an external perspective view of a case in which the pulse measurement device 230 of the sixth embodiment is incorporated in a watchcase. FIG. 113 is a cross-sectional view of the pulse measurement device 230 in FIG. 112.

In this example, the pulse wave sensor 83 and a blood vessel simulation sensor 232 are provided on the reverse surface of a watchcase 231. As shown in FIG. 113, the pulse wave sensor unit 83 described above is formed integrally with the main body on the reverse side of the watchcase 231. The watchcase 231 is provided with a wristband 233 for mounting the watchcase 231 on the arm, and the reverse side of the watchcase 231 is pressed against the back of the wrist when the wristband 233 is wound around the wrist.

The transparent glass 83C constituting the pulse wave sensor 83 is fixed to the reverse side of the watchcase 231 by a back lid 234. In addition to protecting the LED 83A and the PD 83B of the pulse wave sensor 83, the transparent glass 83C transmits the light cast on the LED 83A, transmits reflected light obtained via the body, and directs the light to the PD 83B. The front side of the watchcase 231 is provided with a liquid crystal display device or another such display device 97 for displaying the pulse rate HR and other such living organism information based on the detection results from the pulse wave sensor 83 in addition to the current time and date. Also, the interior of the watchcase 231 has a CPU and other such IC circuits on a main board 236, whereby a data processing circuit 237 is configured.

Also, the reverse side of the main board 236 is provided with a battery 238, and the battery 238 supplies power to the display device 97, the main board 236, the pulse wave sensor 83, and the blood vessel simulation sensor 232.

The main board 236 and the pulse wave sensor 83 are connected by a heat seal 239, power is supplied from the main board 236 to the pulse wave sensor 83 through a wiring formed by the heat seal 239, and a pulse wave detection signal is fed from the pulse wave sensor 83 to the main board 236.

The data processing circuit 237 subjects the pulse wave signal to FFT processing, and the pulse rate HR is calculated by analyzing the processing results. The external surface of the watchcase 231 is provided with button switches (not shown) for time setting, display mode switching, and the like.

The reverse side of the watchcase 231 faces the back of the wrist when the wristband 233 is wound around the wrist. Therefore, the light from the LED 83A is directed to the back of the wrist via the transparent glass 83C, and the reflected light is received by the photo diode 83B.

Since the specific operation of the sixth embodiment is similar to the fourth embodiment, a detailed description is omitted.

As described above, according to the sixth embodiment, in addition to the effects of the fourth embodiment, finger movements and other such small movements are not erroneously detected and mounting is made easier because the sensor module is incorporated into the main body of the device.

A case of using the blood vessel simulation sensor 232 as a body motion sensor was described above as an example, but it is also possible to use the first rigid type of blood vessel simulation sensor 150, a second rigid type of blood vessel simulation sensor, the first resilient type of blood vessel simulation sensor 170, the second resilient type of blood vessel simulation sensor 180, or the acceleration sensor 210 as a blood vessel simulation sensor for the body motion sensor instead of the blood vessel simulation sensor 232. Also in such cases, finger movements and other such small movements are not erroneously detected and mounting is made easier by incorporating the sensor used as the body motion sensor into the main body of the device.

In the above descriptions of the first embodiment through the sixth embodiment, a case of storing a control program in the ROM 26 or the ROM 96 in advance was described, but another possibility is a configuration in which the control program is stored in advance on various magnetic disks, optical disks, memory cards, and other such storage media, and is read from these storage media and installed. Another possibility is a configuration in which a communication interface is provided for downloading the control program via the Internet, LAN, or another such network; installing the program; and running this program.

The term "configured" as used herein to describe a component, section or part of a device includes hardware and/or software that is constructed and/or programmed to carry out the desired function.

As used herein, the following directional terms "forward, rearward, above, downward, vertical, horizontal, below and transverse" as well as any other similar directional terms refer to those directions of any pulse measurement device equipped with the present invention. Accordingly, these terms, as utilized to describe the present invention should be interpreted relative to any pulse measurement device equipped with the present invention.

The terms of degree such as "substantially", "about" and "approximately" as used herein mean a reasonable amount of deviation of the modified term such that the end result is not significantly changed. For example, these terms can be construed as including a deviation of at least ±5% of the modified term if this deviation would not negate the meaning of the word it modifies.

This specification claims priority to Japanese Patent Application Nos. 2003-75839, 2003-75840, and 2003-310624. All of the disclosures in Japanese Patent Application Nos. 2003-75839, 2003-75840, and 2003-310624 are incorporated herein by reference.

While only selected embodiments have been chosen to illustrate the present invention, it will be apparent to those skilled in the art from this disclosure that various changes and alternatives can be made herein without departing from the scope of the invention as defined in the appended claims. Furthermore, the foregoing descriptions of the embodiments according to the present invention are provided for illustration only, and not for the purpose of limiting the invention as defined by the appended claims and their equivalents. Thus, the scope of the invention is not limited to the disclosed embodiments.

What is claimed is:

1. A pulse meter adapted to be attached to a human body to measure a pulse, comprising:
    a pulse wave detecting unit configured and arranged to detect a pulse wave based on a signal from a pulse wave sensor and output a pulse wave detection signal;
    a body motion component removing unit configured and arranged to remove a body motion component contained in said pulse wave detection signal based on a relative positional difference in a vertical direction between a position of a heart of the human body and a position where said pulse meter is attached; and
    a pulse rate calculating unit configured and arranged to calculate a pulse rate based on said pulse wave detection signal after said body motion component is removed.

2. The pulse meter as recited in claim 1, wherein
    said body motion component removing unit is further configured and arranged to include a body motion detecting unit configured and arranged to detect said body motion component expressed as a function of said relative positional difference and output a body motion detection signal.

3. The pulse meter as recited in claim 2, wherein said body motion detecting unit includes a pressure sensor configured and arranged to detect said body motion component.

4. The pulse meter as recited in claim 3, wherein said pressure sensor is positioned in a vicinity of said pulse wave sensor.

5. The pulse meter as recited in claim 3, wherein said pressure sensor and said pulse wave sensor are substantially stacked together.

6. The pulse meter as recited in claim 1, wherein
    said body motion component removing unit is further configured and arranged to include a difference detecting unit configured and arranged to detect said relative positional difference and output a body motion detection signal, and
    a body motion component generating unit configured and arranged to generate said body motion component based on said relative positional difference.

7. The pulse meter as recited in claim 1, wherein
said difference detecting unit includes an angle sensor configured and arranged to detect said relative positional difference as an angle difference of an actual position of said pulse meter with respect to a reference angle.

8. The pulse meter as recited in claim 7, wherein said angle sensor is positioned in a vicinity of said pulse wave sensor.

9. The pulse meter as recited in claim 7, wherein said angle sensor and said pulse wave sensor are substantially stacked together.

10. The pulse meter as recited in claim 7, wherein said angle sensor is configured and arranged to detect said angle difference based on a stationary acceleration.

11. The pulse meter as recited in claim 7, wherein said angle sensor is configured and arranged to have a rotary spindle and detect said angle difference based on a rotational state of said rotary spindle.

12. The pulse meter as recited in claim 6, wherein
said difference detecting unit is configured and arranged to include
an angle compensating unit configured and arranged to compensate said angle difference according to said body motion component when said angle difference indicates said position where said pulse meter is attached is higher than said position of the heart of the human body by an amount greater than a threshold value.

13. The pulse meter as recited in claim 1, wherein
said body motion component removing unit is configured and arranged to include
a removal processing unit configured and arranged to subtract a body motion detection signal corresponding to said body motion component based on said relative positional difference from said pulse wave detection signal.

14. The pulse meter as recited in claim 1, wherein
said body motion removing unit is configured and arranged to include
a first frequency analyzing unit configured and arranged to execute a frequency analysis of a body motion component detection signal corresponding to said body motion component based on said relative positional difference and generate first frequency analysis data,
a second frequency analyzing unit configured and arranged to execute a frequency analysis of said pulse wave detection signal and generate second frequency analysis data, and
a removal processing unit configured and arranged to subtract said first frequency analysis data from said second frequency analysis data.

15. The pulse meter as recited in claim 1, wherein
said body motion component removing unit is configured and arranged to include
a filter coefficient generating unit configured and arranged to generate an adaptive filter coefficient based on a body motion component detection signal corresponding to said body motion component based on said relative positional difference, and
a removal processing unit configured and arranged to subtract said body motion component detection signal applied with said adaptive filter coefficient from said pulse wave detection signal.

16. The pulse meter as recited in claim 1, further comprising a body motion information detecting unit configured and arranged to detect at least one of a pitch and step counts from said body motion component based on said relative positional difference contained in said pulse wave detection signal.

17. A method for measuring a pulse of a human body by a pulse meter attached on the human body, comprising:
performing pulse wave detection signal outputting process for outputting a pulse wave detection signal detected by a pulse wave sensor of the pulse meter;
performing body motion component removing process, using a processor, for removing a body motion component contained in said pulse wave detection signal based on a relative positional difference in a vertical direction between a position of a heart of the human body and a position where said pulse meter is attached; and
performing pulse rate calculating process, using a processor, for calculating a pulse rate based on said pulse wave detection signal after said body motion component is removed.

18. A wristwatch type information device, comprising:
a pulse wave detecting unit configured and arranged to be placed on a pulse wave detection position of the human body to detect a pulse wave based on a signal from a pulse wave sensor and output a pulse wave detection signal; and
a main body configured and arranged to be placed on a wrist of the human body, said main body including
a body motion component removing unit configured and arranged to remove a body motion component contained in said pulse wave detection signal based on a relative positional difference in a vertical direction between a position of a heart of the human body and a position where said pulse wave detecting unit is attached,
a pulse rate calculating unit configured and arranged to calculate a pulse rate based on said pulse wave detection signal after said body motion component is removed, and
a display unit configured and arranged to display said pulse rate.

19. A computer readable medium having program code means embodied therein for controlling, by a computer, a pulse meter adapted to be attached to a human body to measure a pulse having a pulse wave detecting unit configured and arranged to output a pulse wave signal, said computer readable program code means comprising:
removing a body motion component contained in said pulse wave detection signal based on a relative positional difference in a vertical direction between a position of a heart of the human body and a position where said pulse meter is attached; and
calculating a pulse rate based on said pulse wave detection signal after said body motion component is removed.

* * * * *